United States Patent
Zhang et al.

(10) Patent No.: US 11,751,475 B2
(45) Date of Patent: Sep. 5, 2023

(54) ORGANIC COMPOUND, DISPLAY PANEL AND DISPLAY APPARATUS

(71) Applicant: Xiamen Tianma Micro-Electronics Co., Ltd., Xiamen (CN)

(72) Inventors: Lei Zhang, Shanghai (CN); Wei Gao, Shanghai (CN); Jinghua Niu, Shanghai (CN); Wenpeng Dai, Shanghai (CN); Wenjing Xiao, Shanghai (CN)

(73) Assignee: Xiamen Tianma Micro-Electronics Co., Ltd., Xiamen (CN)

( * ) Notice: Subject to any disclaimer, the term of this patent is extended or adjusted under 35 U.S.C. 154(b) by 642 days.

(21) Appl. No.: 16/827,739

(22) Filed: Mar. 24, 2020

(65) Prior Publication Data

US 2020/0227654 A1 Jul. 16, 2020

(30) Foreign Application Priority Data

Dec. 26, 2019 (CN) .......................... 201911365684.4

(51) Int. Cl.
*C07D 401/04* (2006.01)
*C07D 401/10* (2006.01)
(Continued)

(52) U.S. Cl.
CPC ....... *H10K 85/6572* (2023.02); *C07D 401/04* (2013.01); *C07D 401/10* (2013.01);
(Continued)

(58) Field of Classification Search
CPC .. C07D 401/04; C07D 401/10; C07D 403/04; C07D 403/10; C07D 403/14; H01L 51/0052; H01L 51/0067; H01L 51/0072
See application file for complete search history.

(56) References Cited

U.S. PATENT DOCUMENTS 8,470,454 B2 * 6/2013 Kim ....................... C09B 57/00
544/242
10,882,850 B2 * 1/2021 Zhang ................. H01L 51/0058
(Continued)

FOREIGN PATENT DOCUMENTS

CN 102089288 A 6/2011
CN 103329619 A 9/2013
(Continued)

OTHER PUBLICATIONS

Office Action of Chinese Patent Application No. 201911365684.4 dated Sep. 1, 2020.
(Continued)

*Primary Examiner* — Vu A Nguyen
(74) *Attorney, Agent, or Firm* — Kilpatrick Townsend & Stockton, LLP

(57) ABSTRACT

The present disclosure provides an organic compound, having a structure represented by Formula 1, in which $L_1$, $L_2$, and $L_3$ are each independently selected from a single bond, or C4-C30 arylene; $X_1$, $X_2$, and $X_3$ are each independently selected from CRa, or N, and at least one of $X_1$, $X_2$, or $X_3$ is N; $Ar_1$, $Ar_2$, and $Ar_3$ are each independently selected from C6-C60 aryl, a structure represented by Formula 2, or a structure represented by Formula 3; at least one of $Ar_1$, $Ar_2$, or $Ar_3$ is the structure represented by Formula 2, and at least one of $Ar_1$, $Ar_2$, or $Ar_3$ is the structure represented by Formula 3; $X_4$, $X_5$, $X_6$, and $X_7$ are each independently selected from CRb, or N, and at least one of $X_4$, $X_5$, $X_6$, or $X_7$ is N; # indicates a bonding position; and Ra and Rb are specifically defined in the specification.

(Continued)

US 11,751,475 B2
Page 2

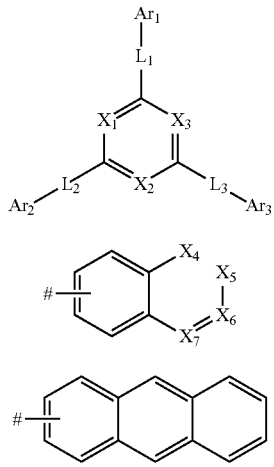

5 Claims, 1 Drawing Sheet

(51) Int. Cl.
| | |
|---|---|
| C07D 401/14 | (2006.01) |
| C07D 403/04 | (2006.01) |
| C07D 403/10 | (2006.01) |
| C07D 403/14 | (2006.01) |
| H01L 51/00 | (2006.01) |
| H01L 51/50 | (2006.01) |
| H10K 85/60 | (2023.01) |
| C09K 11/06 | (2006.01) |
| H10K 50/15 | (2023.01) |
| H10K 50/16 | (2023.01) |
| H10K 50/82 | (2023.01) |
| H10K 50/84 | (2023.01) |
| H10K 102/00 | (2023.01) |

(52) U.S. Cl.
CPC ......... *C07D 401/14* (2013.01); *C07D 403/10* (2013.01); *C09K 11/06* (2013.01); *H10K 85/615* (2023.02); *H10K 85/626* (2023.02); *H10K 85/654* (2023.02); *C09K 2211/1018* (2013.01); *H10K 50/15* (2023.02); *H10K 50/16* (2023.02); *H10K 50/82* (2023.02); *H10K 50/84* (2023.02); *H10K 2102/3026* (2023.02)

(56) References Cited

U.S. PATENT DOCUMENTS

| | | | | |
|---|---|---|---|---|
| 11,434,223 | B2 * | 9/2022 | Zhang | ............... C07D 239/26 |
| 2009/0166670 | A1 | 7/2009 | Park et al. | |
| 2016/0141519 | A1 | 5/2016 | Seo et al. | |

FOREIGN PATENT DOCUMENTS

| | | | | |
|---|---|---|---|---|
| CN | 104835921 A | | 8/2015 | |
| CN | 106946859 A | * | 7/2017 | ........... C07D 401/14 |
| CN | 109180567 A | * | 1/2019 | ........... C07D 213/06 |
| CN | 109180567 A | | 1/2019 | |
| WO | WO-2018103749 A1 | * | 6/2018 | ........... C07D 251/24 |

OTHER PUBLICATIONS

Office Action of Chinese Patent Application No. 201911365684.4 dated Mar. 10, 2021.

* cited by examiner

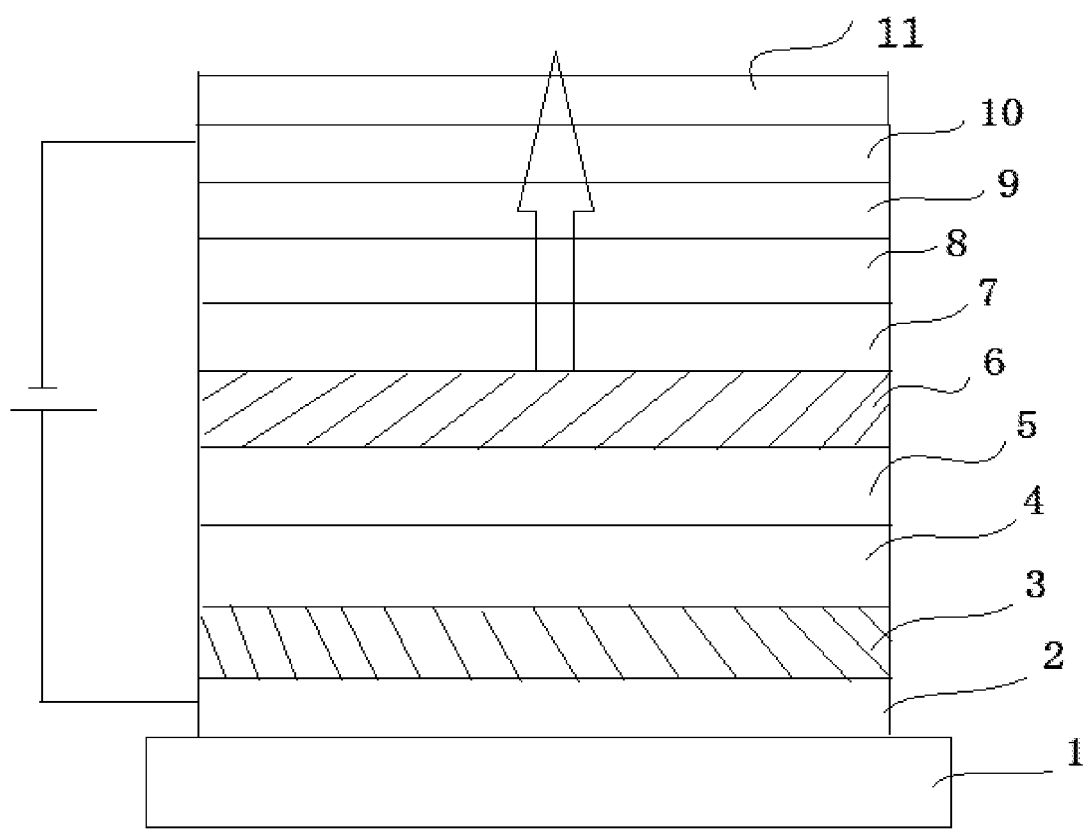

ORGANIC COMPOUND, DISPLAY PANEL AND DISPLAY APPARATUS

CROSS-REFERENCE TO RELATED APPLICATIONS

The present application claims priority to Chinese Patent Application No. 201911365684.4, filed on Dec. 26, 2019, the content of which is incorporated herein by reference in its entirety.

FIELD

The present disclosure relates to the field of organic electroluminescent materials, and in particular, to an organic compound, a display panel, and a display apparatus.

BACKGROUND

Organic Light-Emitting diodes (OLEDs) have advanced greatly through decades of development. Although an internal quantum efficiency thereof can nearly reach 100%, an external quantum efficiency thereof is only about 20%. Most light is confined inside the light-emitting device due to factors such as substrate mode loss, surface plasma loss, and waveguide effect, resulting in a large amount of energy loss.

In a top-emission device, an organic capping layer (CPL) is vapor-deposited on a translucent metal electrode Al to adjust an optical interference distance, suppress external light reflection, and suppress extinction caused by surface plasma energy movement, to improve light extraction efficiency and luminous efficiency.

OLEDs have high requirements on performance of CPL materials: no absorption in visible wavelength region (400 nm to 700 nm); high refractive index (generally, n>2.1 eV), and low extinction coefficient (k≤0.00) in a wavelength range of 400 nm to 600 nm; high glass transition temperature and molecular thermal stability (the material should have a high glass transition temperature while being evaporable without thermal decomposition).

Therefore, continuous researches are still necessary in order to improve performances of the CPL materials.

SUMMARY

In view of the above, one purpose of the present disclosure is to provide a novel organic compound having an aza benzene structure as a central skeleton, which is connected with anthracene and quinolinazole, as represented by Formula 1:

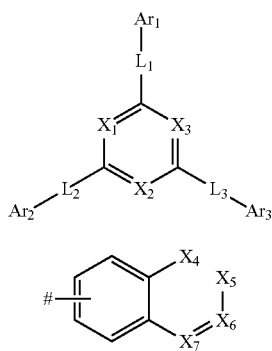

-continued

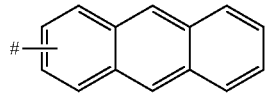

wherein $L_1$, $L_2$, and $L_3$ are each independently selected from a single bond (i.e., $Ar_1$, $Ar_2$, and $Ar_3$ are directly bonded to an aromatic ring containing $X_1$, $X_2$, and $X_3$), or C4-C30 arylene;

$X_1$, $X_2$, and $X_3$ are each independently selected from CRa, or N, and at least one of $X_1$, $X_2$, or $X_3$ is N;

$Ar_1$, $Ar_2$, and $Ar_3$ are each independently selected from C6-C60 aryl, a structure represented by Formula 2, or a structure represented by Formula 3; at least one of $Ar_1$, $Ar_2$, or $Ar_3$ is the structure represented by Formula 2, and at least one of $Ar_1$, $Ar_2$, or $Ar_3$ is the structure represented by Formula 3;

wherein $X_4$, $X_5$, $X_6$, and $X_7$ are each independently selected from CRb, or N, and at least one of $X_4$, $X_5$, $X_6$, or $X_7$ is N;

wherein # indicates a bonding position;

wherein Ra is hydrogen, deuterium, halogen, nitro, cyano, thioalkyl, a substituted or unsubstituted C1 to C10 alkyl, a substituted or unsubstituted C6 to C30 aryl, a substituted or unsubstituted C2 to C30 heterocyclic group, a substituted or unsubstituted C2 to C30 alkenyl, or a substituted or unsubstituted C2 to C30 alkynyl; and Ra is an independent group or a group connected to an adjacent ring, for providing a substituted or unsubstituted aliphatic monocyclic or polycyclic ring, a substituted or unsubstituted aromatic monocyclic or polycyclic ring, or a substituted or unsubstituted heteroaromatic monocyclic or polycyclic ring; and wherein Rb is hydrogen, deuterium, halogen, nitro, cyano, thioalkyl, a substituted or unsubstituted C1 to C10 alkyl, a substituted or unsubstituted C6 to C30 aryl, a substituted or unsubstituted C2 to C30 heterocyclic group, a substituted or unsubstituted C2 to C30 alkenyl, or a substituted or unsubstituted C2 to C30 alkynyl; and Rb is an independent group or a group connected to an adjacent ring, for providing a substituted or unsubstituted aliphatic monocyclic or polycyclic ring, a substituted or unsubstituted aromatic monocyclic or polycyclic ring, or a substituted or unsubstituted heteroaromatic monocyclic or polycyclic ring.

In another aspect, the present disclosure provides a display panel, including an organic light-emitting device. The organic light-emitting device comprises an anode, a cathode, and at least one organic layer disposed between the anode and the cathode. A material of the at least one organic layer comprises at least one of compounds as described above.

In another aspect, the present disclosure provides a display apparatus, including the above display panel.

BRIEF DESCRIPTION OF DRAWINGS

FIGURE is a schematic structural diagram of an organic light-emitting device according to an embodiment of the present disclosure.

DESCRIPTION OF EMBODIMENTS

The embodiments of the present disclosure will be described in detail below with reference to the accompanying drawings.

It should be understood that, the described embodiments are merely a part of, rather than all of the embodiments of the present disclosure. Based on these embodiments described in the present disclosure, other embodiments obtained by those skilled in the art without paying creative efforts shall fall within the protection scope of the present disclosure.

The terms in the embodiments of the present disclosure are merely used for describing specific embodiments, but not intended to limit the present disclosure. The singular forms such as "a", "an", "said" and "the" are also intended to include the plural forms, unless the context indicates otherwise.

It should be understood that the term "and/or" used in the context of the present disclosure is to describe a correlation relation of related objects, indicating that there may be three relations, e.g., A and/or B may indicate only A, both A and B, and only B. In addition, the symbol "/" in the context generally indicates that the relation between the objects in front and at the back of "/" is an "or" relationship.

It should be understood that terms "substantially", "approximately", "about", and the like in the pending claims and the description of embodiments of the present disclosure mean that a value is within a reasonable range of process operation or tolerance, rather than an accurate value.

In one aspect, the present disclosure provides a novel organic compound having an aza benzene structure as a central skeleton, which is connected with anthracene and quinolinazole, as represented by Formula 1:

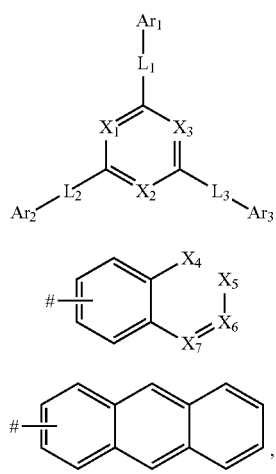

wherein in Formula 1, $L_1$, $L_2$, and $L_3$ are each independently selected from a single bond (i.e., $Ar_1$, $Ar_2$, and $Ar_3$ are directly bonded to an aromatic ring containing $X_1$, $X_2$, and $X_3$), or C4-C30 arylene;

$X_1$, $X_2$, and $X_3$ are each independently selected from CRa, or N, and at least one of $X_1$, $X_2$, or $X_3$ is N;

$Ar_1$, $Ar_2$, and $Ar_3$ are each independently selected from C6-C60 aryl, a structure represented by Formula 2, or a structure represented by Formula 3; at least one of $Ar_1$, $Ar_2$, or $Ar_3$ is the structure represented by Formula 2, and at least one of $Ar_1$, $Ar_2$, or $Ar_3$ is the structure represented by Formula 3;

wherein in Formula 2, $X_4$, $X_5$, $X_6$, and $X_7$ are each independently selected from CRb, or N, and at least one of $X_4$, $X_5$, $X_6$, or $X_7$ is N;

wherein # indicates a bonding position;

wherein Ra is hydrogen, deuterium, halogen, nitro, cyano, thioalkyl, a substituted or unsubstituted C1 to C10 alkyl, a substituted or unsubstituted C6 to C30 aryl, a substituted or unsubstituted C2 to C30 heterocyclic group, a substituted or unsubstituted C2 to C30 alkenyl, or a substituted or unsubstituted C2 to C30 alkynyl; and Ra is an independent group or a group connected to an adjacent ring, for providing a substituted or unsubstituted aliphatic monocyclic or polycyclic ring, a substituted or unsubstituted aromatic monocyclic or polycyclic ring, or a substituted or unsubstituted heteroaromatic monocyclic or polycyclic ring; and wherein Rb is hydrogen, deuterium, halogen, nitro, cyano, thioalkyl, a substituted or unsubstituted C1 to C10 alkyl, a substituted or unsubstituted C6 to C30 aryl, a substituted or unsubstituted C2 to C30 heterocyclic group, a substituted or unsubstituted C2 to C30 alkenyl, or a substituted or unsubstituted C2 to C30 alkynyl; and Rb is an independent group or a group connected to an adjacent ring, for providing a substituted or unsubstituted aliphatic monocyclic or polycyclic ring, a substituted or unsubstituted aromatic monocyclic or polycyclic ring, or a substituted or unsubstituted heteroaromatic monocyclic or polycyclic ring.

The organic compound of the present disclosure, having a high refractive index, can be used as a capping layer (CPL) in an organic light-emitting device, to effectively improve EQE of an organic electroluminescent device. The organic compound of the present disclosure has a small extinction coefficient in a blue light region (400-450 nm), and has almost no absorption of blue light, which is conducive to improving luminous efficiency. This novel organic compound can be used to improve the light extraction efficiency and luminous efficiency of organic light-emitting devices (most effective for blue light pixels), and reduce an angle-dependence of light emission of the organic light-emitting devices (most effective for red/green light pixels), while effectively blocking water and oxygen from external environment, and protecting the OLED display panel from being eroded with water and oxygen.

According to an embodiment of the compound of the present disclosure, in Formula 1, $L_1$ and $L_2$ are identical; or $L_1$ and $L_3$ are identical; or $L_2$ and $L_3$ are identical.

According to an embodiment of the compound of the present disclosure, in Formula 1, $L_1$, $L_2$, and $L_3$ are identical.

According to an embodiment of the compound of the present disclosure, in Formula 1, $Ar_1$ and $Ar_2$ are identical; or $Ar_1$ and $Ar_3$ are identical; or $Ar_2$ and $Ar_3$ are identical.

According to an embodiment of the compound of the present disclosure, in Formula 1, $Ar_1$, $Ar_2$, and $Ar_3$ are identical.

According to an embodiment of the compound of the present disclosure, in Formula 2, at least two of $X_4$, $X_5$, $X_6$, or $X_7$ are N.

According to an embodiment of the compound of the present disclosure, in Formula 1, $L_1$, $L_2$, and $L_3$ are each independently a single bond,

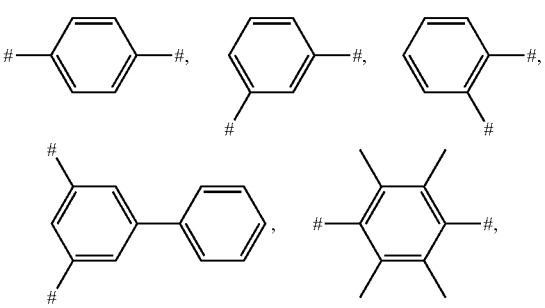

-continued
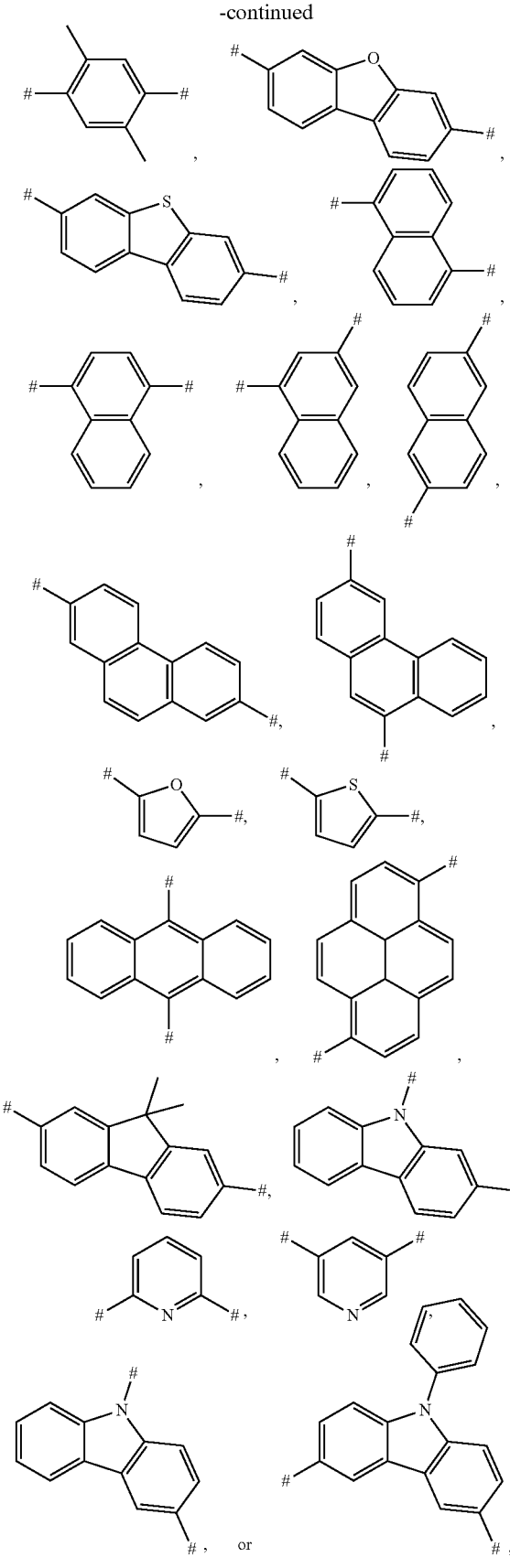
wherein # indicates a bonding position.
According to an embodiment of the compound of the present disclosure, the structure represented by Formula 2 is one of the following structures:
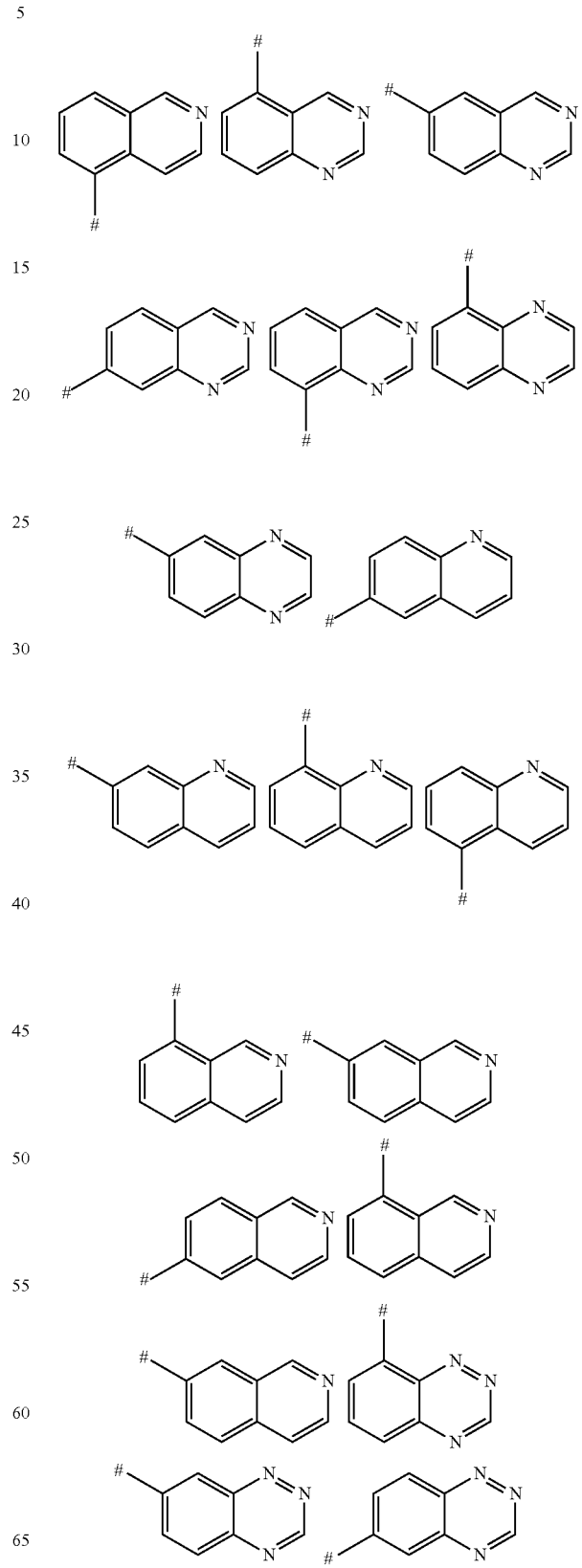

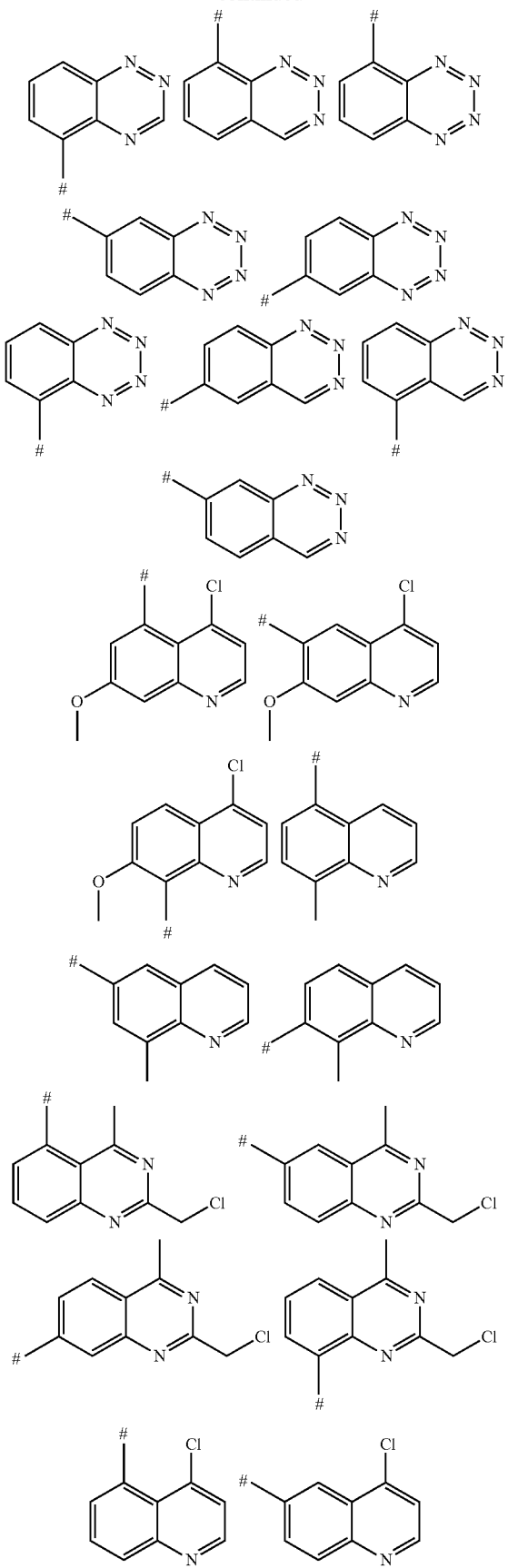
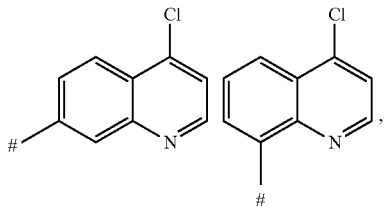
wherein # indicates a bonding position.
According to an embodiment of the compound of the present disclosure, in Formula 1, $X_1$, $X_2$, and $X_3$ are each independently selected from CRa, or N, and at least one of $X_1$, $X_2$, or $X_3$ is N.
According to an embodiment of the compound of the present disclosure, the organic compound is one of the following compounds:
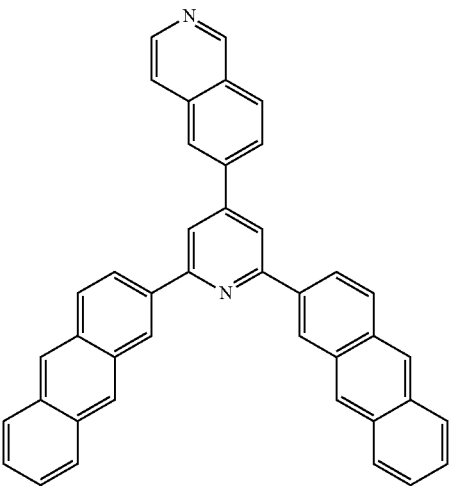
CP003
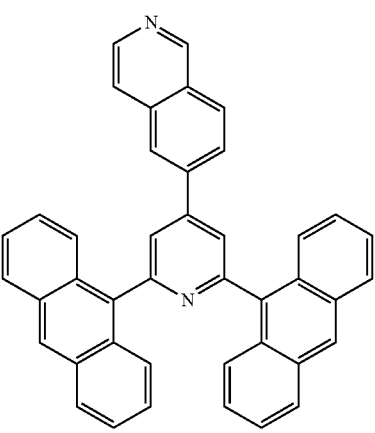
CP026

CP036
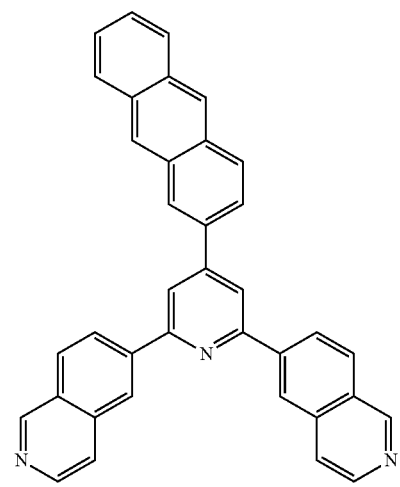
CP043
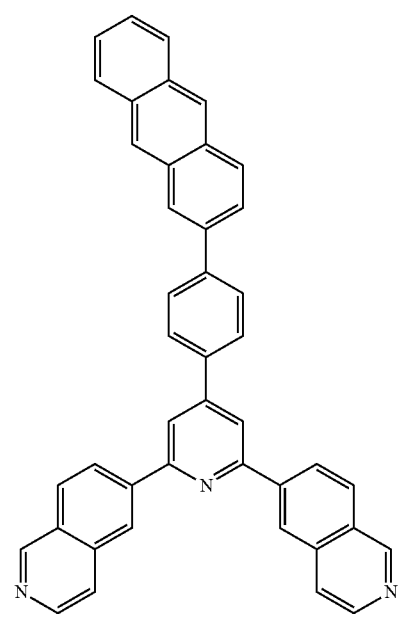
CP045
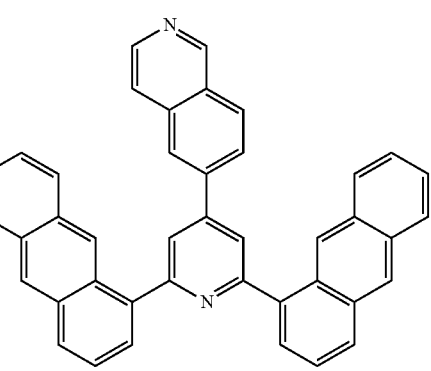
CP046
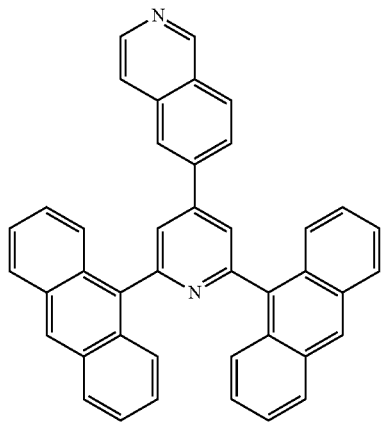
CP047
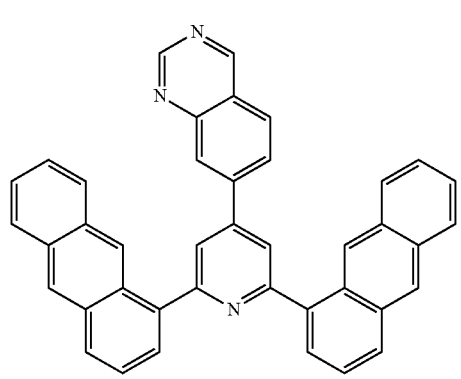
CP048
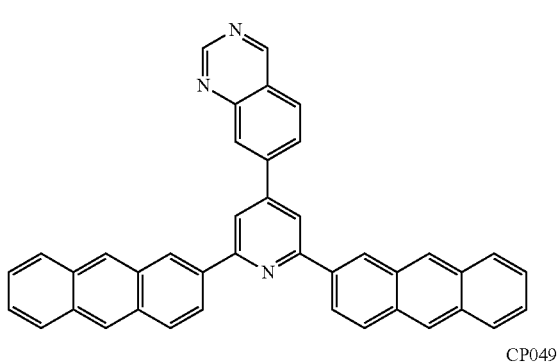
CP049
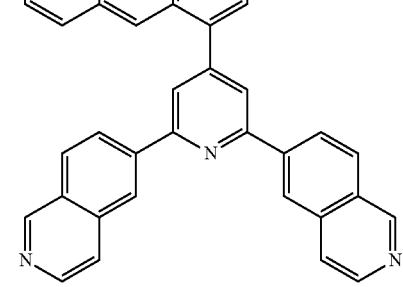

CP050
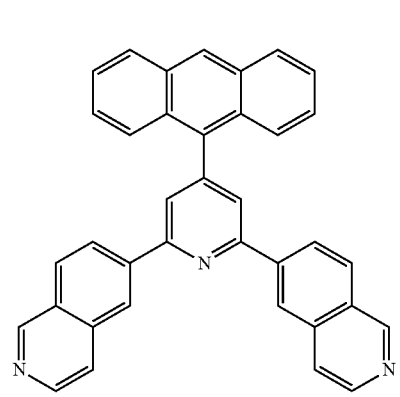
CP051
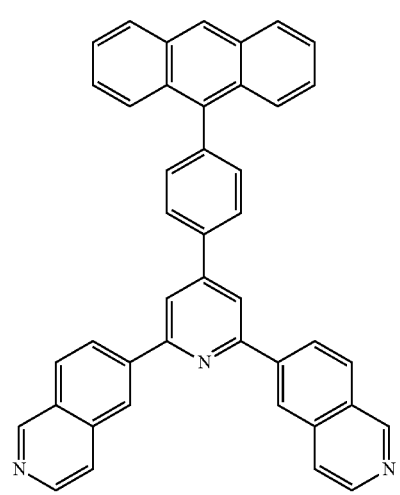
CP052
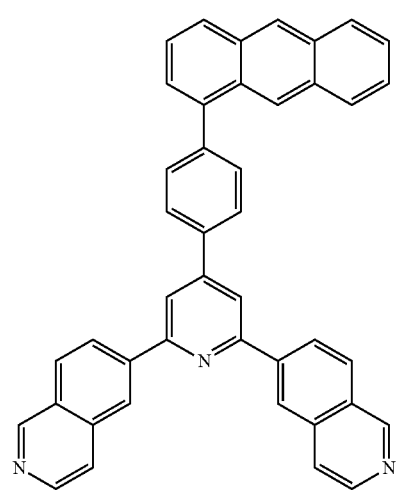
CP053
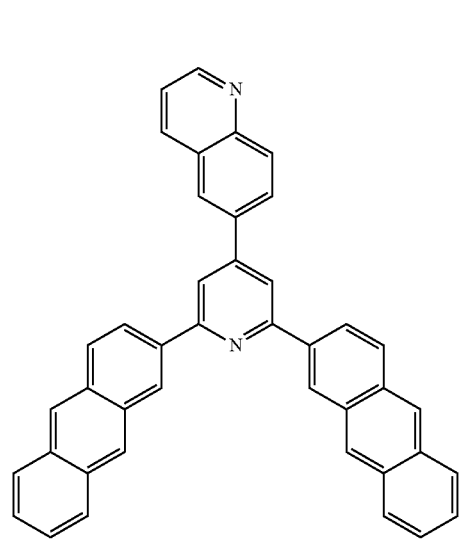
CP054
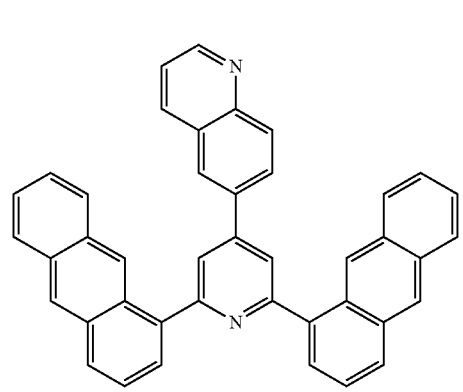
CP055
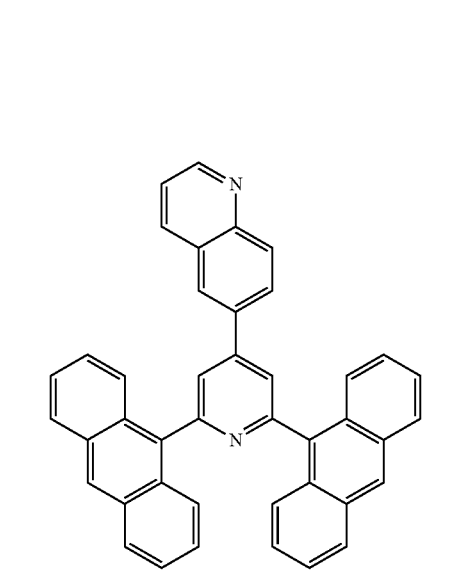

CP056
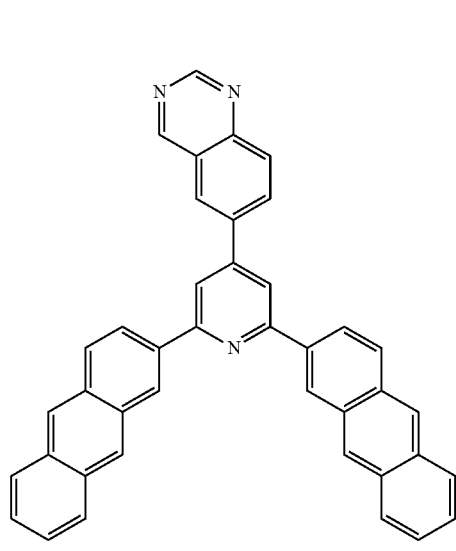
CP059
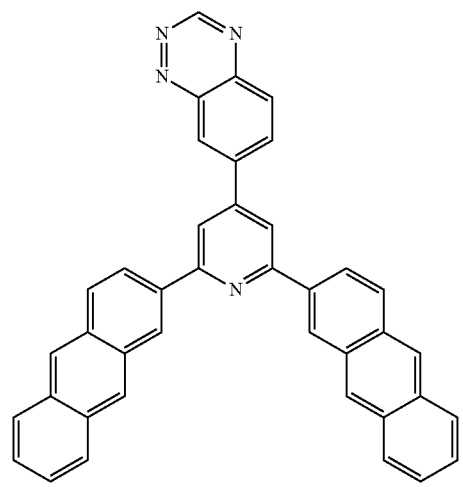
CP057
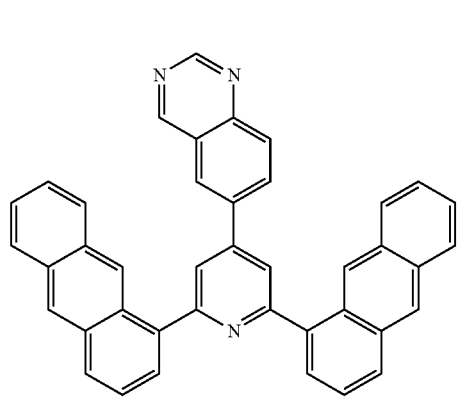
CP060
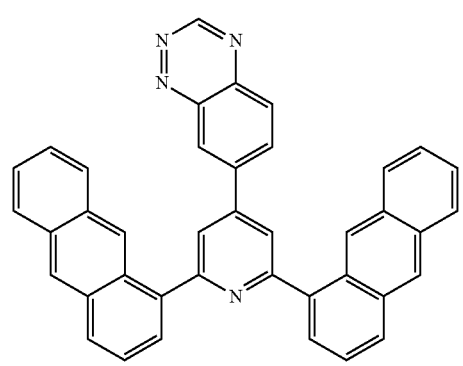
CP058
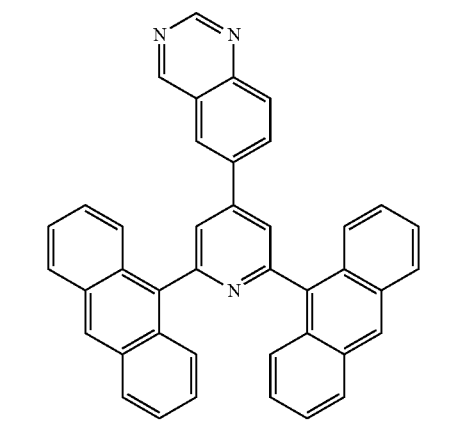
CP061
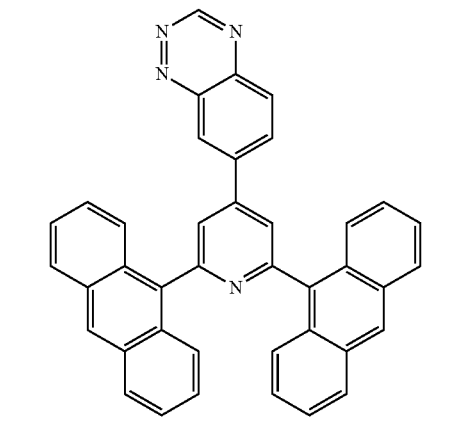

CP062
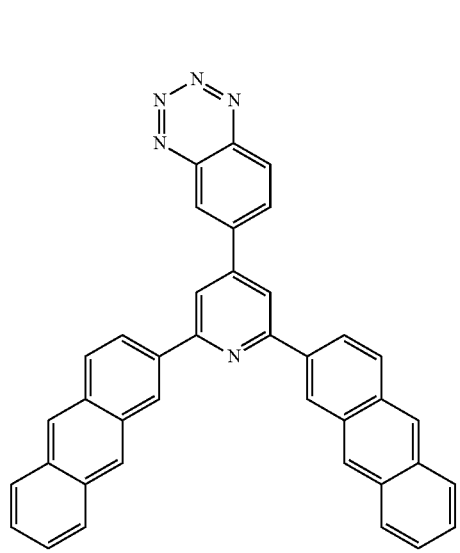
CP065
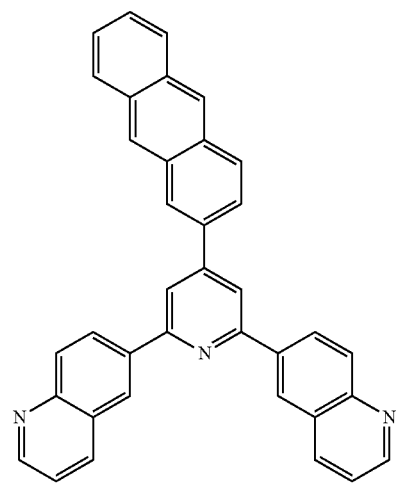
CP063
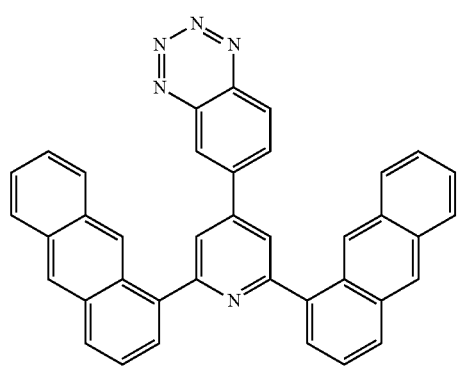
CP066
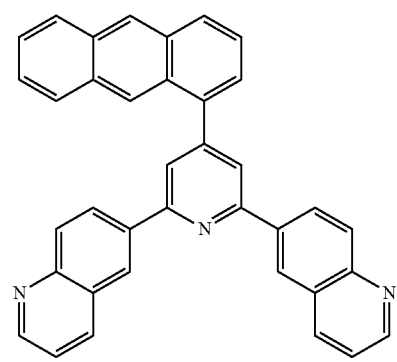
CP064
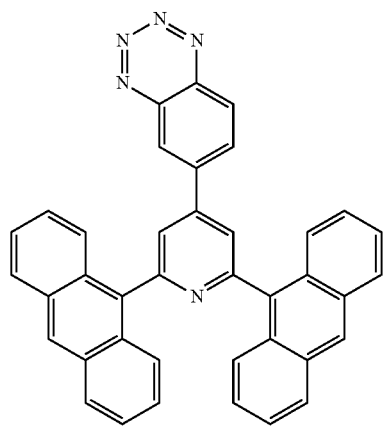
CP067
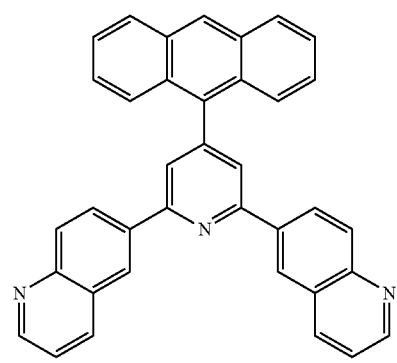

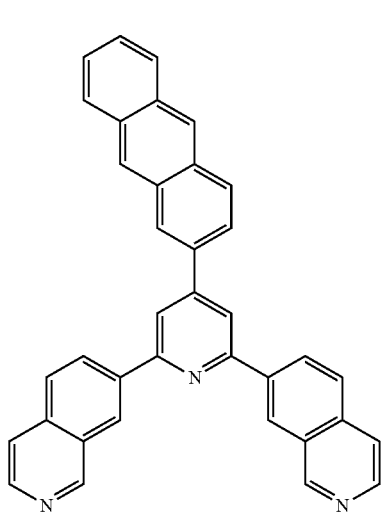
CP068
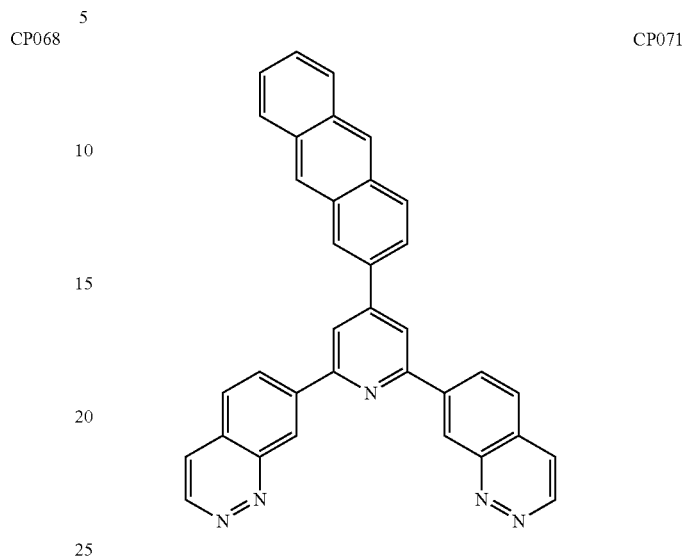
CP071 CP072 CP073
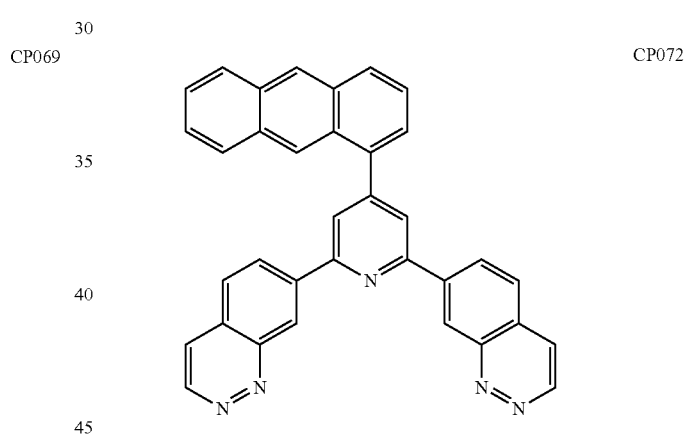
CP069
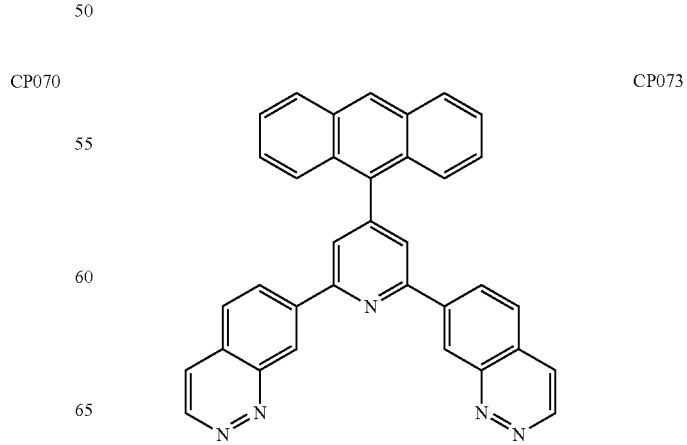
CP070

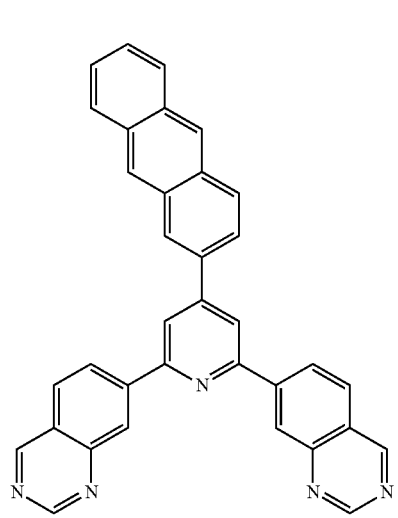
CP074
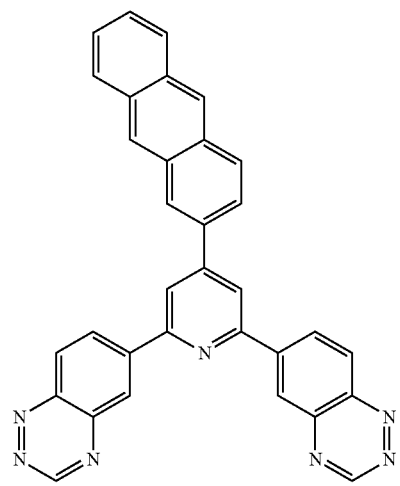
CP077
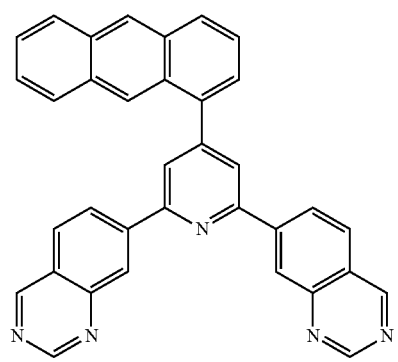
CP075
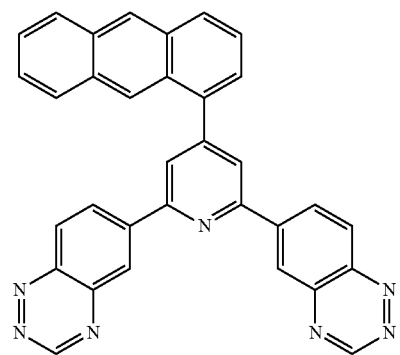
CP078
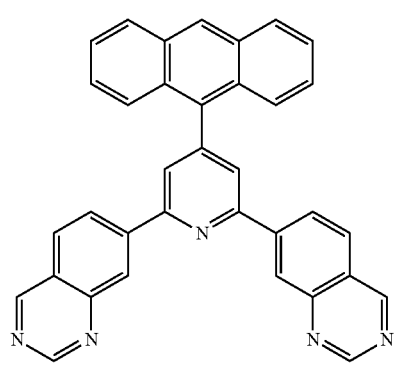
CP076
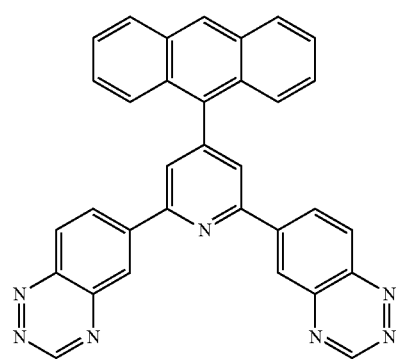
CP079

CP080
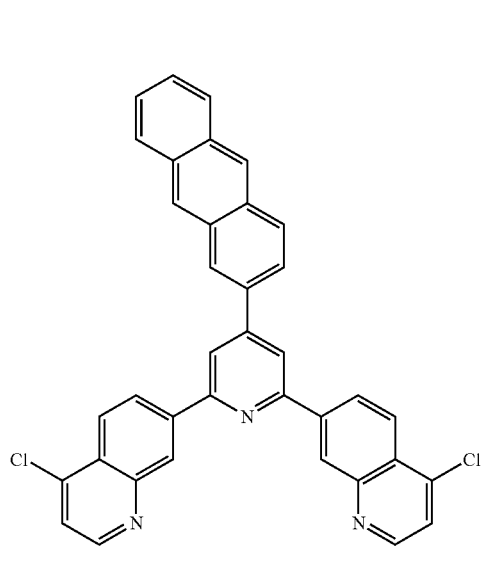
CP146
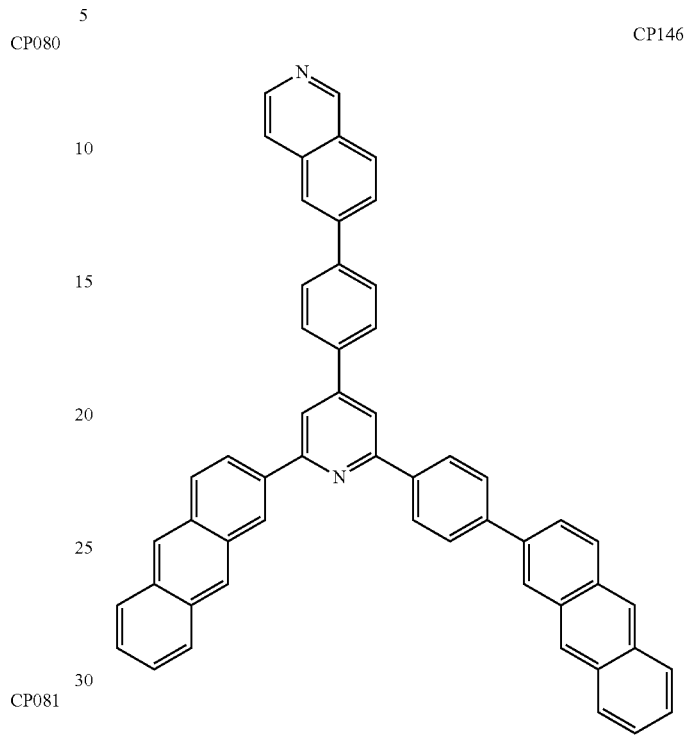
CP081
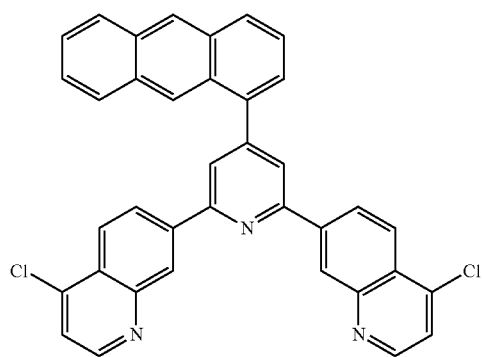
CP082
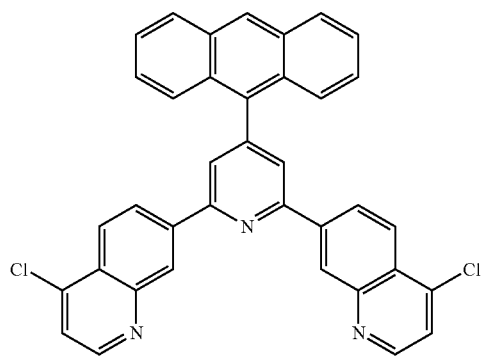
CP147
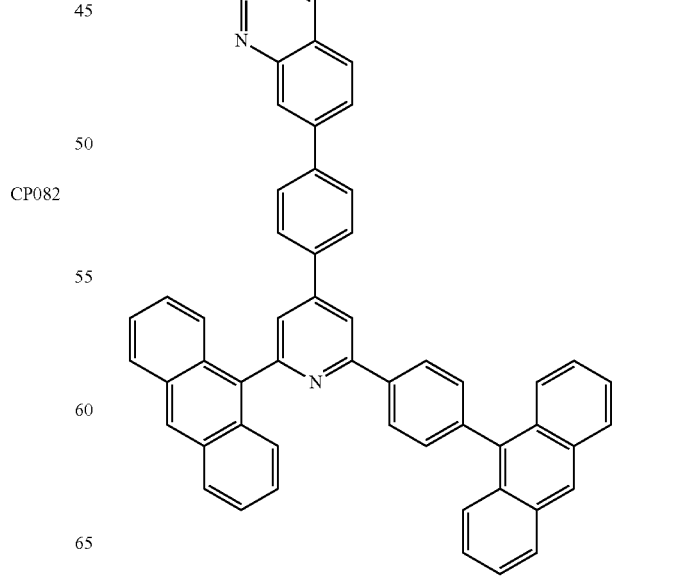

CP149
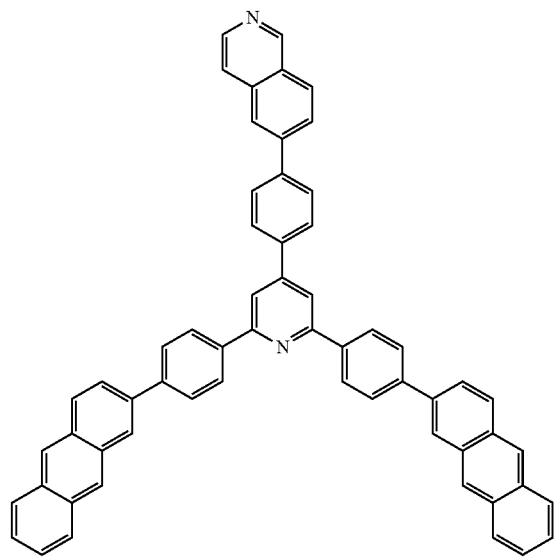
CP150
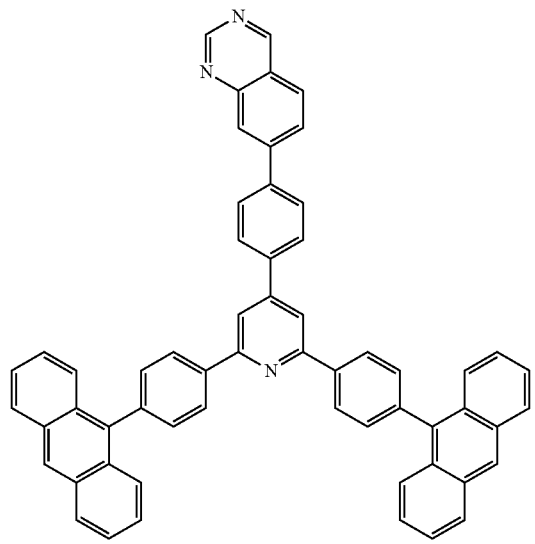
CP148
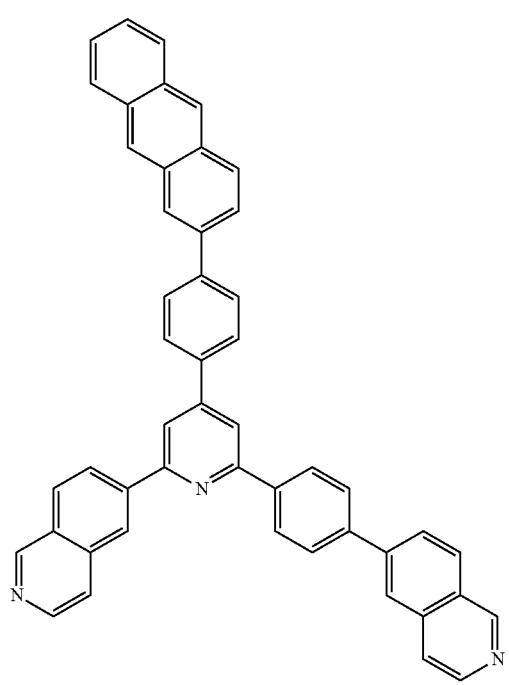
CP151
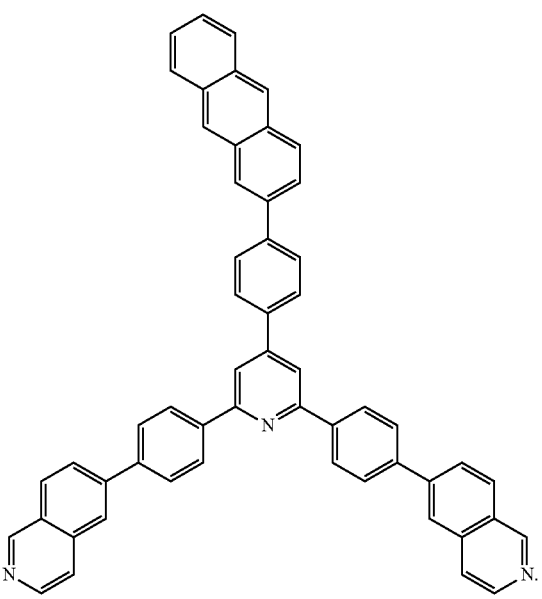
According to an embodiment of the compound of the present disclosure, in Formula 1, at least two of $X_1$, $X_2$, or $X_3$ are N.
According to an embodiment of the compound of the present disclosure, the organic compound is one of the following compounds:

CP001
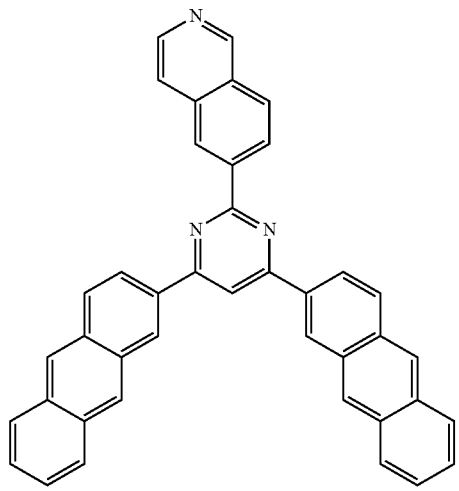
CP002
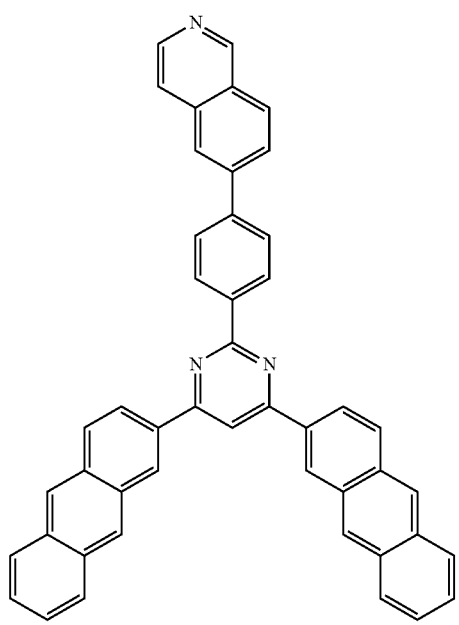
CP004
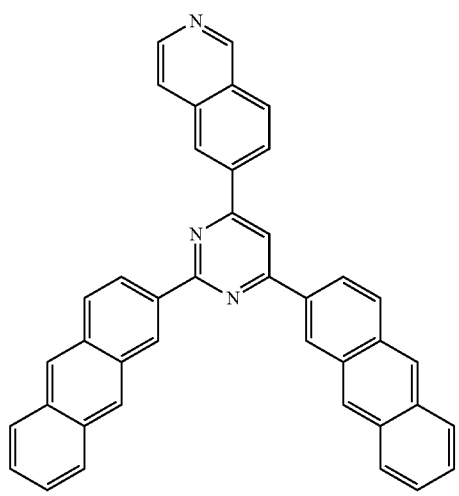
-continued
CP005
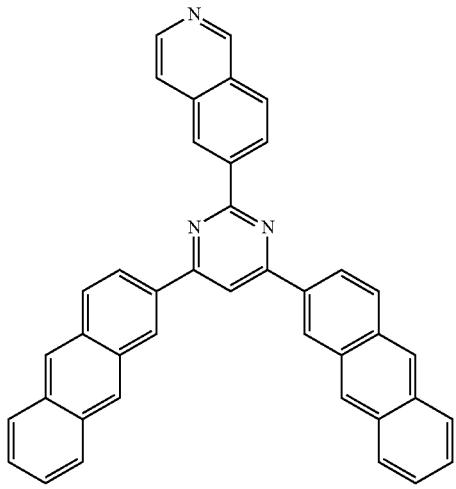
CP007
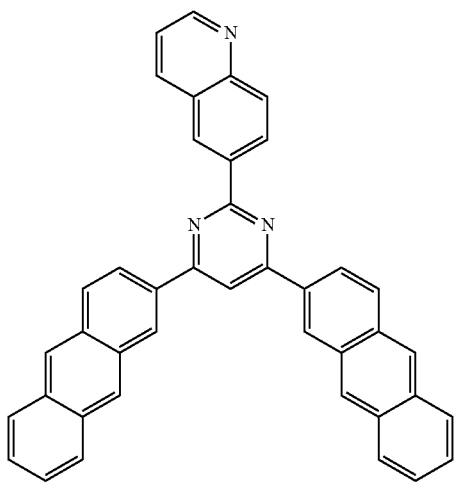
CP008
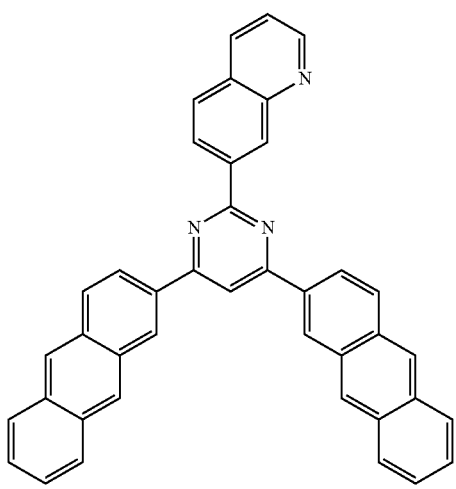

CP009
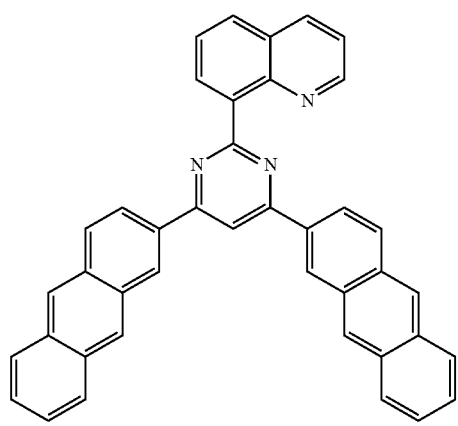
CP010
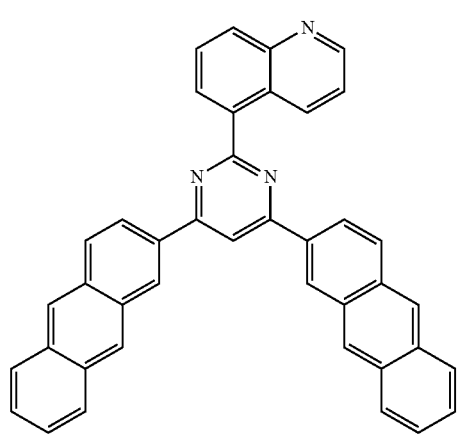
CP011
CP012
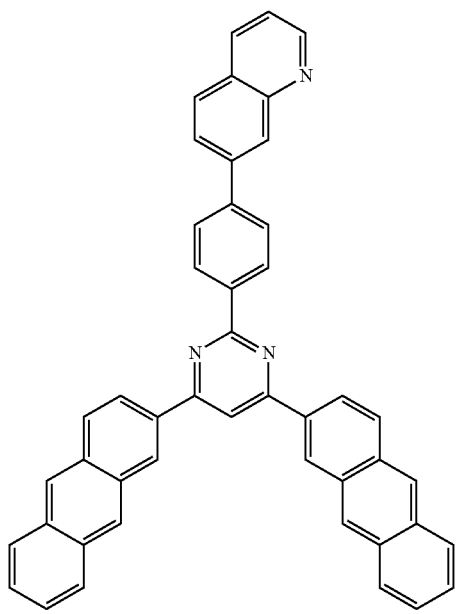
CP013
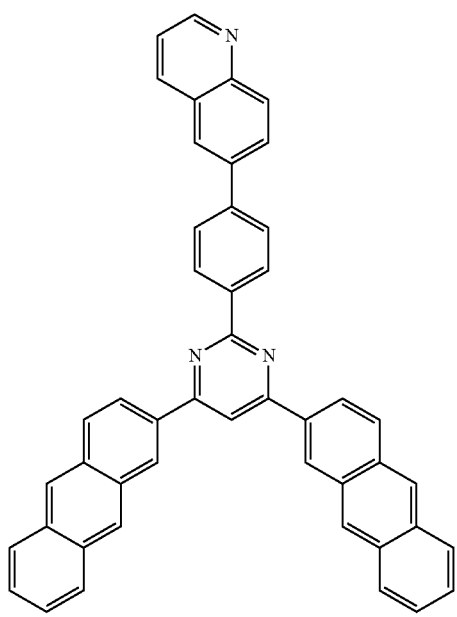

-continued
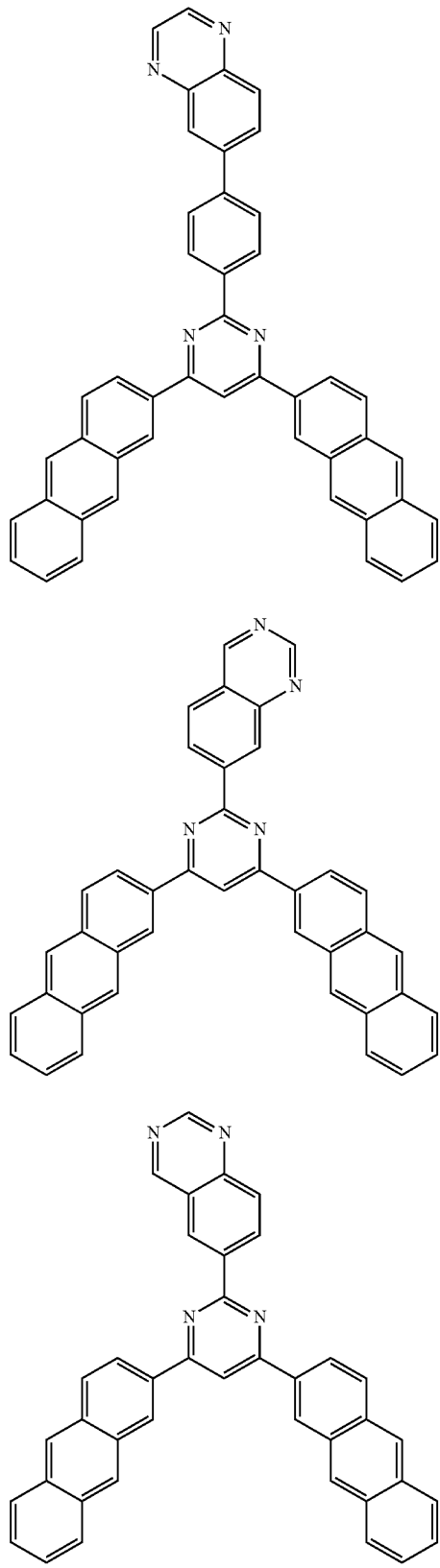
CP014
CP015
CP016
-continued
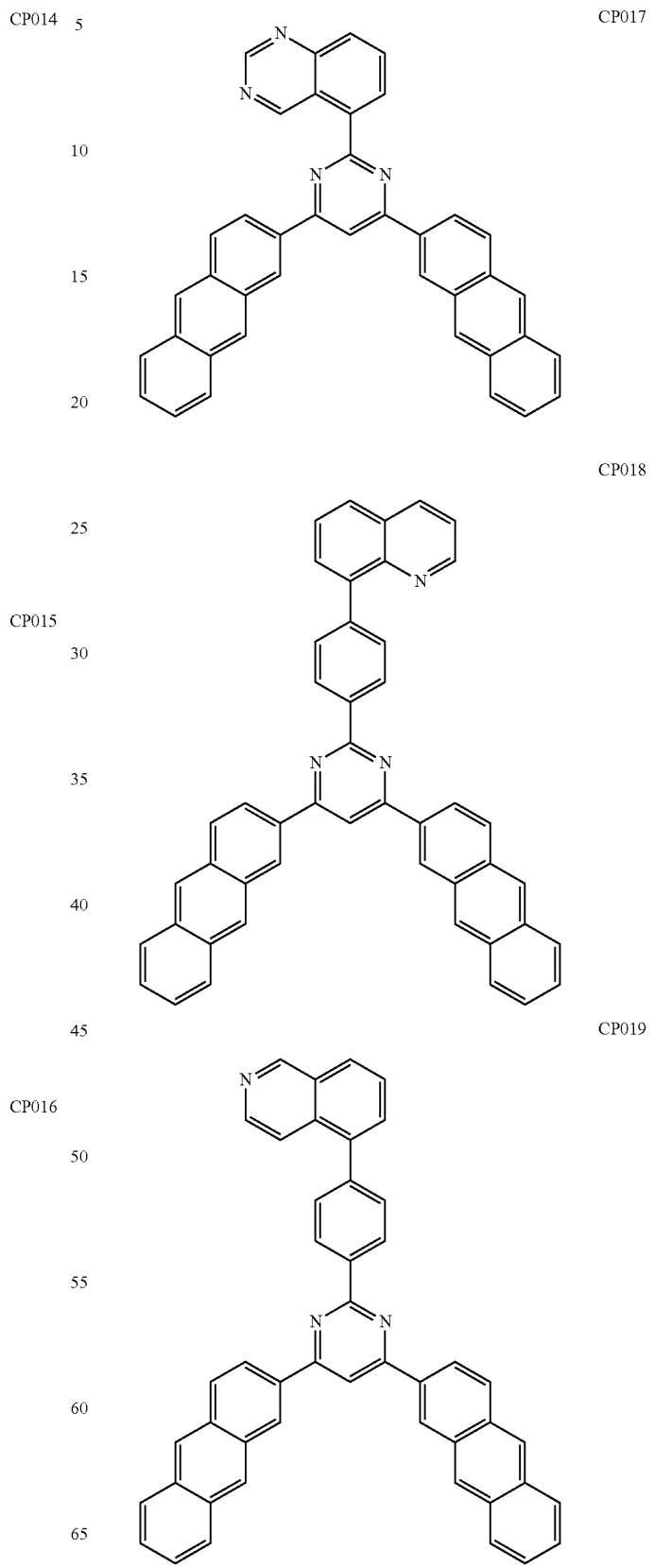
CP017
CP018
CP019

-continued
CP020
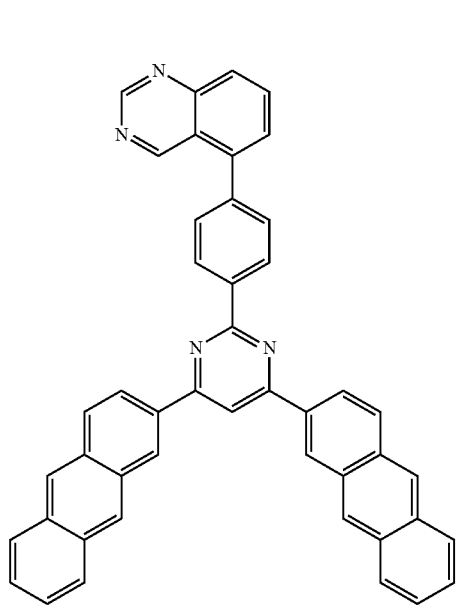
CP021
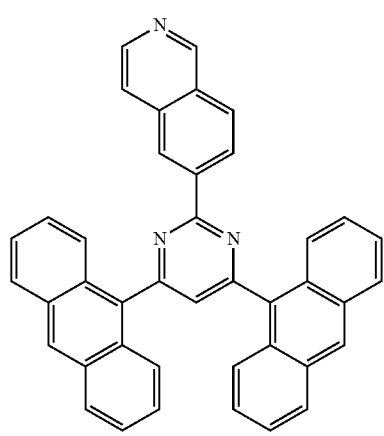
CP022
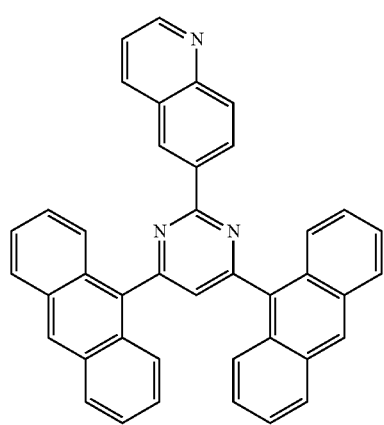
-continued
CP023
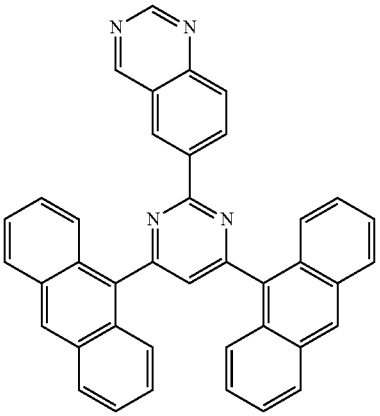
CP024
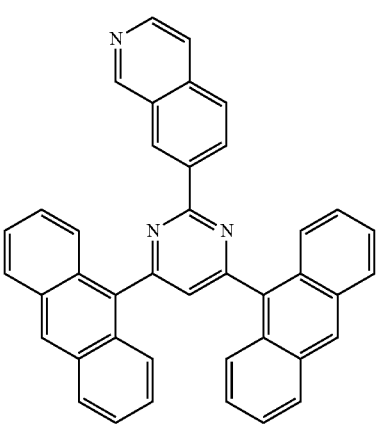
CP025
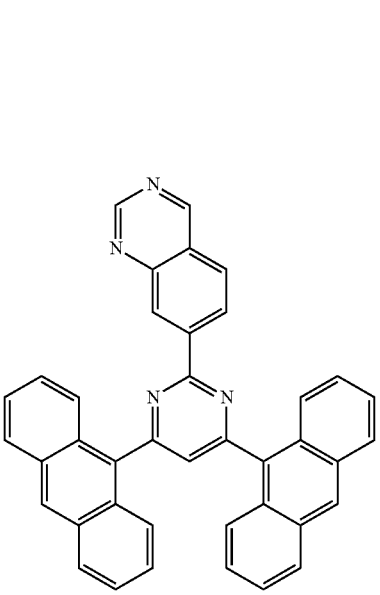

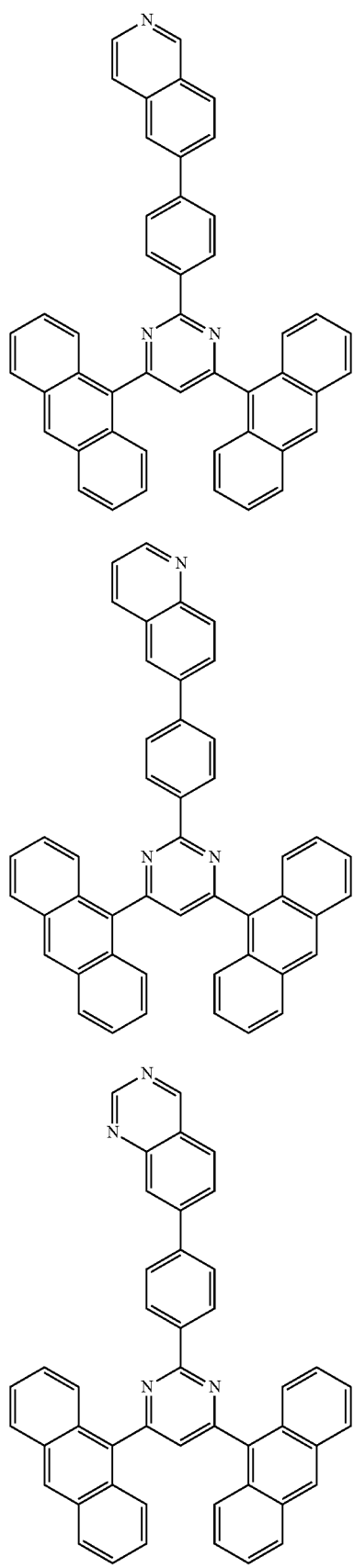
CP027
CP028
CP029
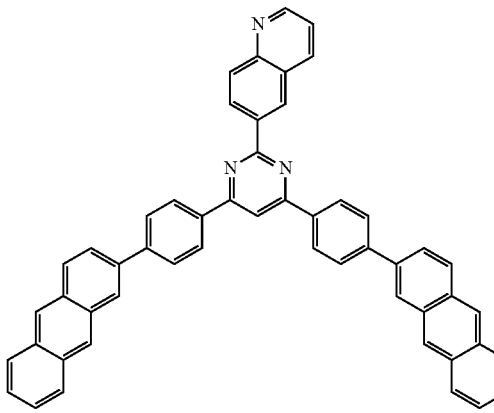
CP030
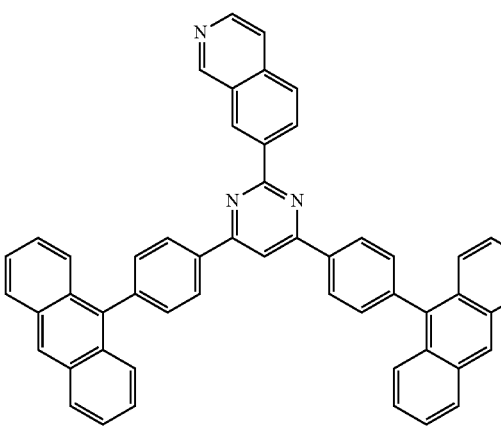
CP031
CP032

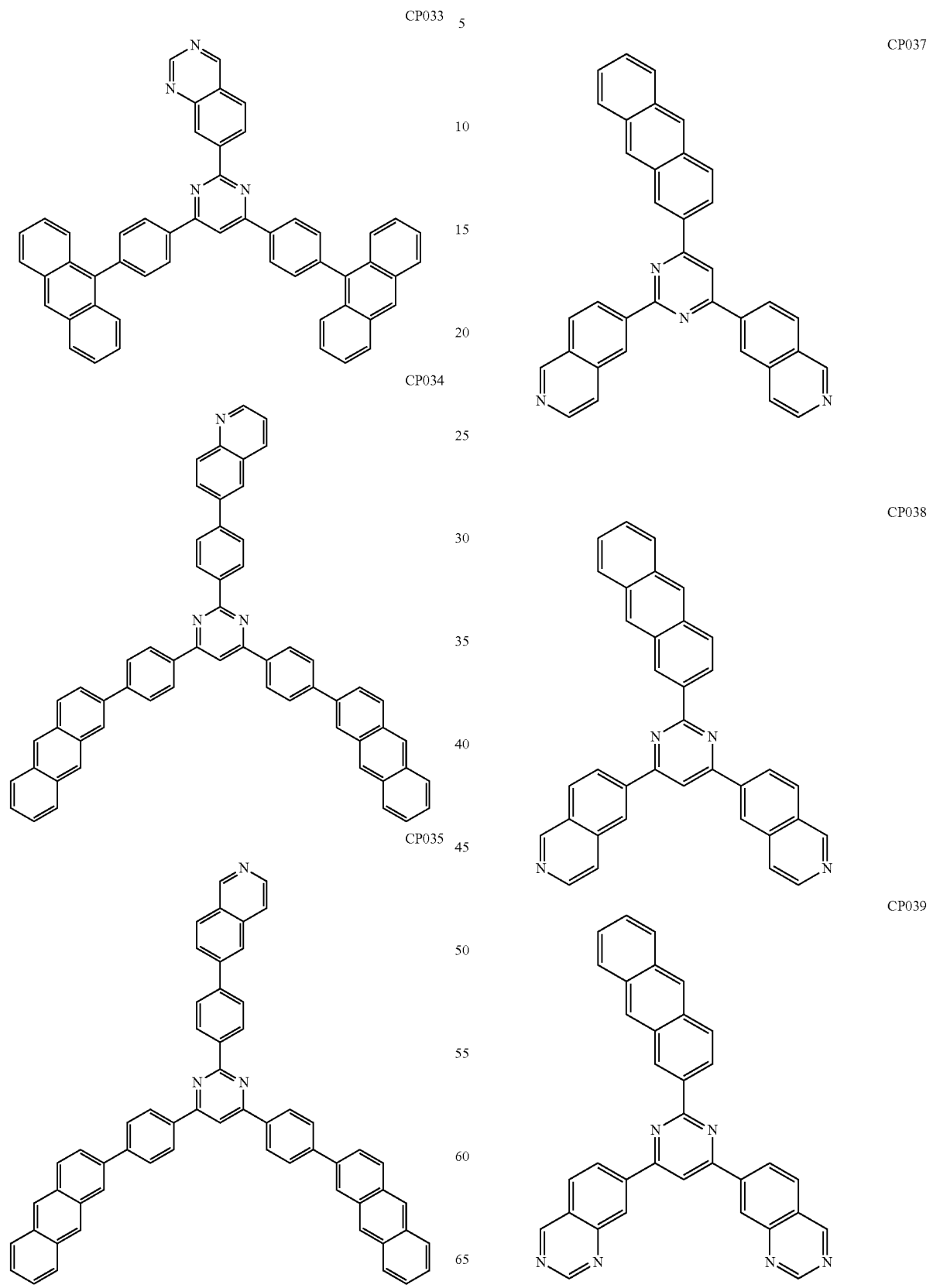

CP040
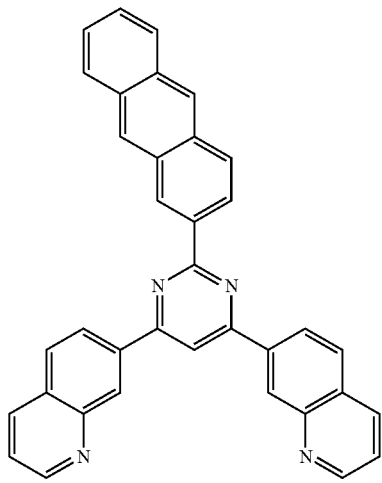
CP041
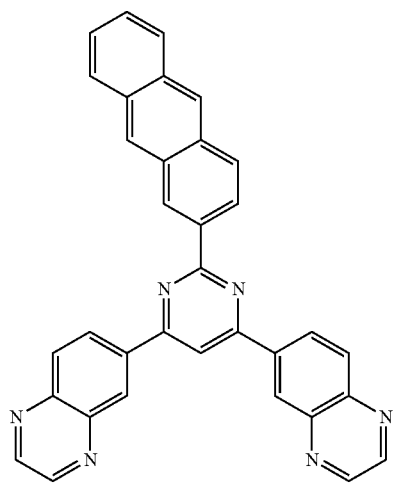
CP042
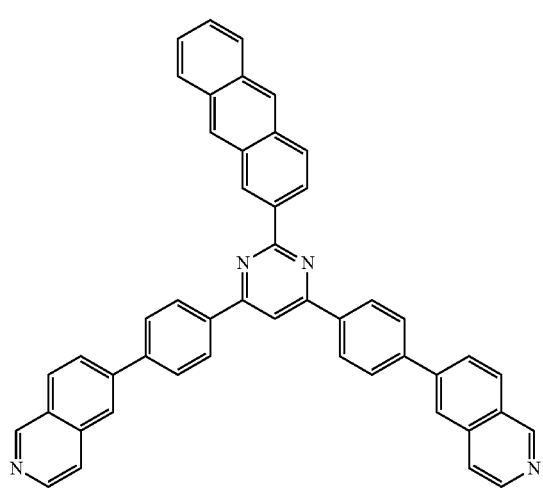
CP044
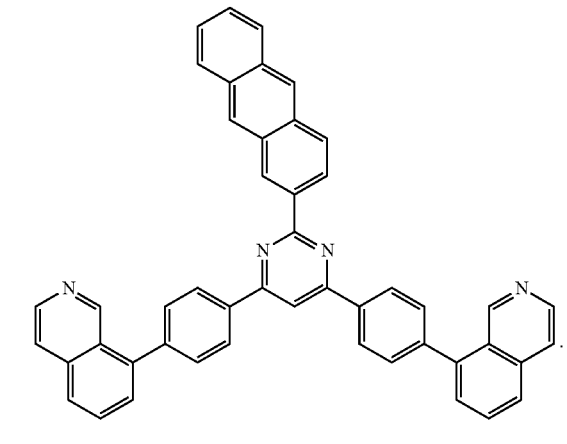
According to an embodiment of the compound of the present disclosure, in Formula 1, each of $X_1$, $X_2$, and $X_3$ is N.
According to an embodiment of the compound of the present disclosure, the organic compound is one of the following compounds:
CP006
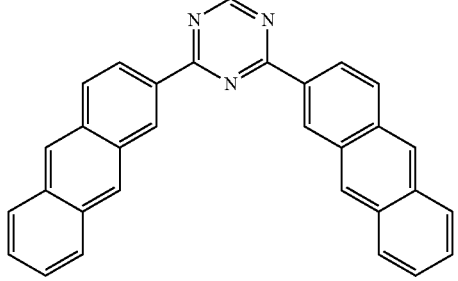
CP083

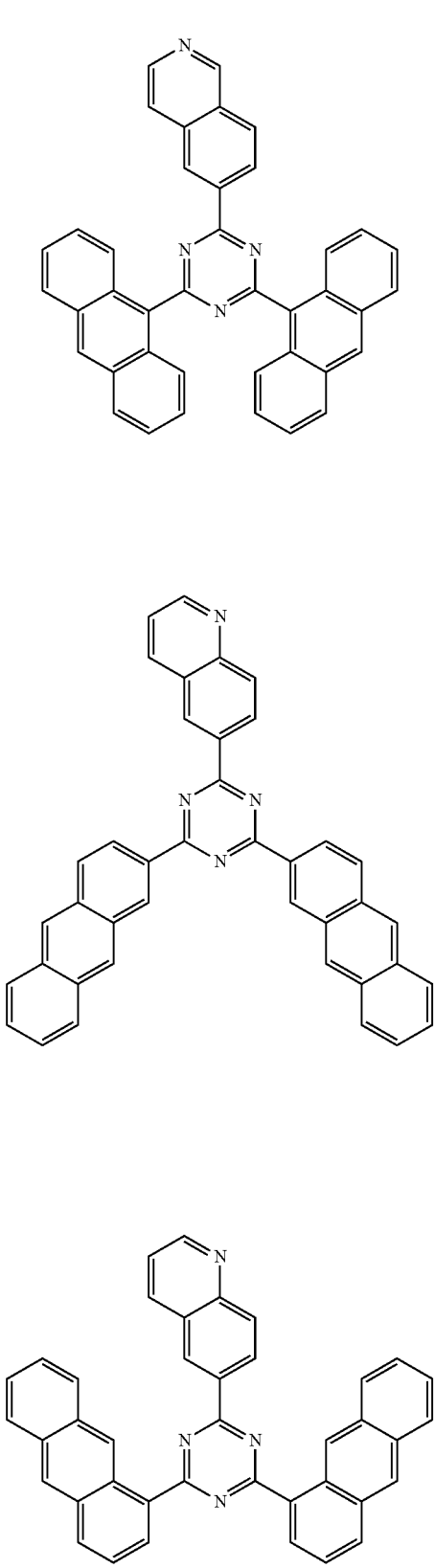
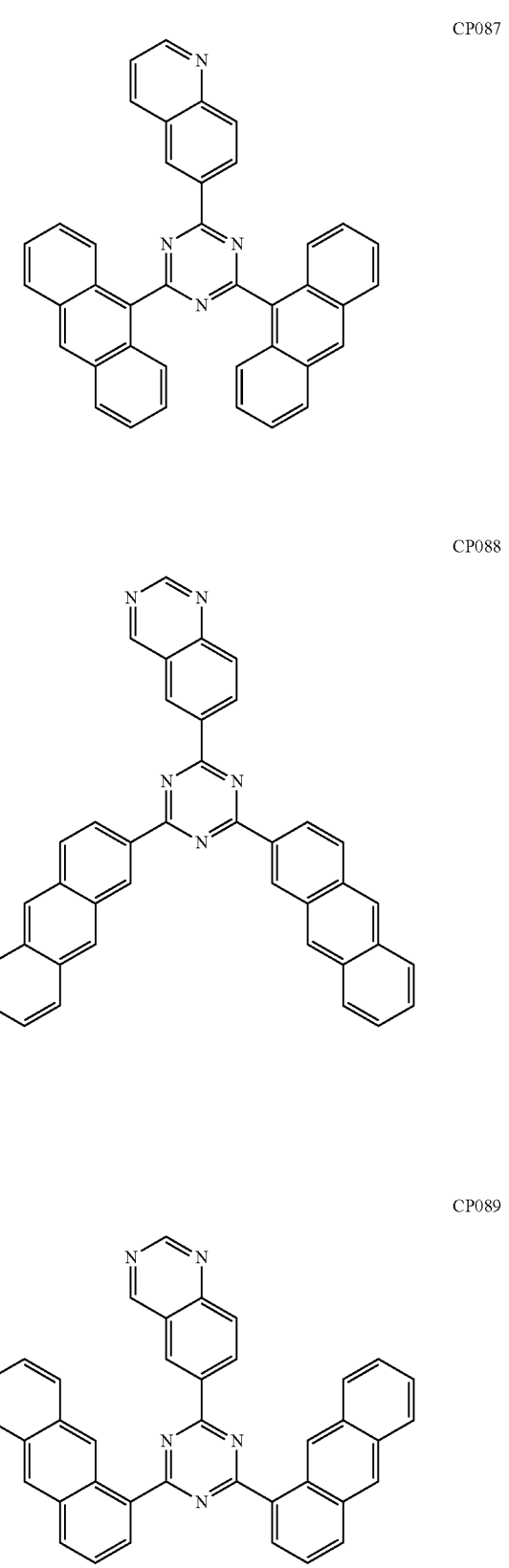

-continued
CP090
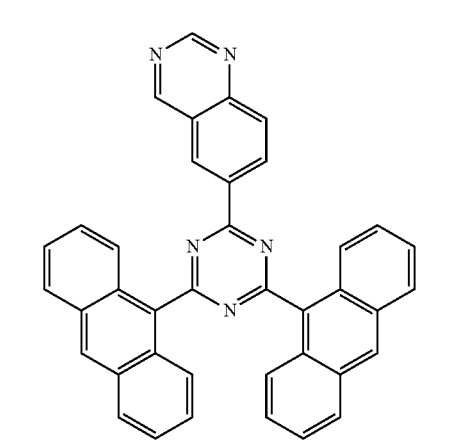
CP093
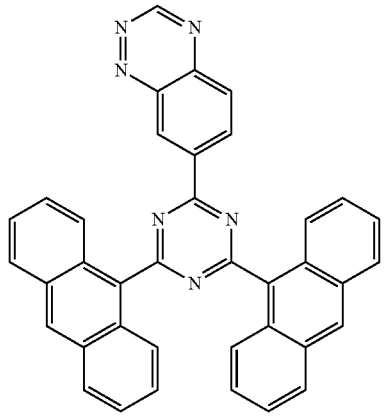
CP091
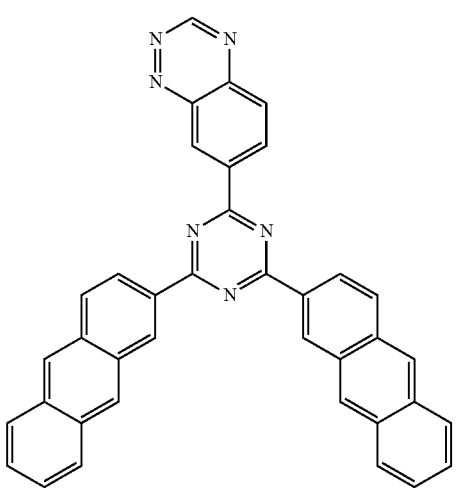
CP094
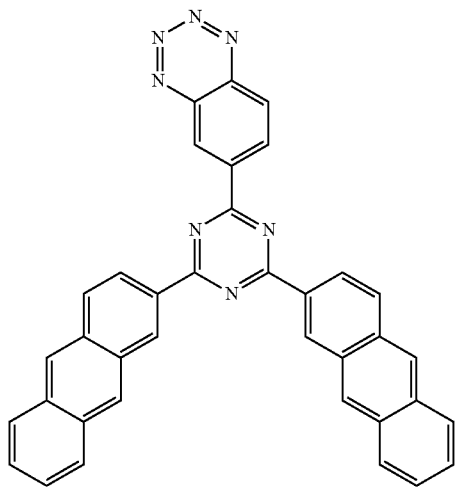
CP092
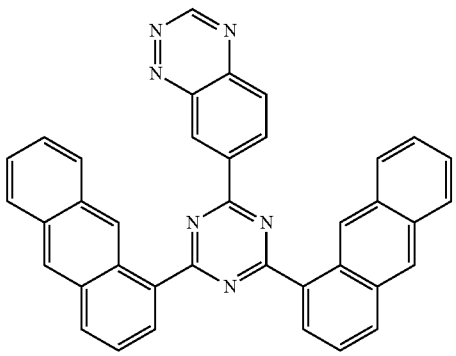
CP095
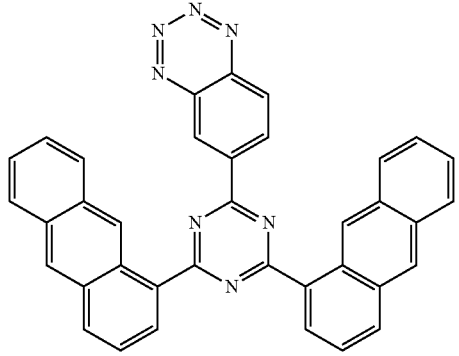

CP096
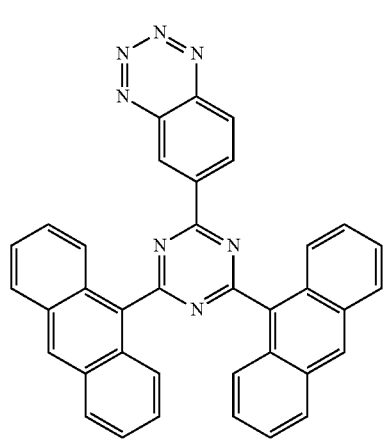
CP099
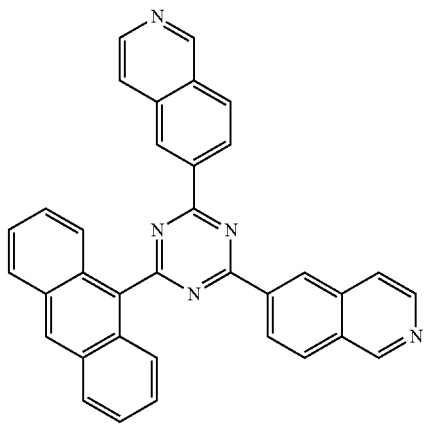
CP097
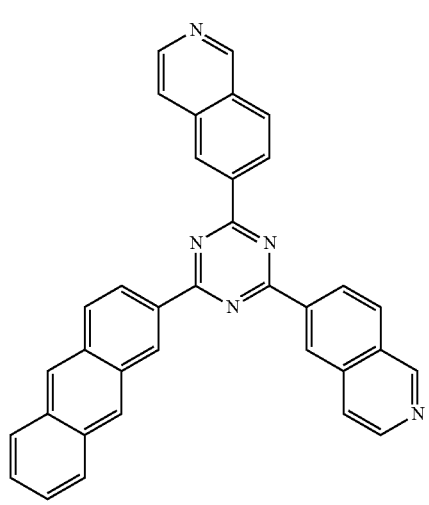
CP100
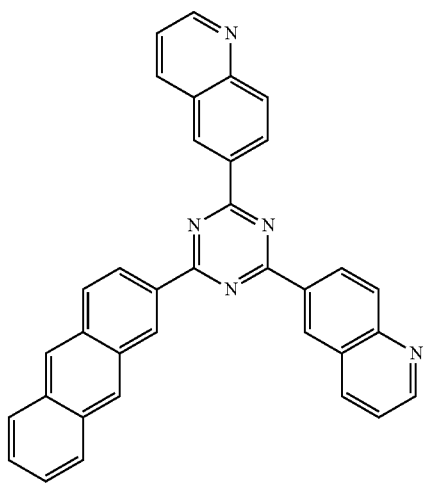
CP098
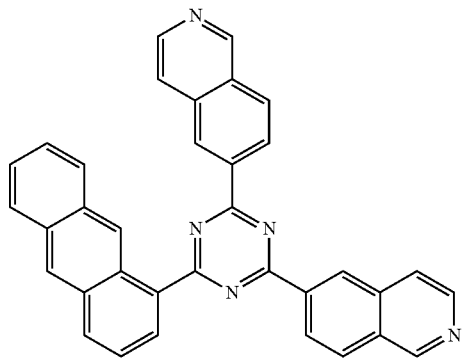
CP101
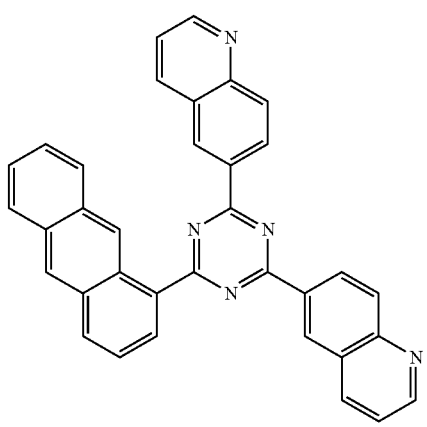

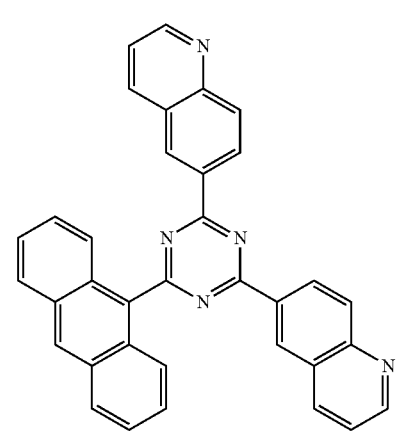
CP102
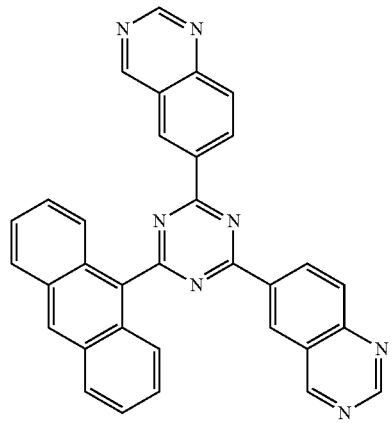
CP105
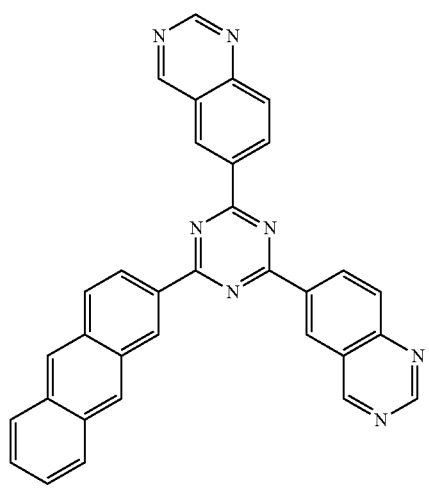
CP103
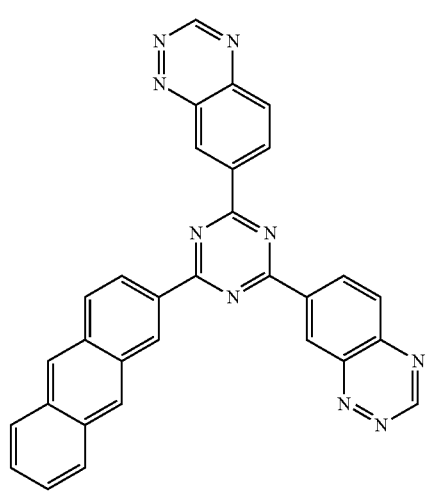
CP106
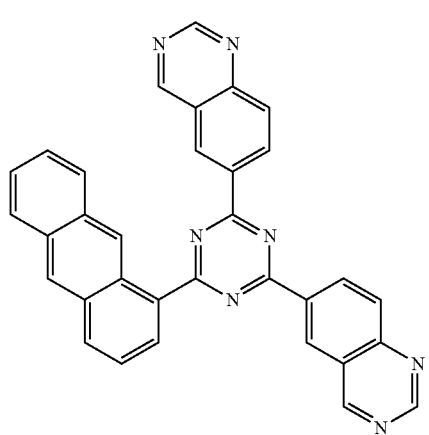
CP104
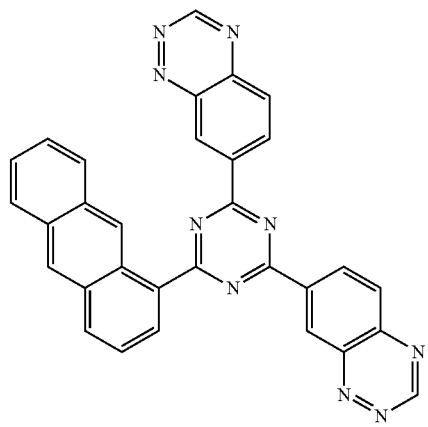
CP107

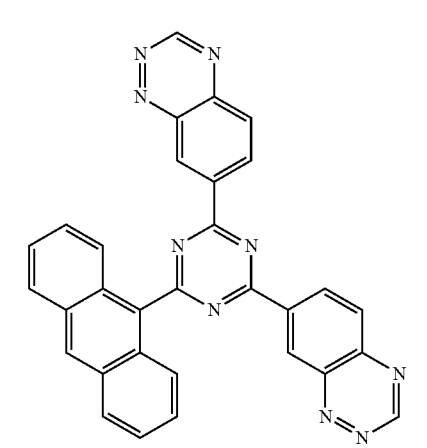
CP108
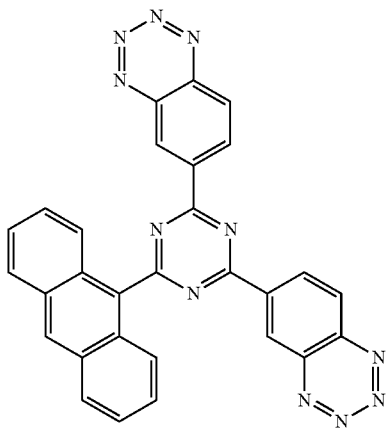
CP111
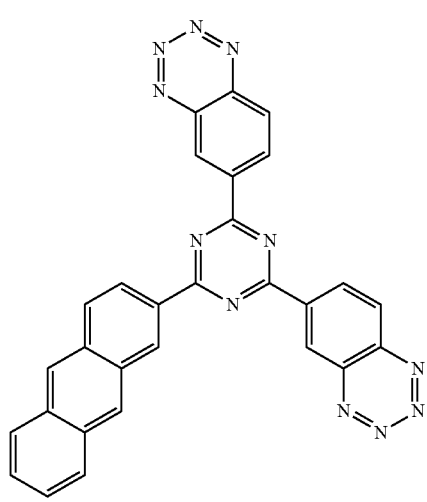
CP109
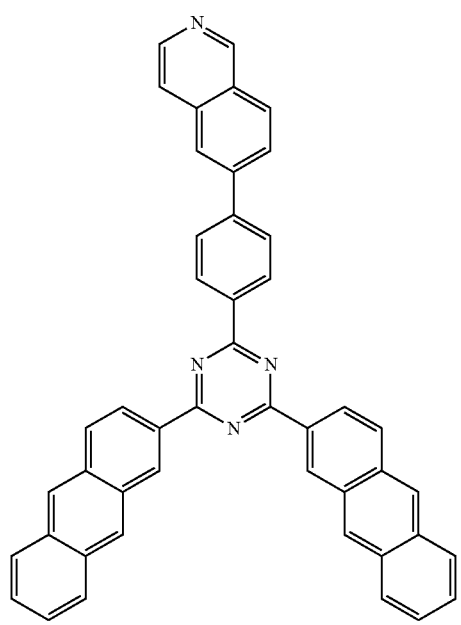
CP112
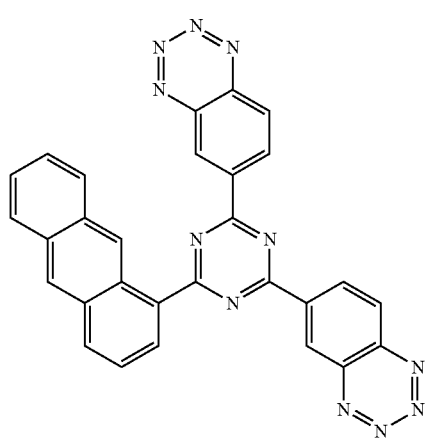
CP110
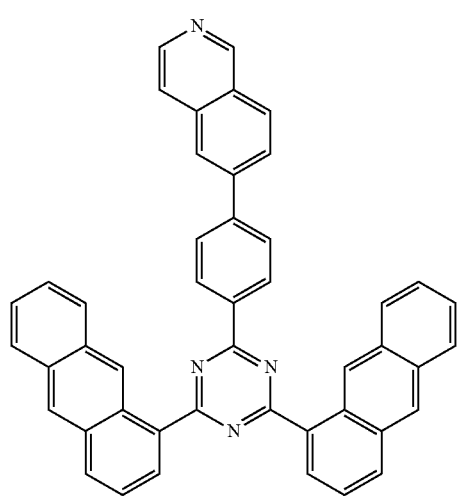
CP113

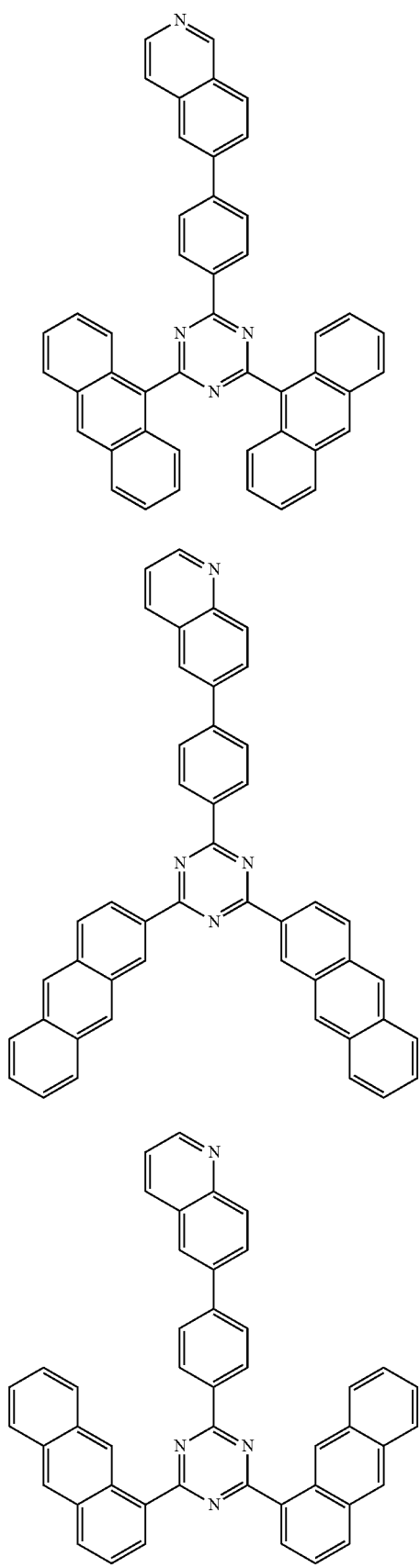
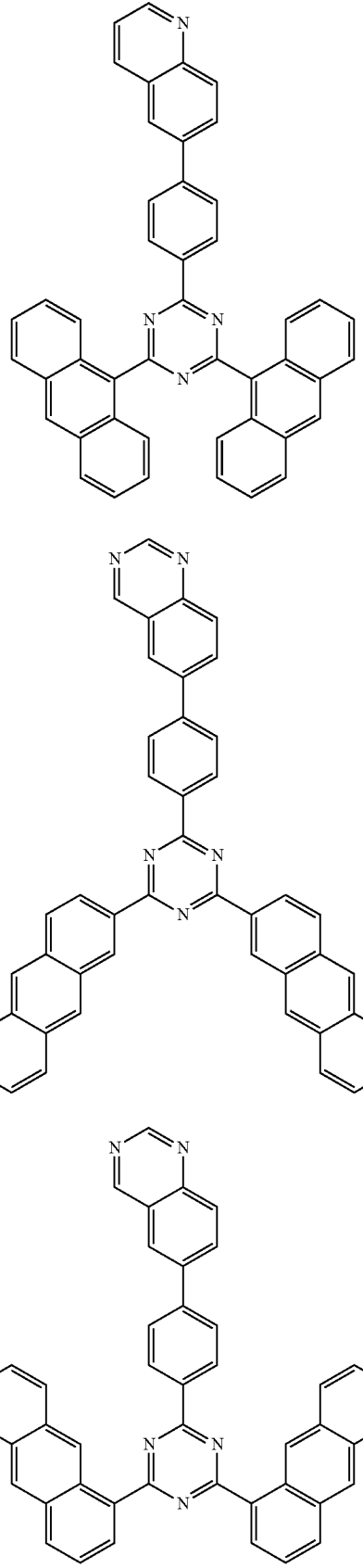

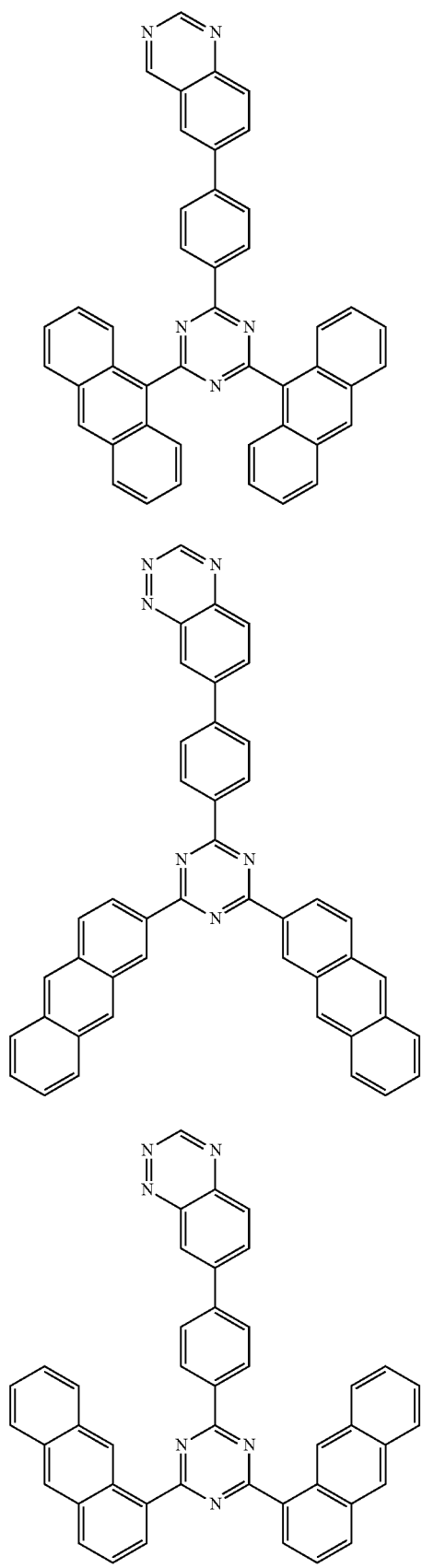
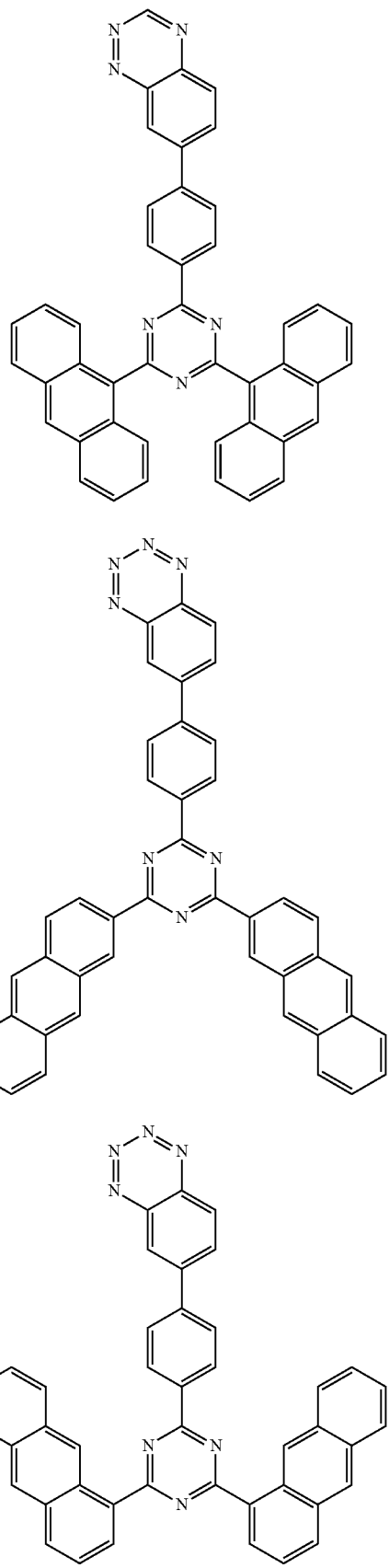

CP126
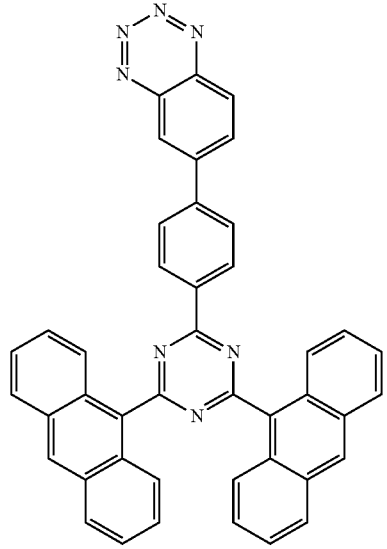
CP128
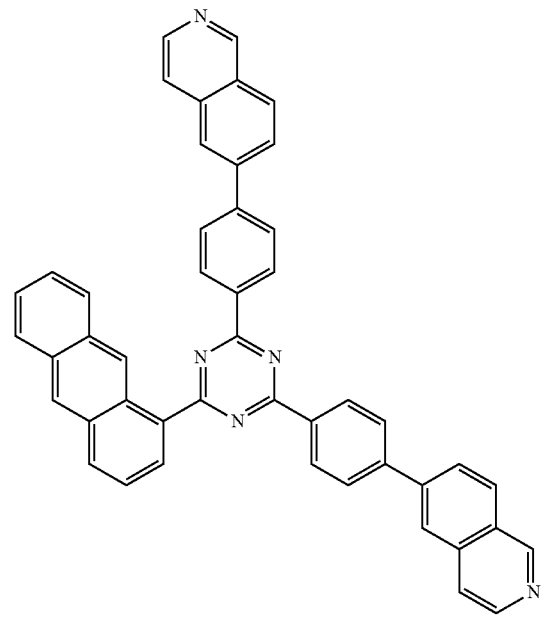
CP127
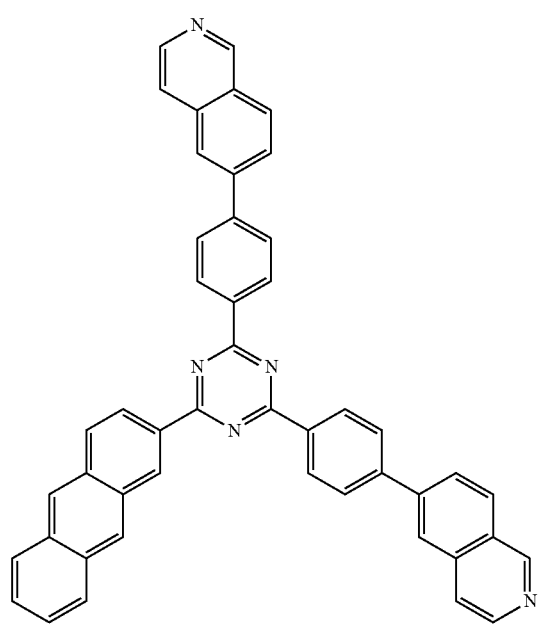
CP129
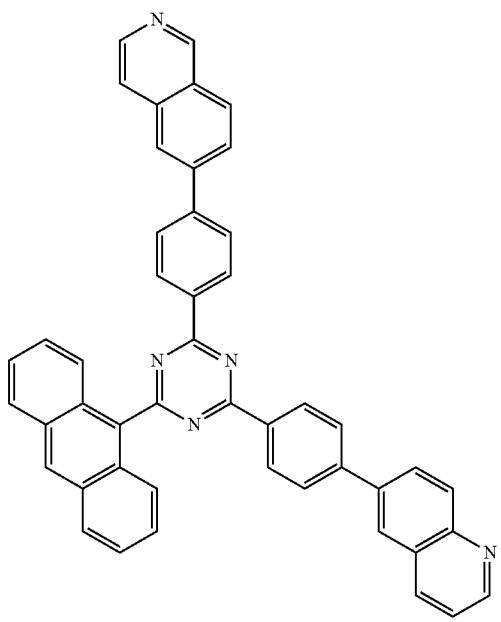

CP152
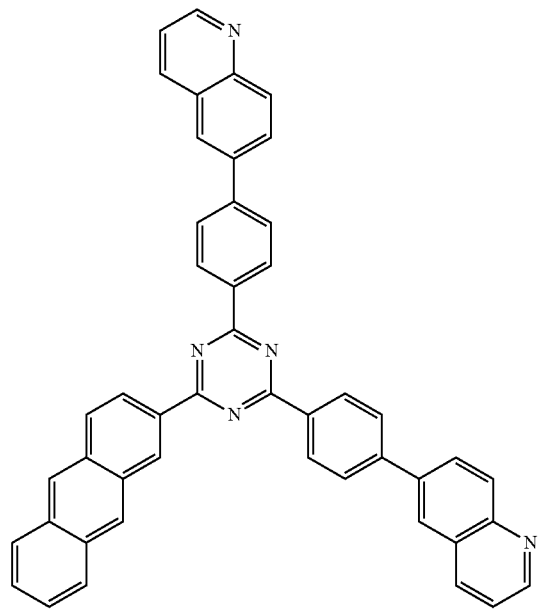
CP130
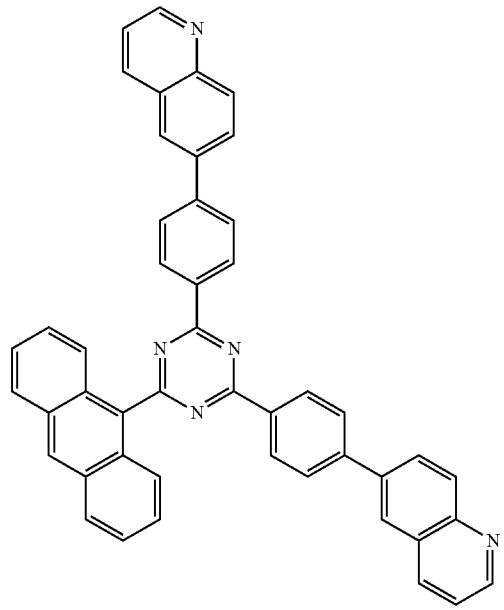
CP153
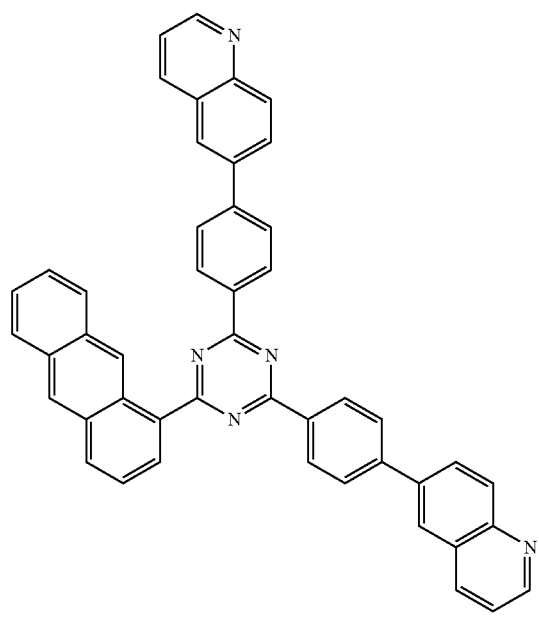
CP131
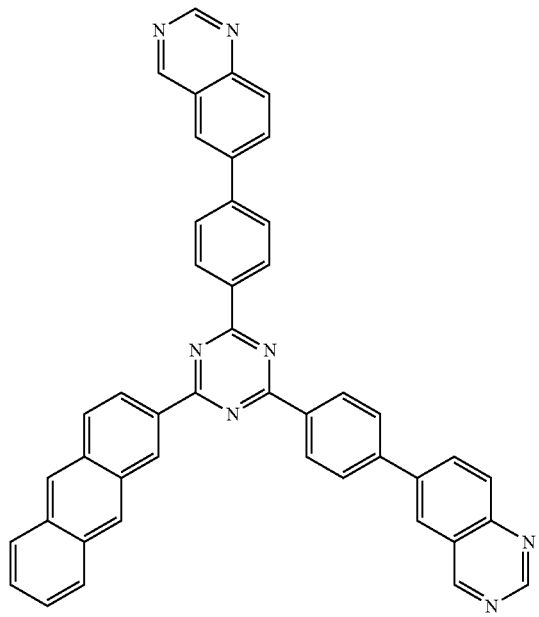

-continued
CP132
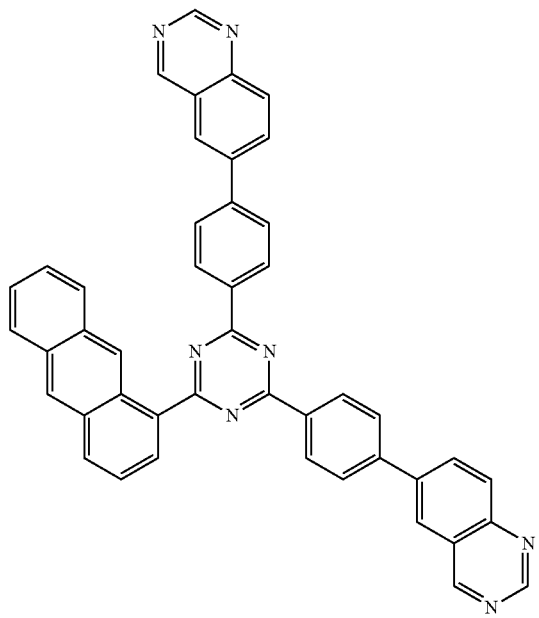
CP133
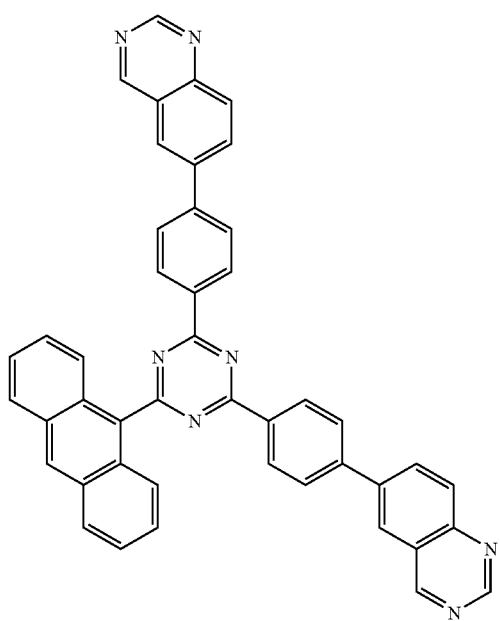
-continued
CP134
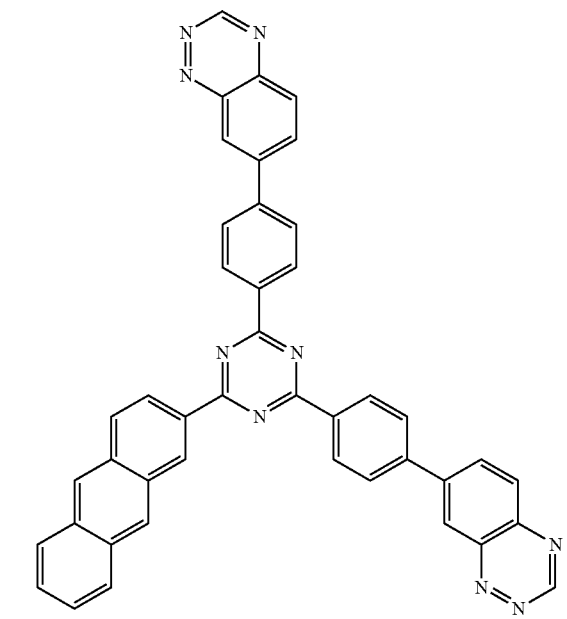
CP135
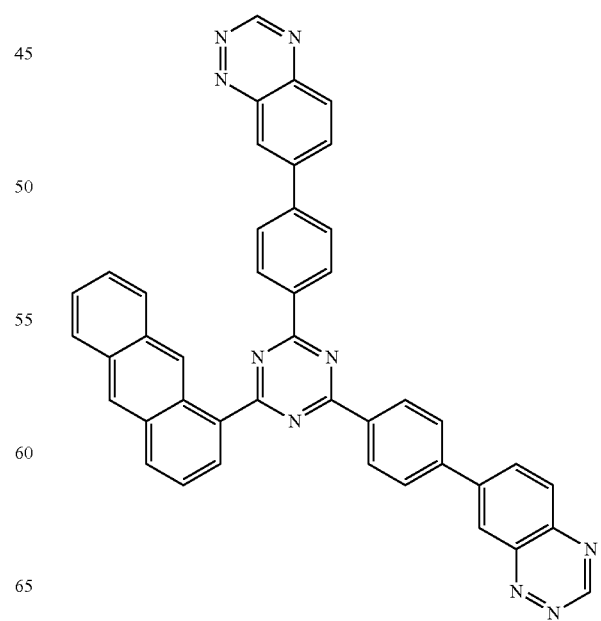

-continued
CP136
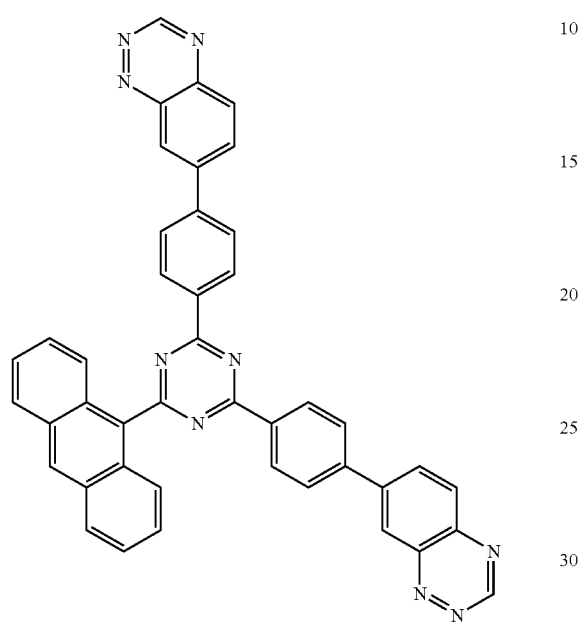
CP138
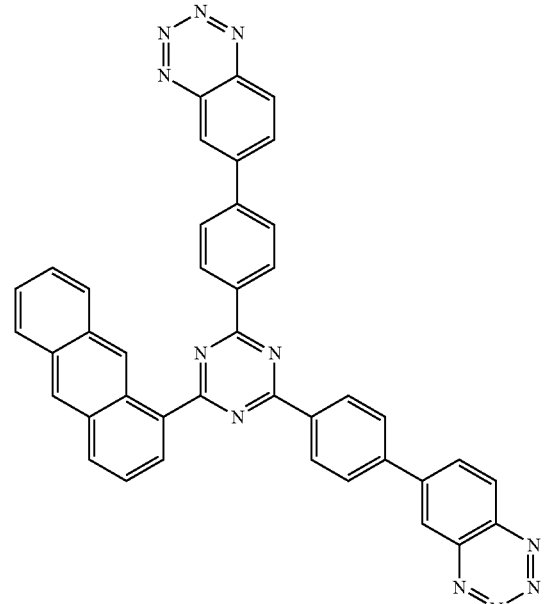
CP137
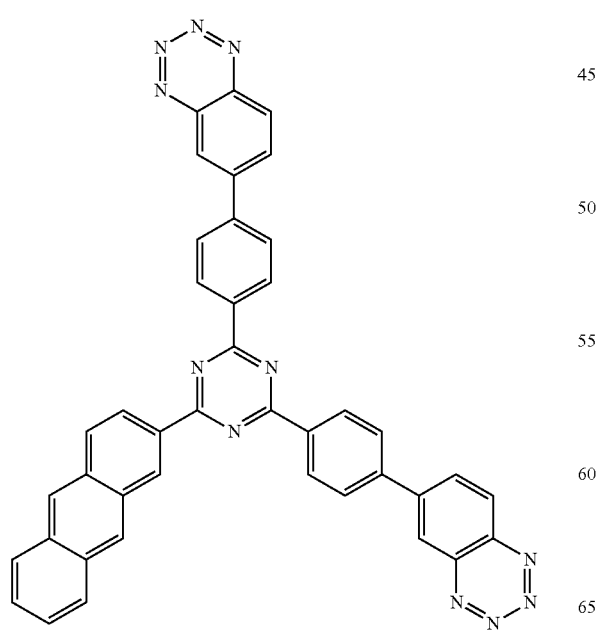
CP139
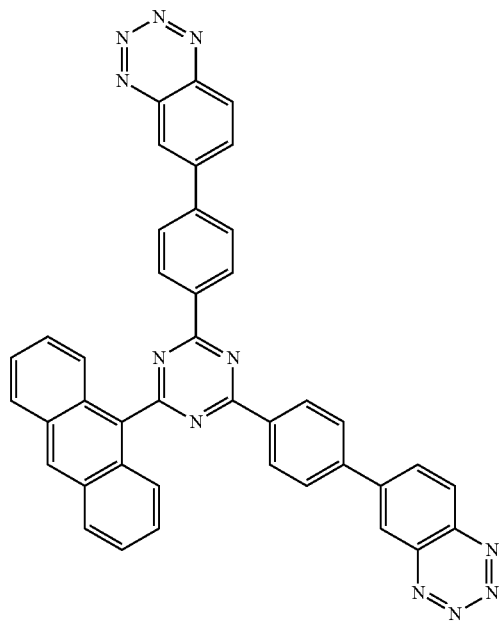

CP140
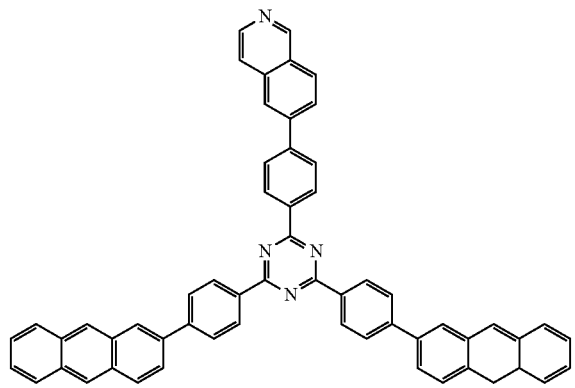
CP141
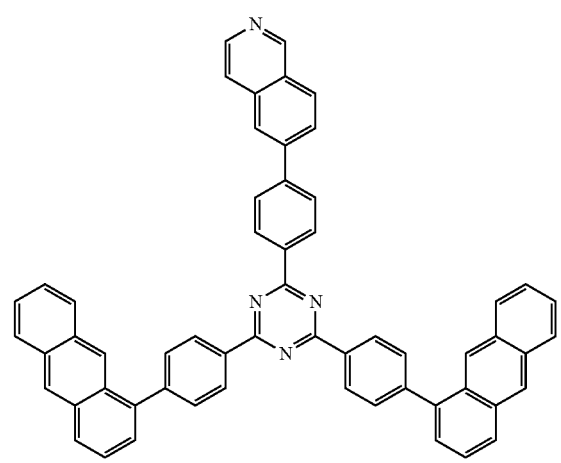
CP142
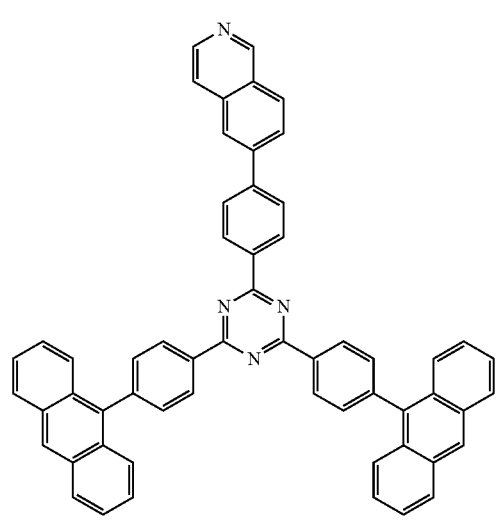
CP143
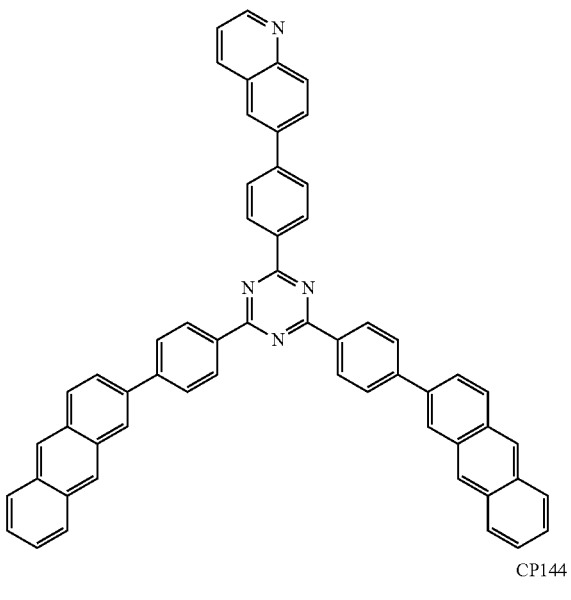
CP144
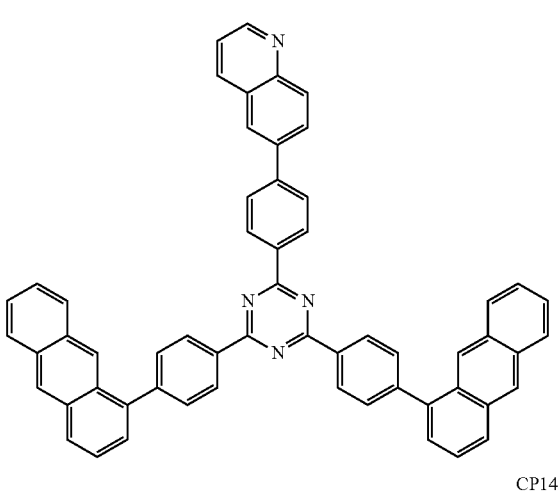
CP145
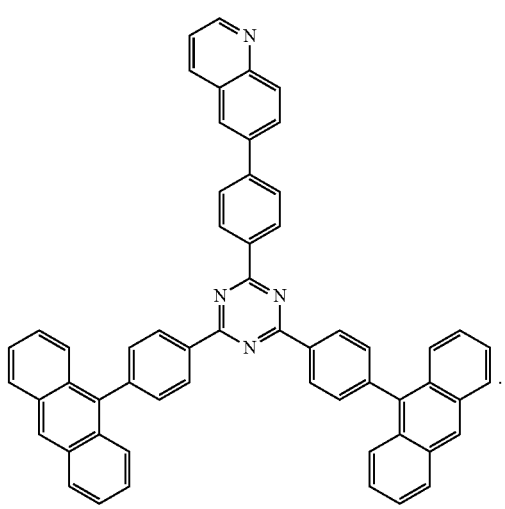
According to an embodiment of the compound of the present disclosure, the organic compound is one of the following compounds:

CP001
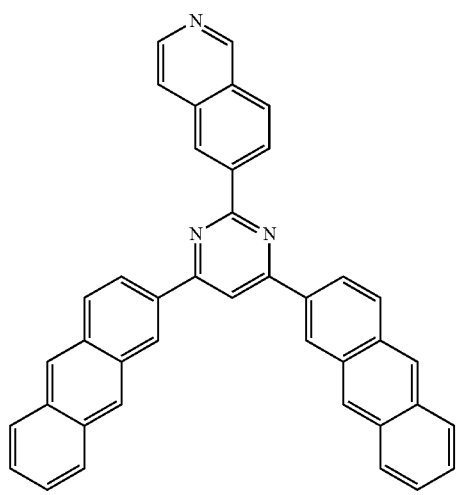
CP002
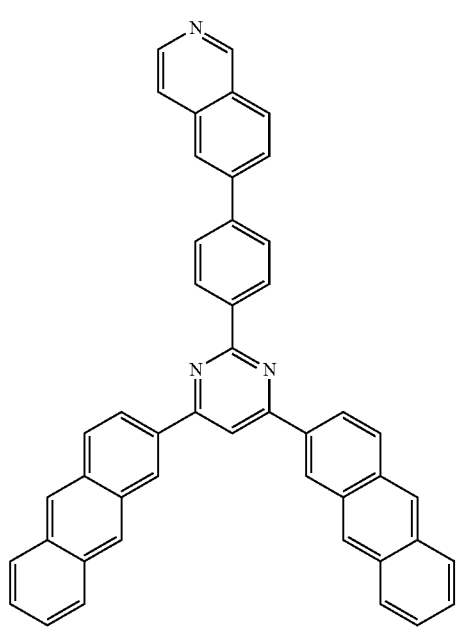
CP003
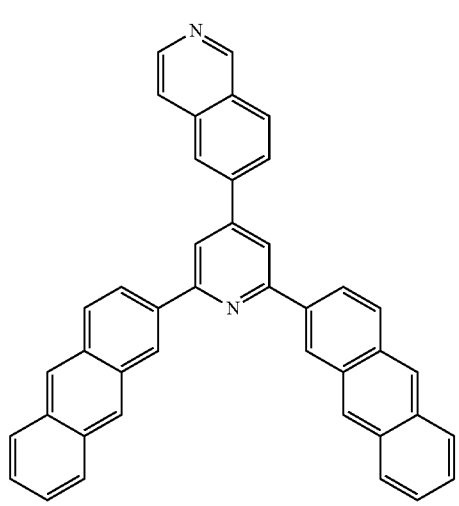
CP004
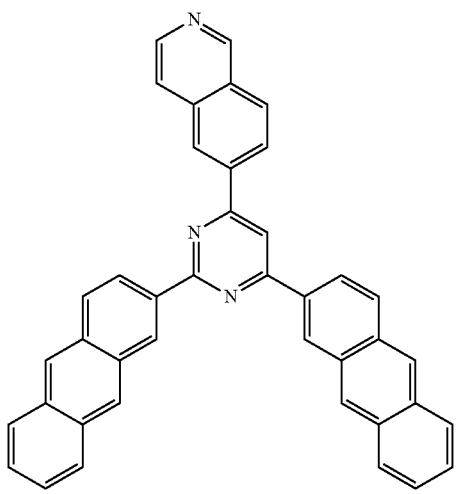
CP005
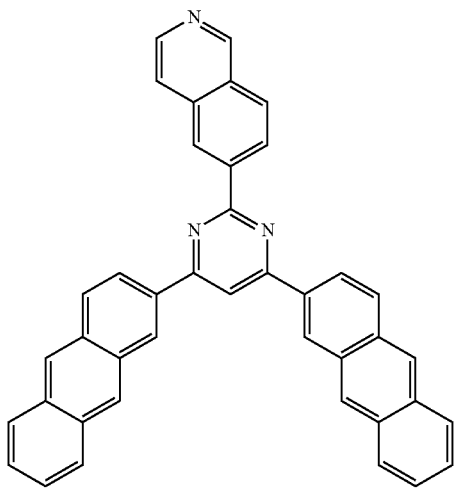
CP006
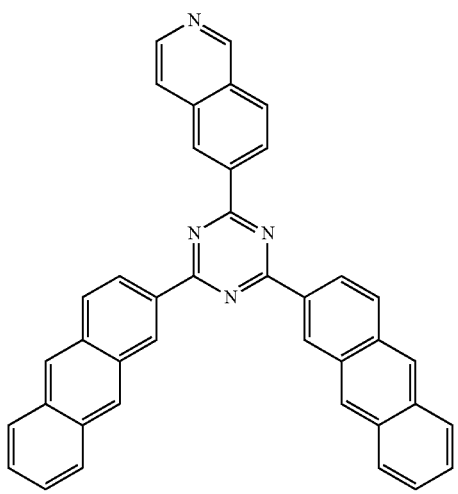

-continued
CP007
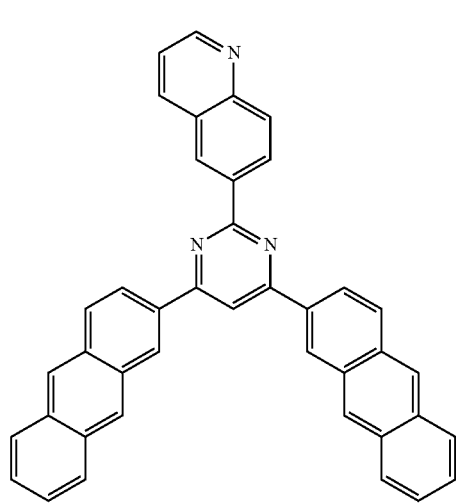
CP008
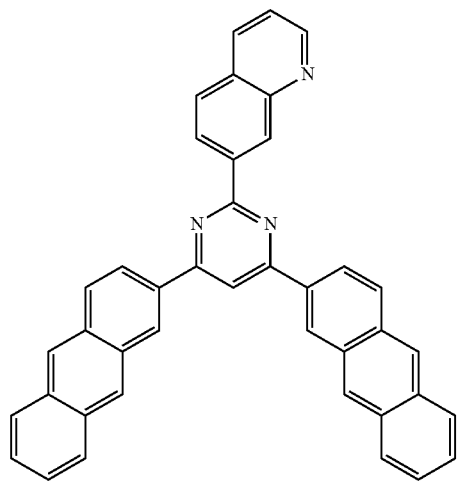
CP009
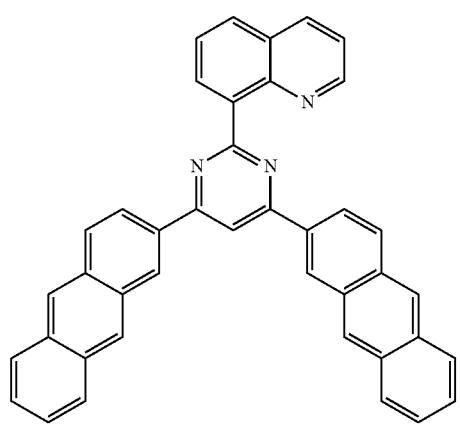
CP010
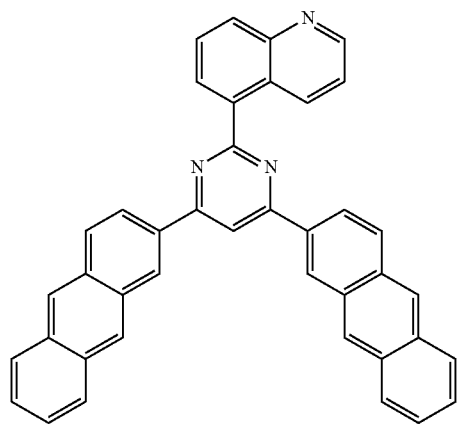
CP011
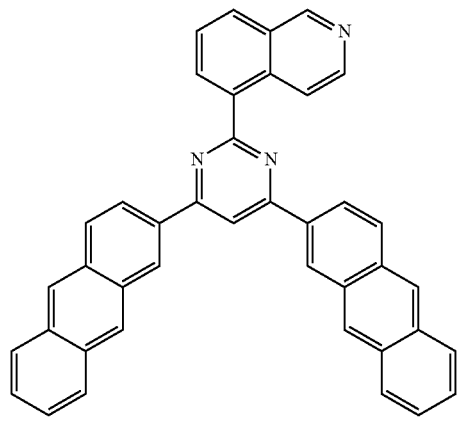
CP012
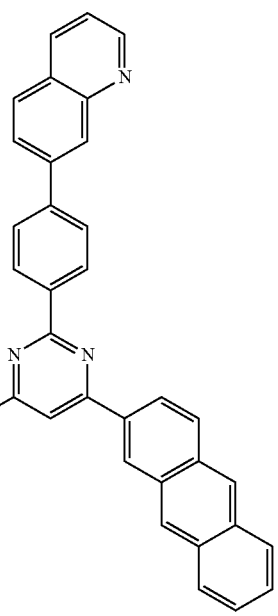

CP013
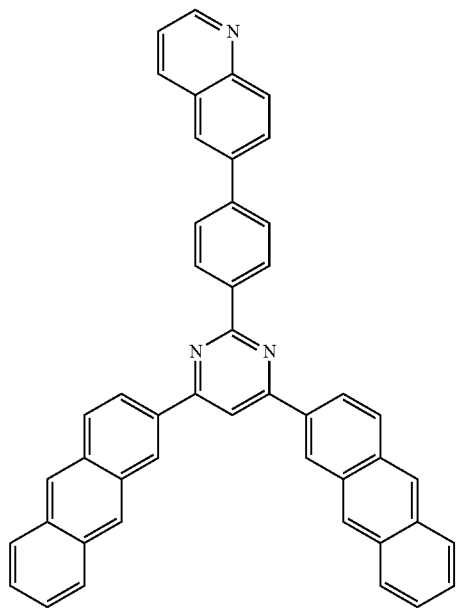
CP014
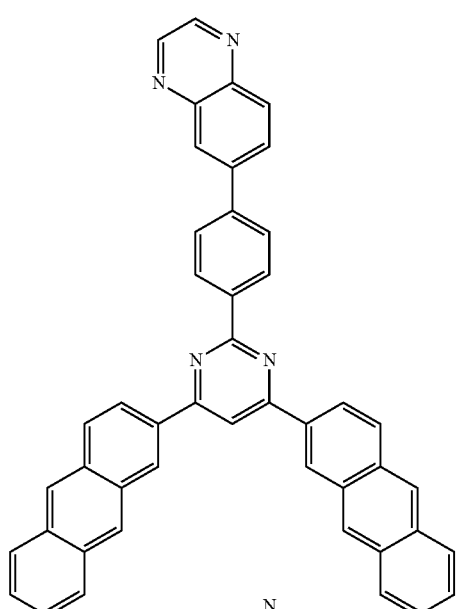
CP015
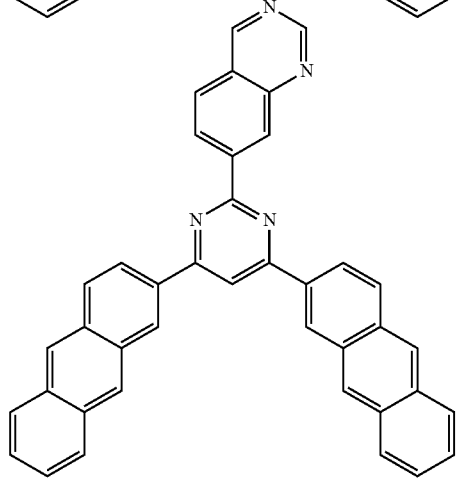
CP016
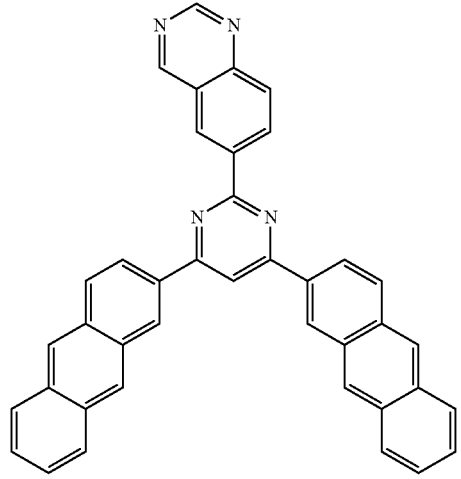
CP017
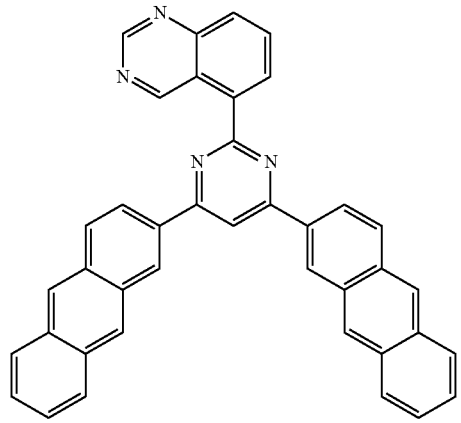
CP018
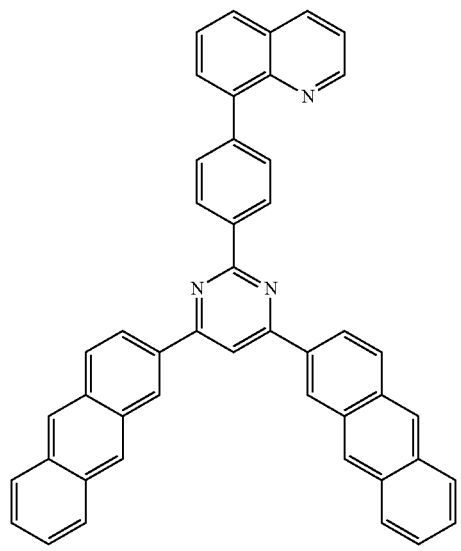

-continued
CP019
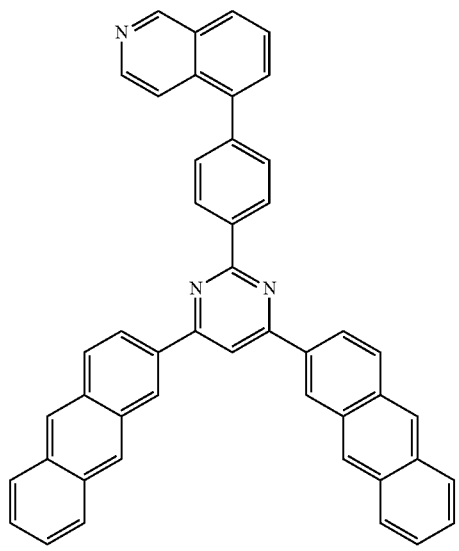
CP020
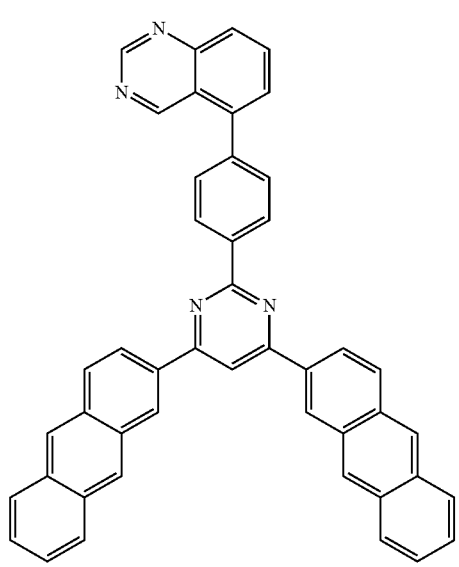
CP021
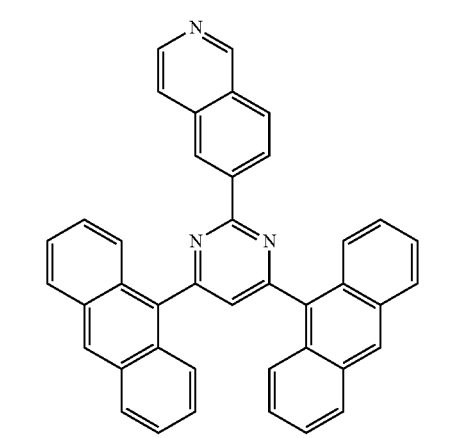
-continued
CP022
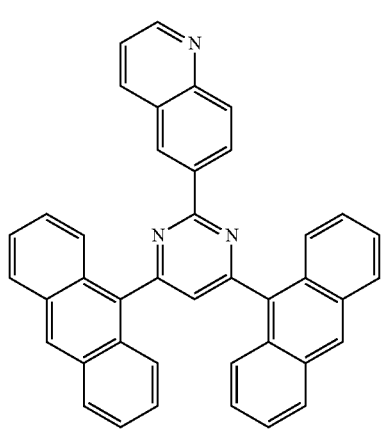
CP023
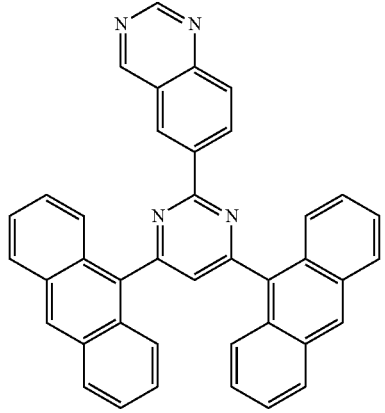
CP024
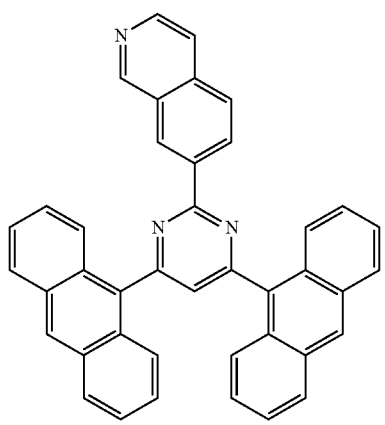

-continued
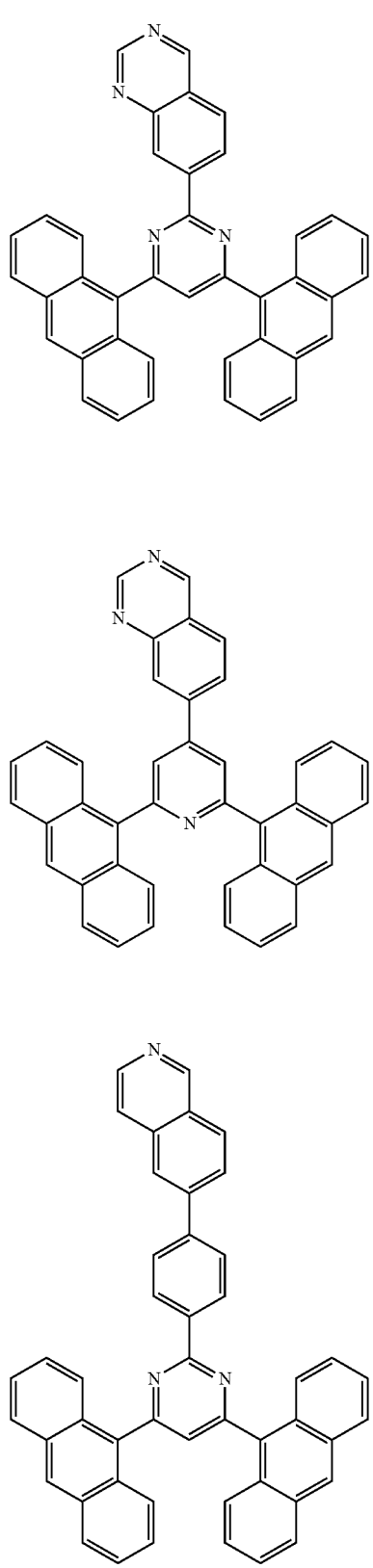
CP025
CP026
CP027
-continued
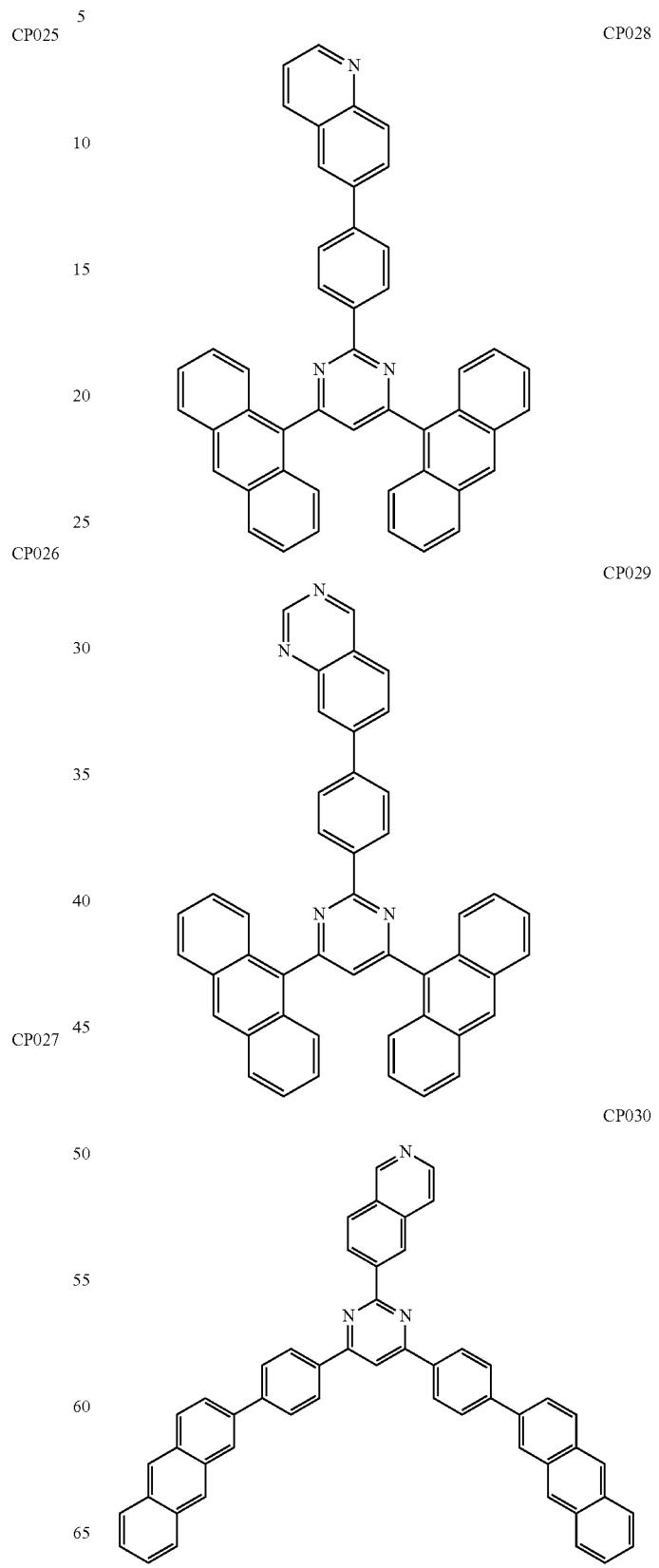
CP028
CP029
CP030

CP031
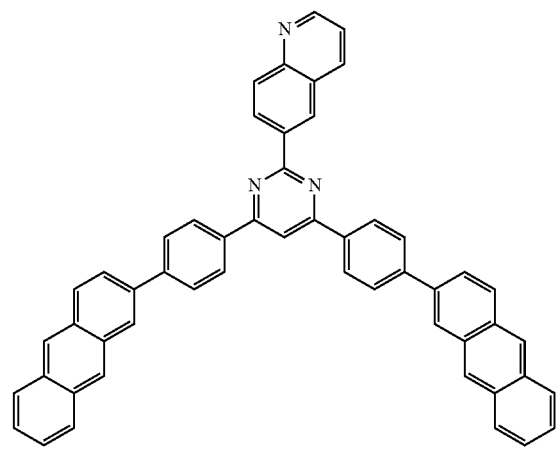
CP032
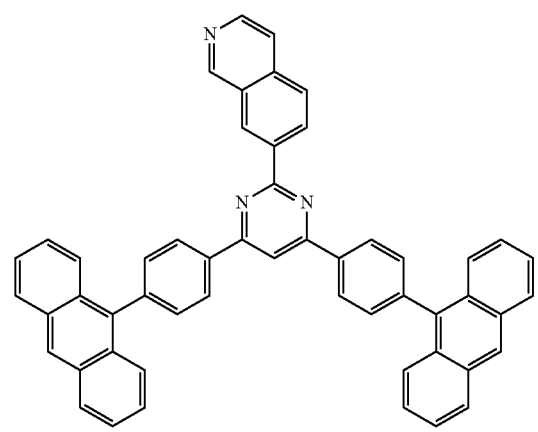
CP033
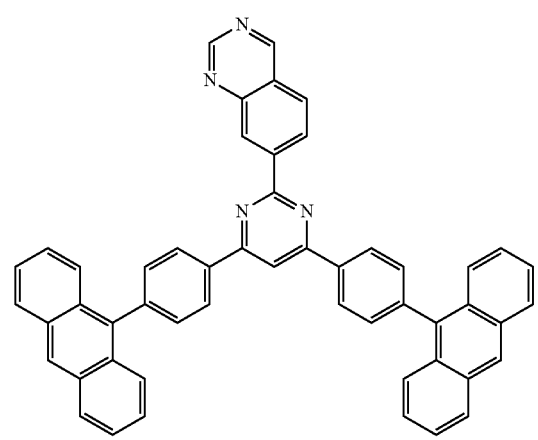
CP034
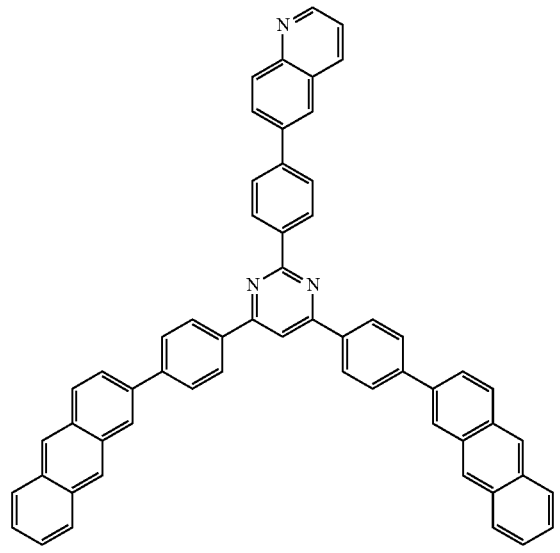
CP035
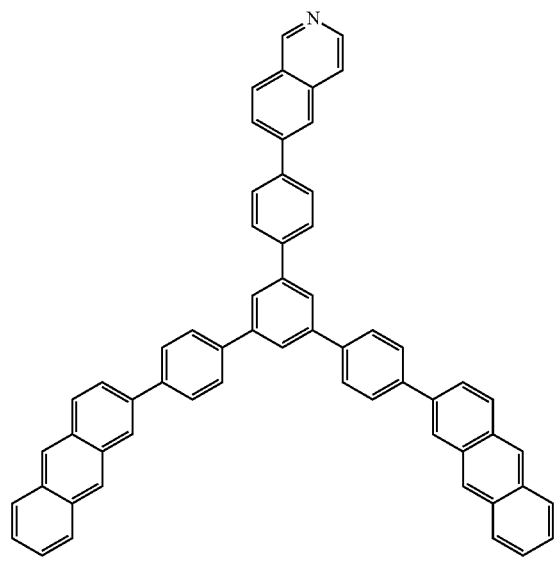
CP036
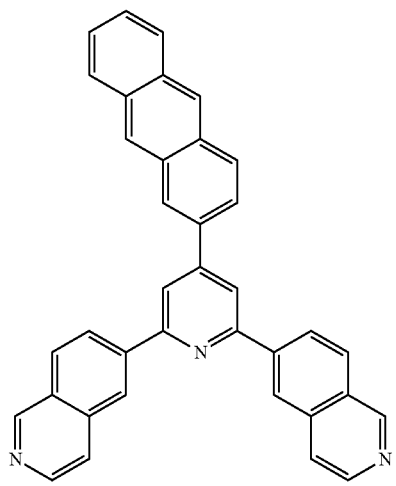

CP037
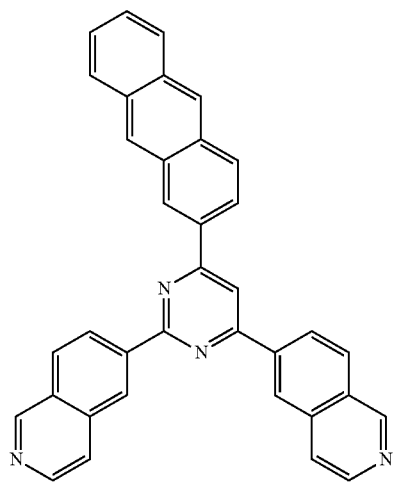
CP038
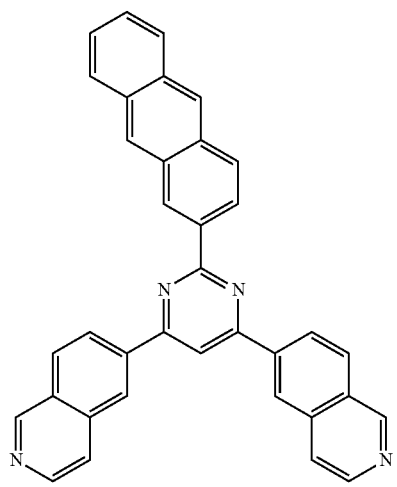
CP039
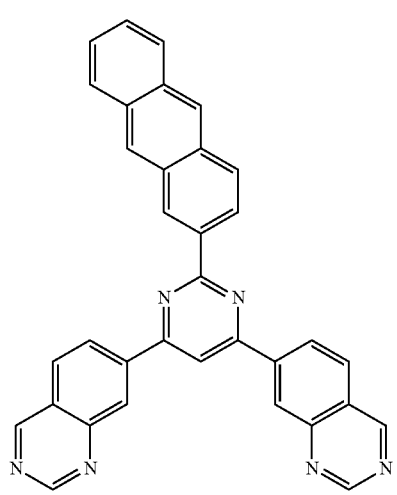
CP040
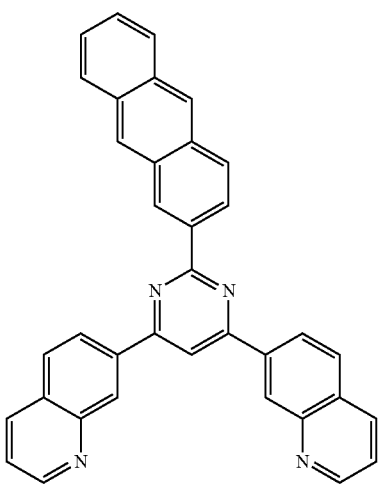
CP041
CP042
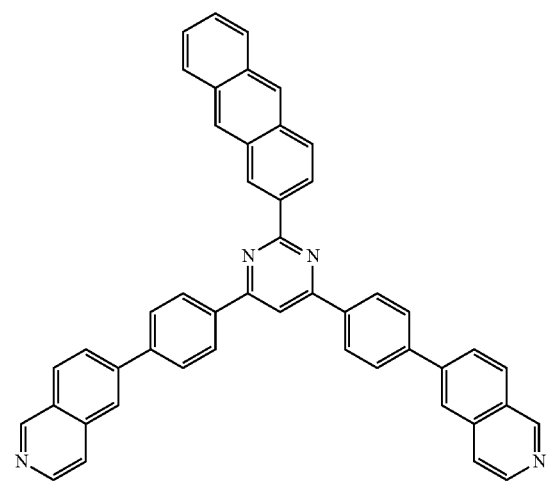

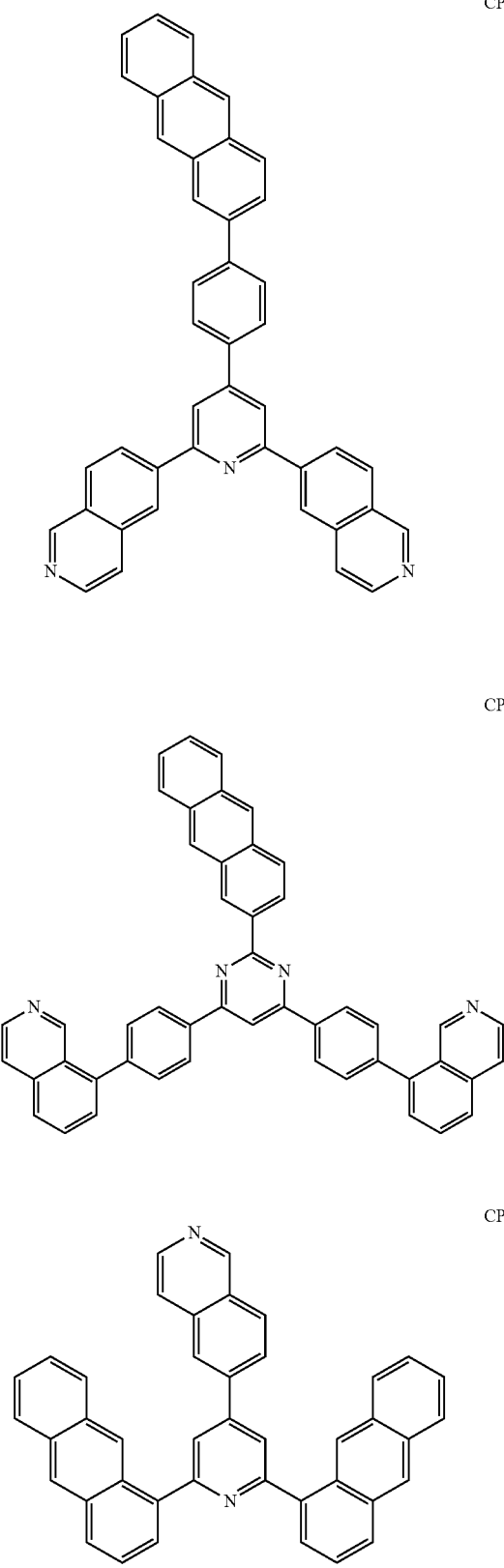
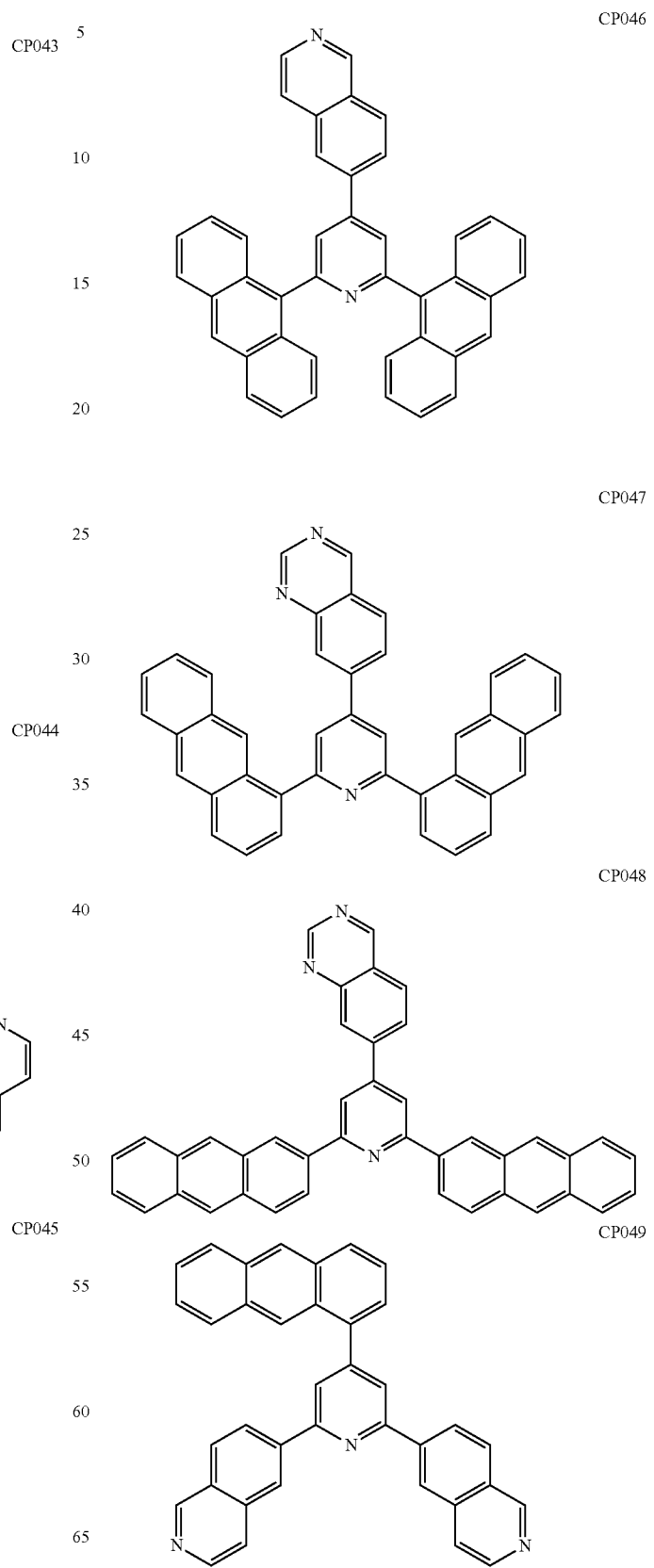

-continued
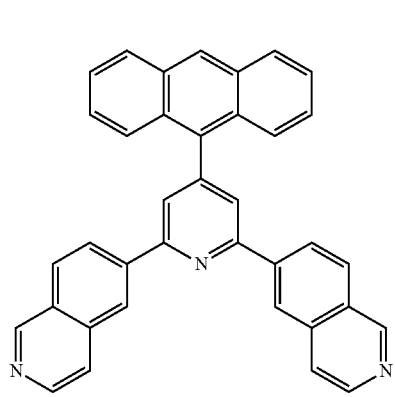
CP050
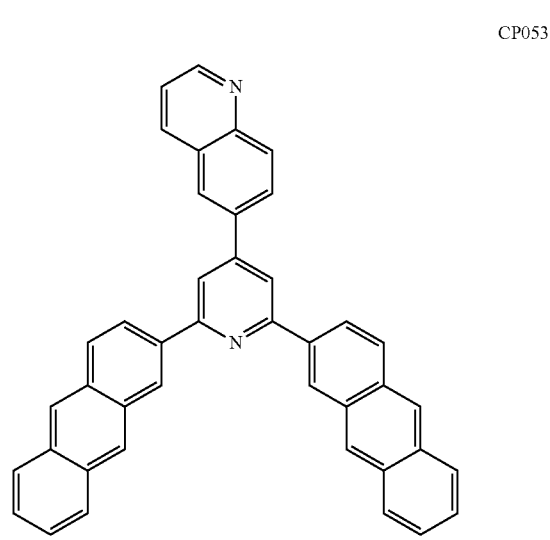
CP053
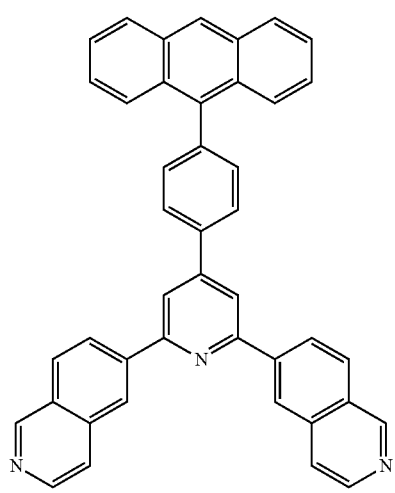
CP051
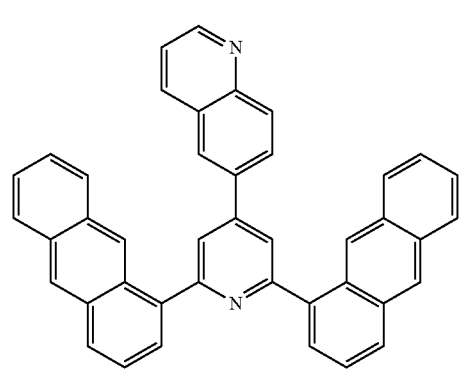
CP054
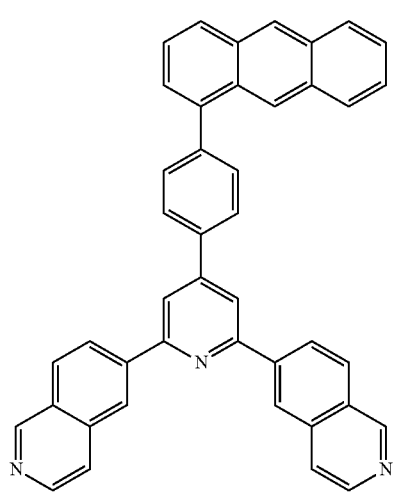
CP052
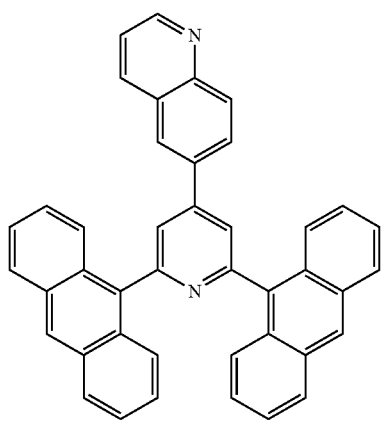
CP055

CP056
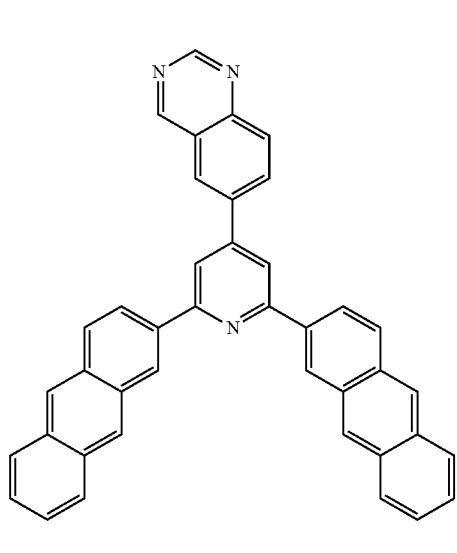
CP059
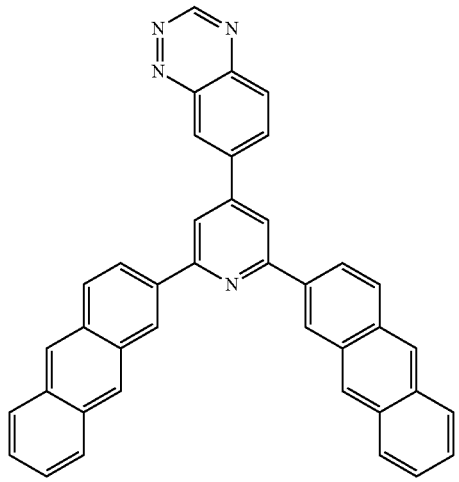
CP057
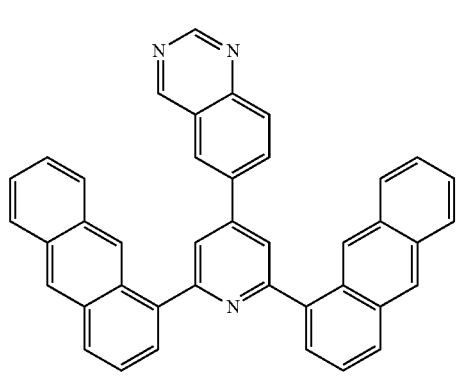
CP060
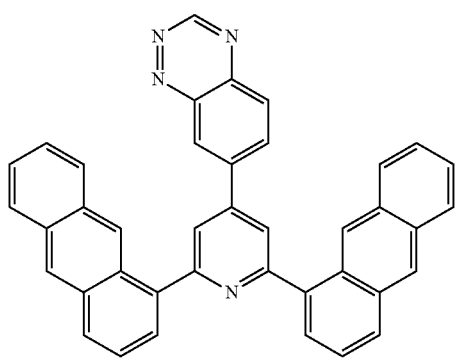
CP058
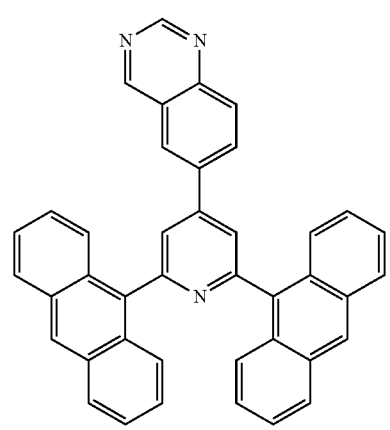
CP061
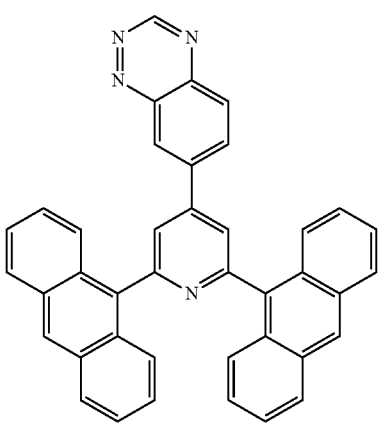

CP062
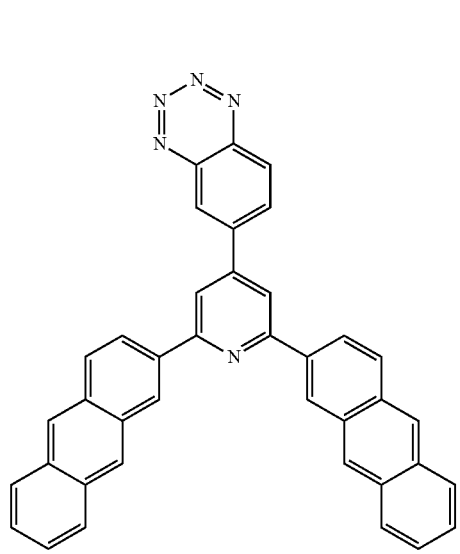
CP065
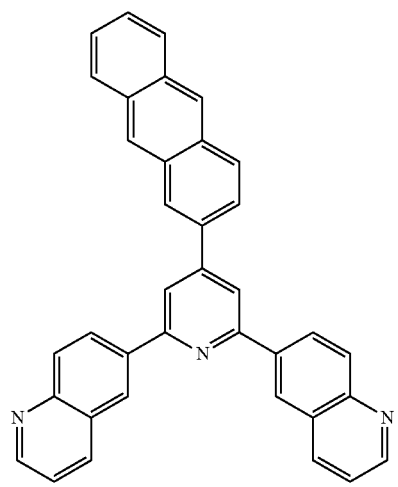
CP063
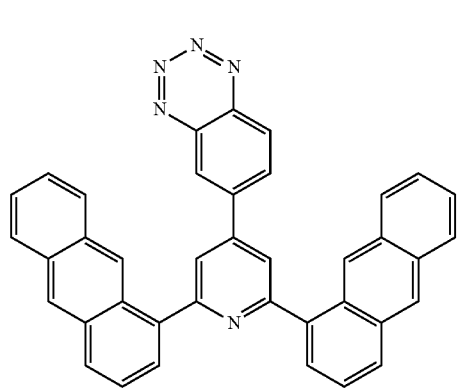
CP066
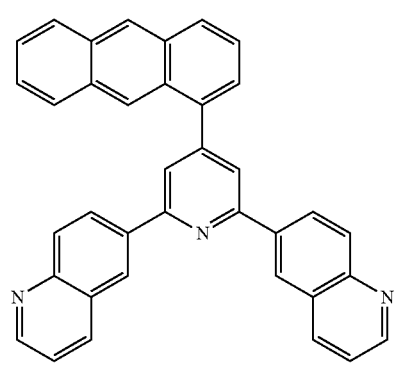
CP064
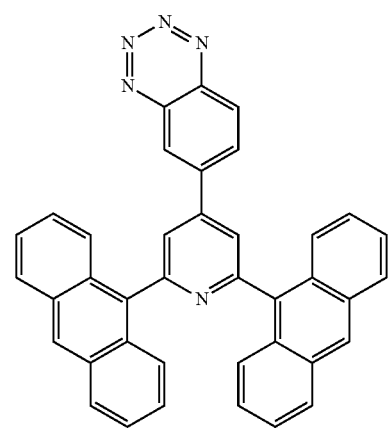
CP067
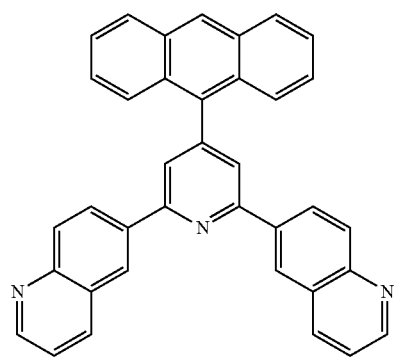

CP068
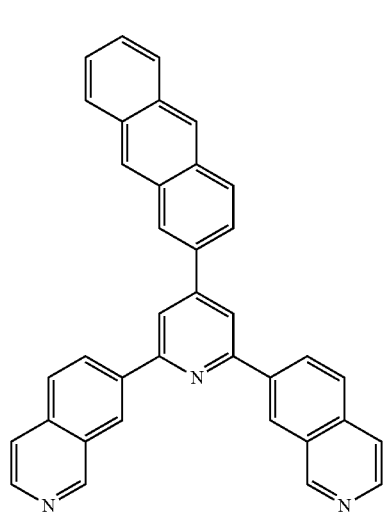
CP071
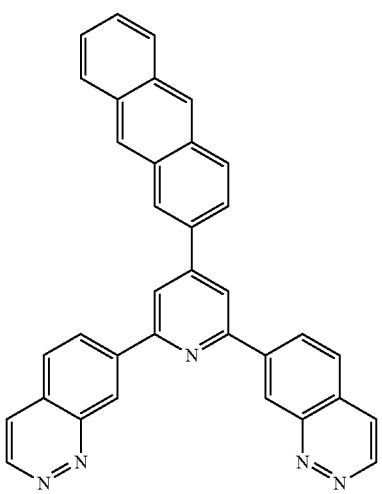
CP069
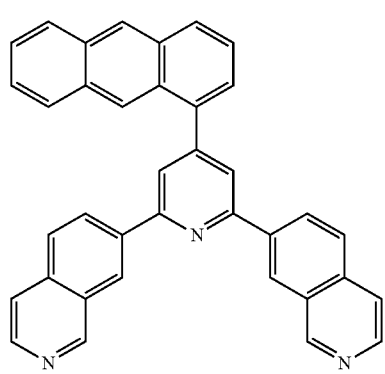
CP072
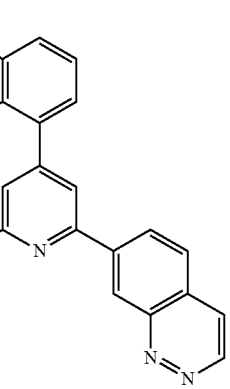
CP070
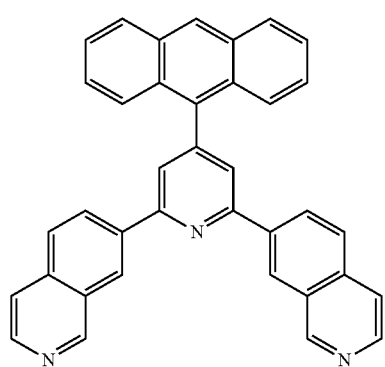
CP073
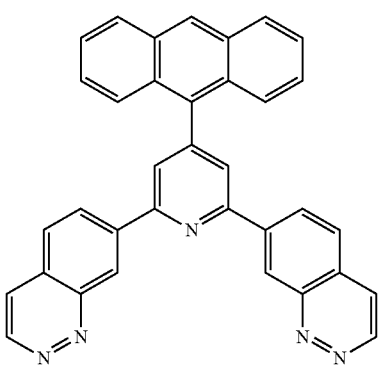

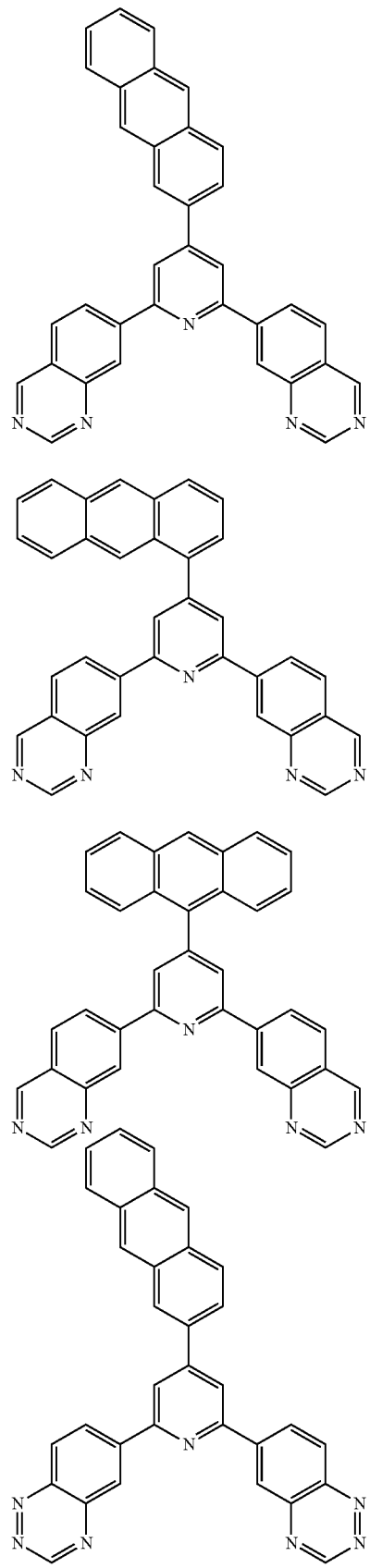
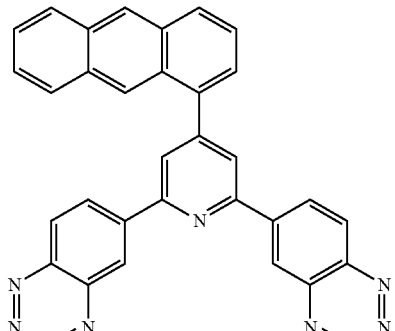
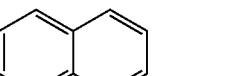
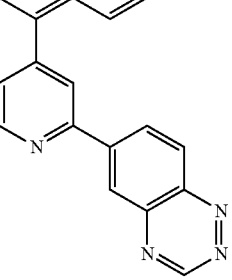
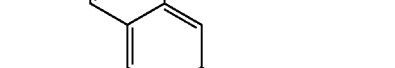
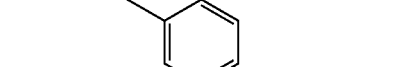
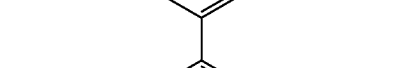
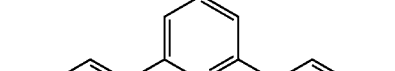
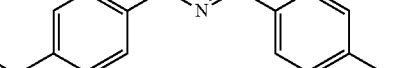

-continued
CP082
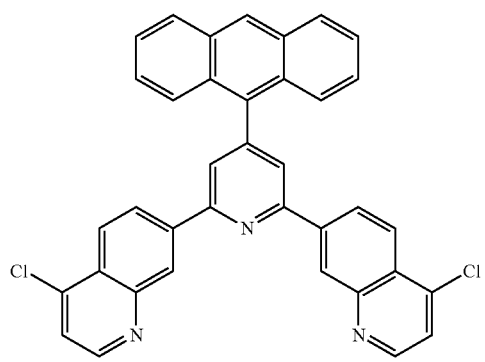
CP083
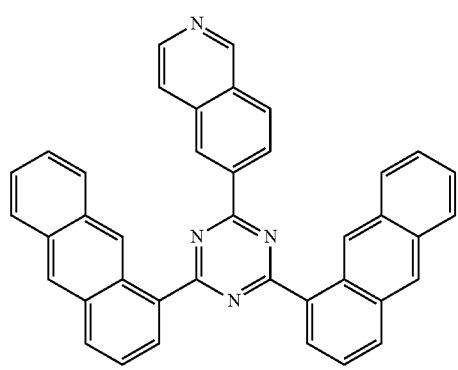
CP084
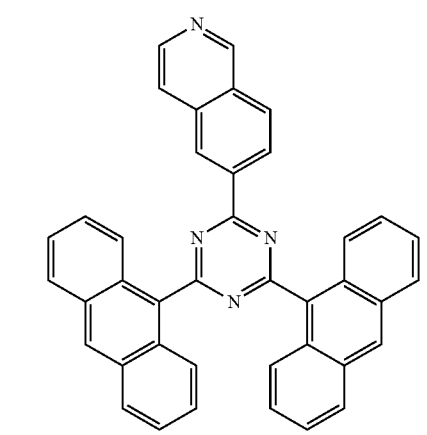
CP085
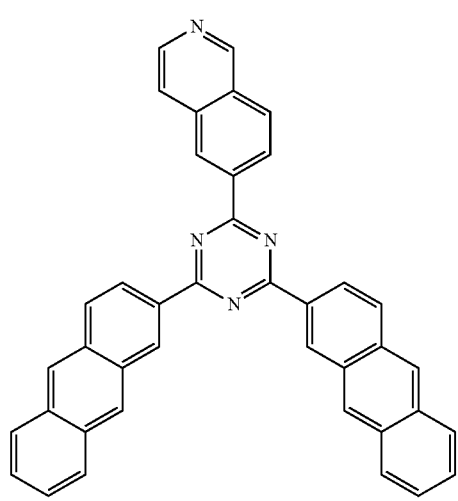
CP086
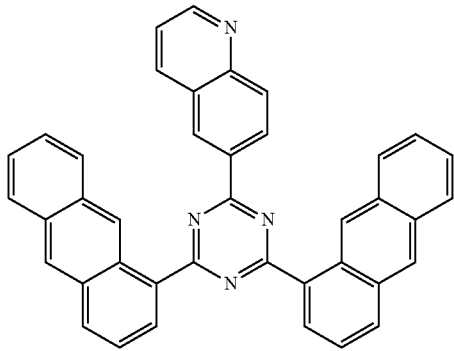
CP087
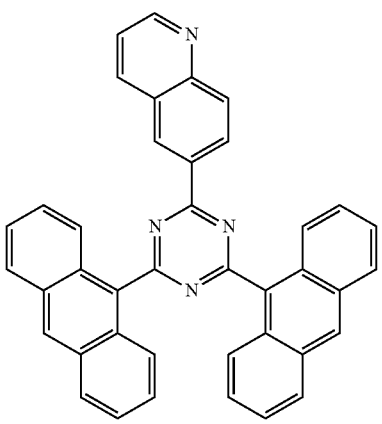
CP088
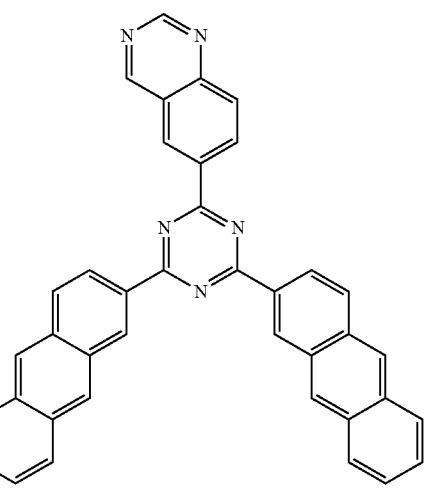
CP089
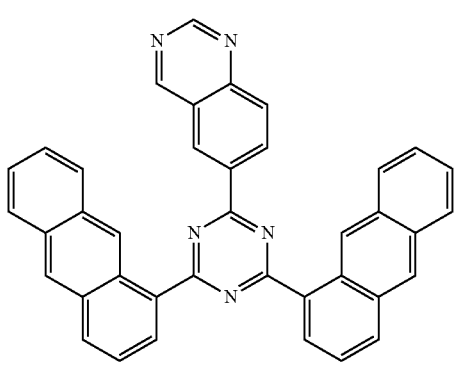

-continued
CP090
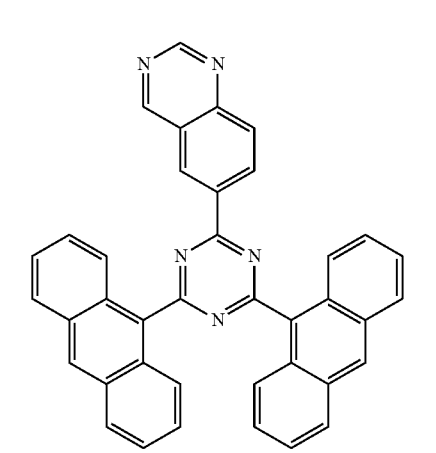
CP091
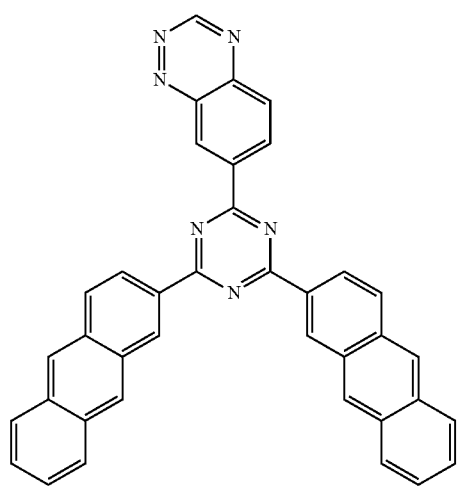
CP092
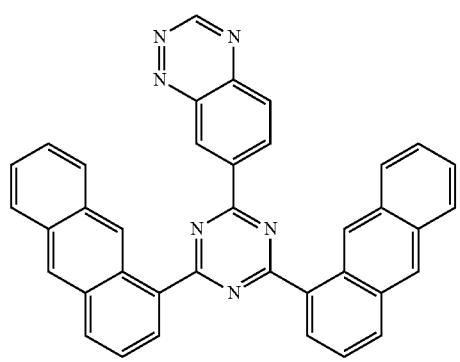
-continued
CP093
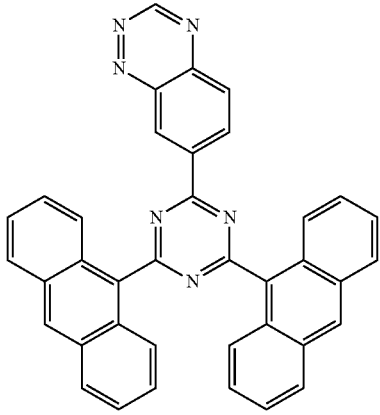
CP094
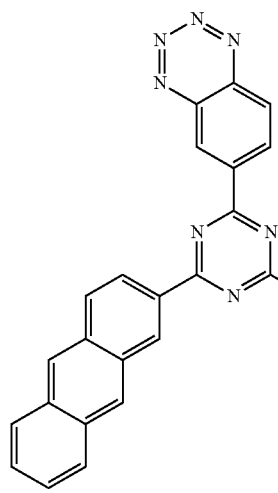
CP095
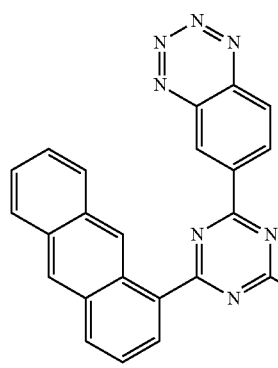

CP096
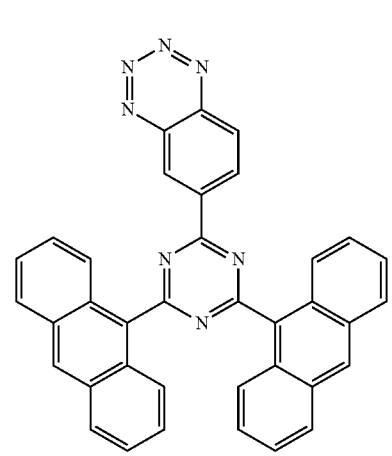
CP097
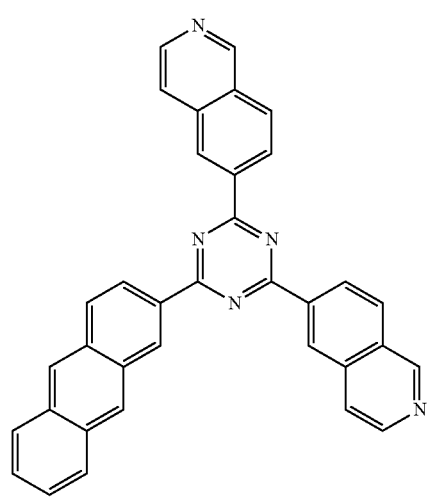
CP098
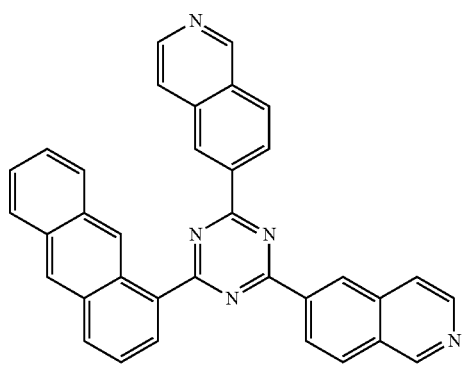
CP099
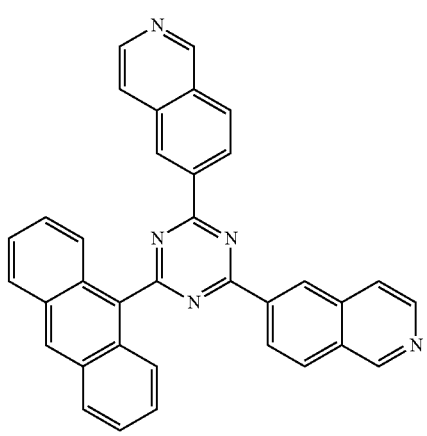
CP100
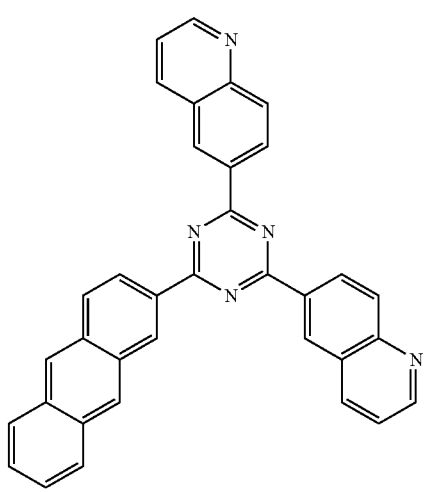
CP101
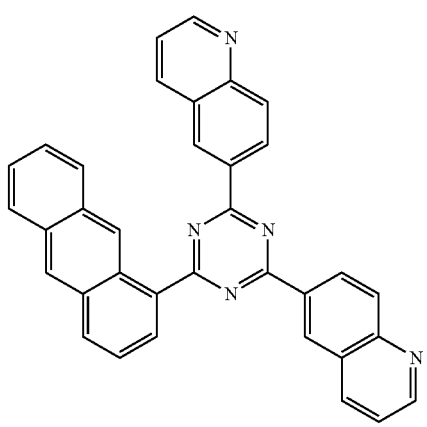

-continued
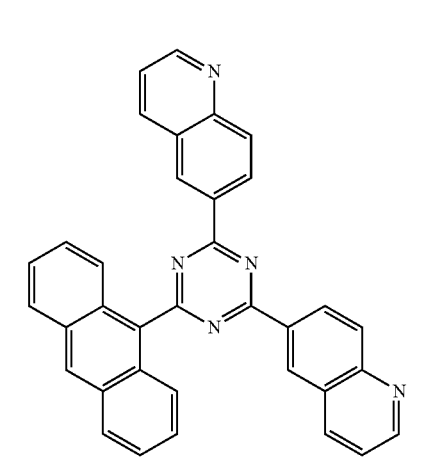
CP102
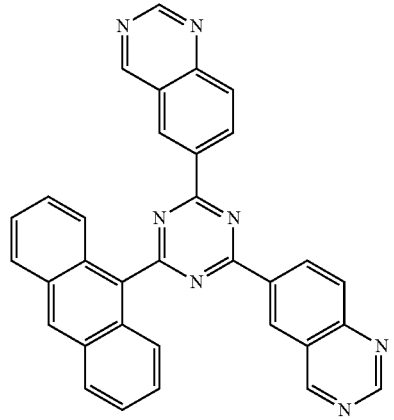
CP105
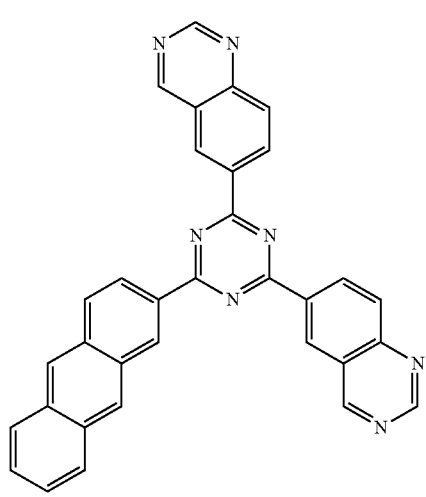
CP103
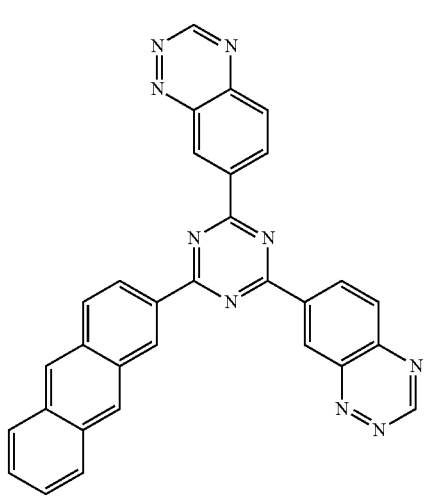
CP106
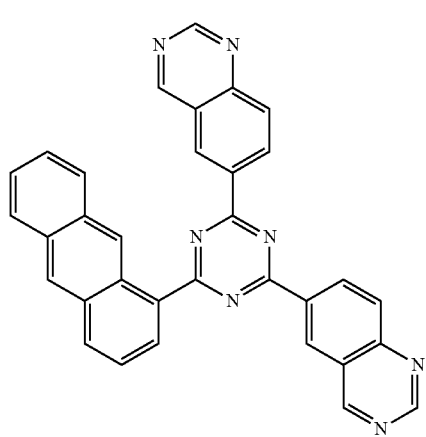
CP104
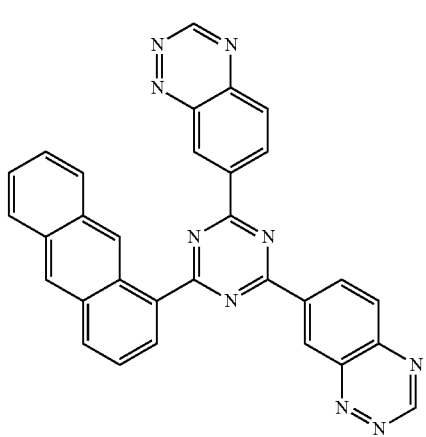
CP107

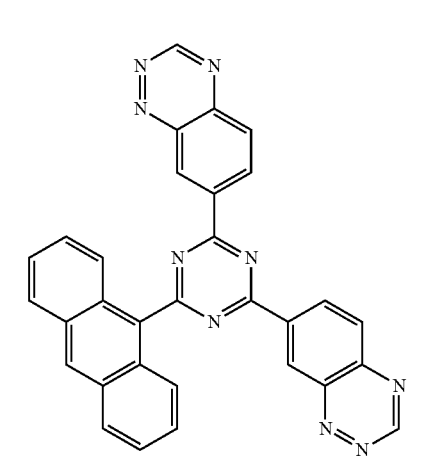
CP108
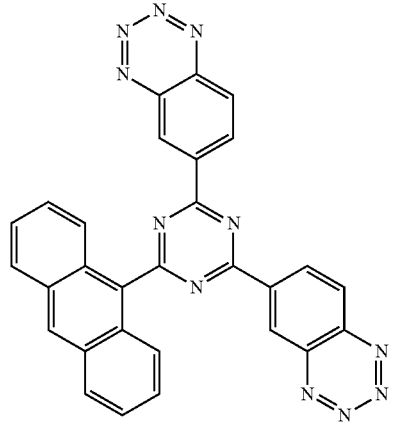
CP111
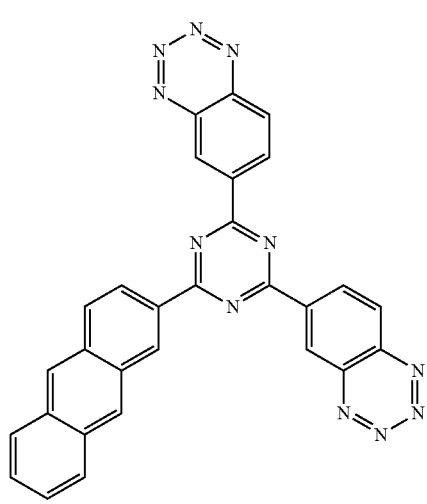
CP109
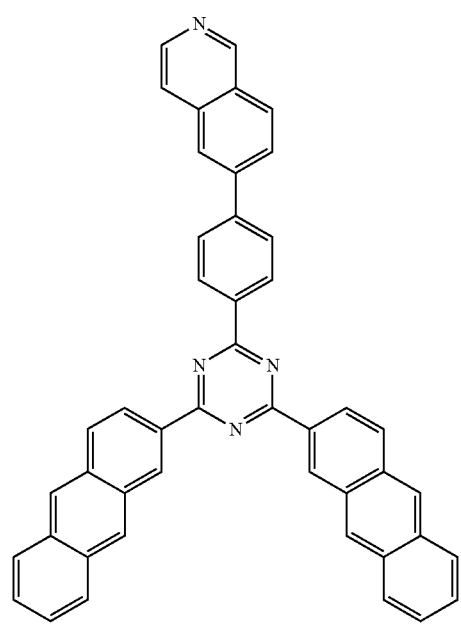
CP112
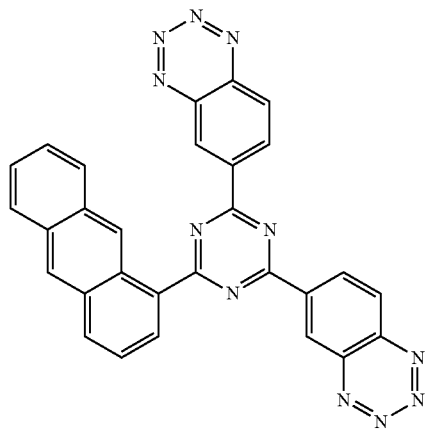
CP110
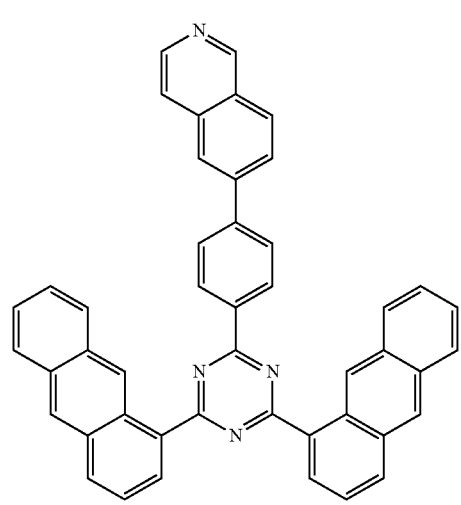
CP113

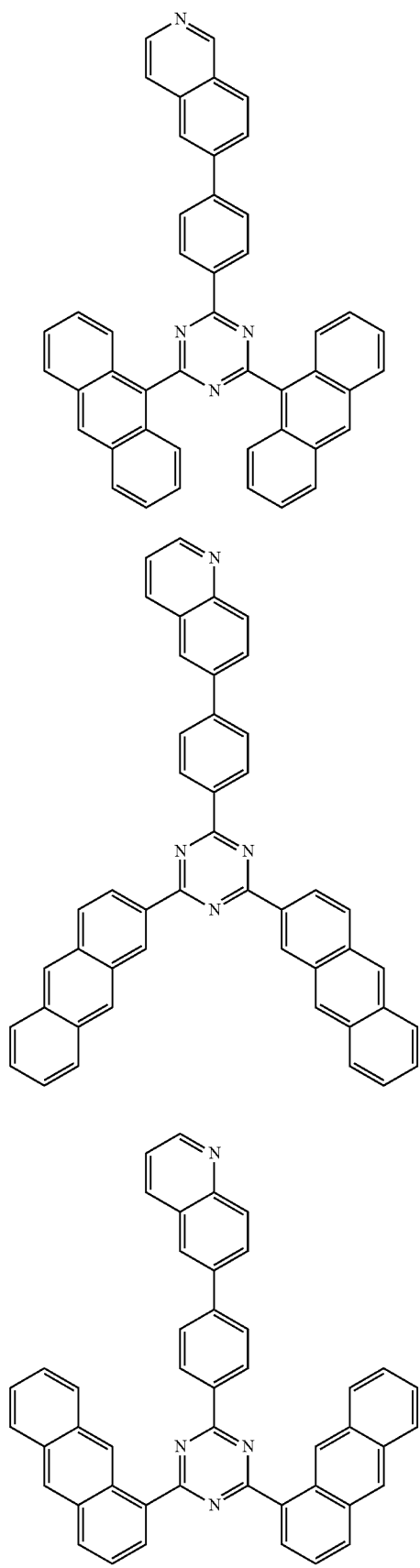
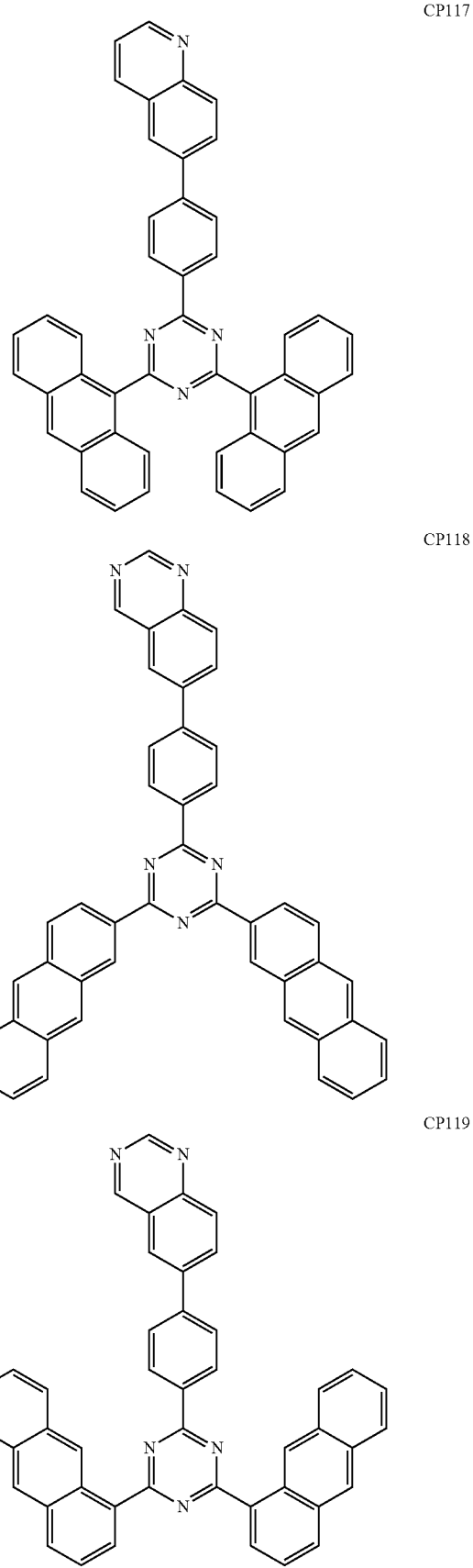

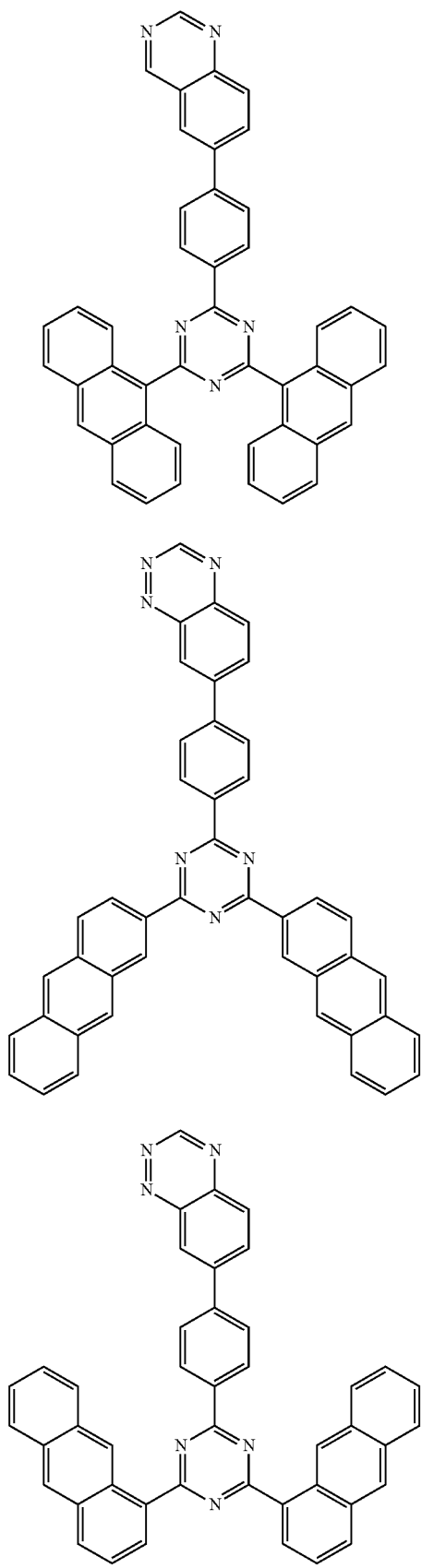
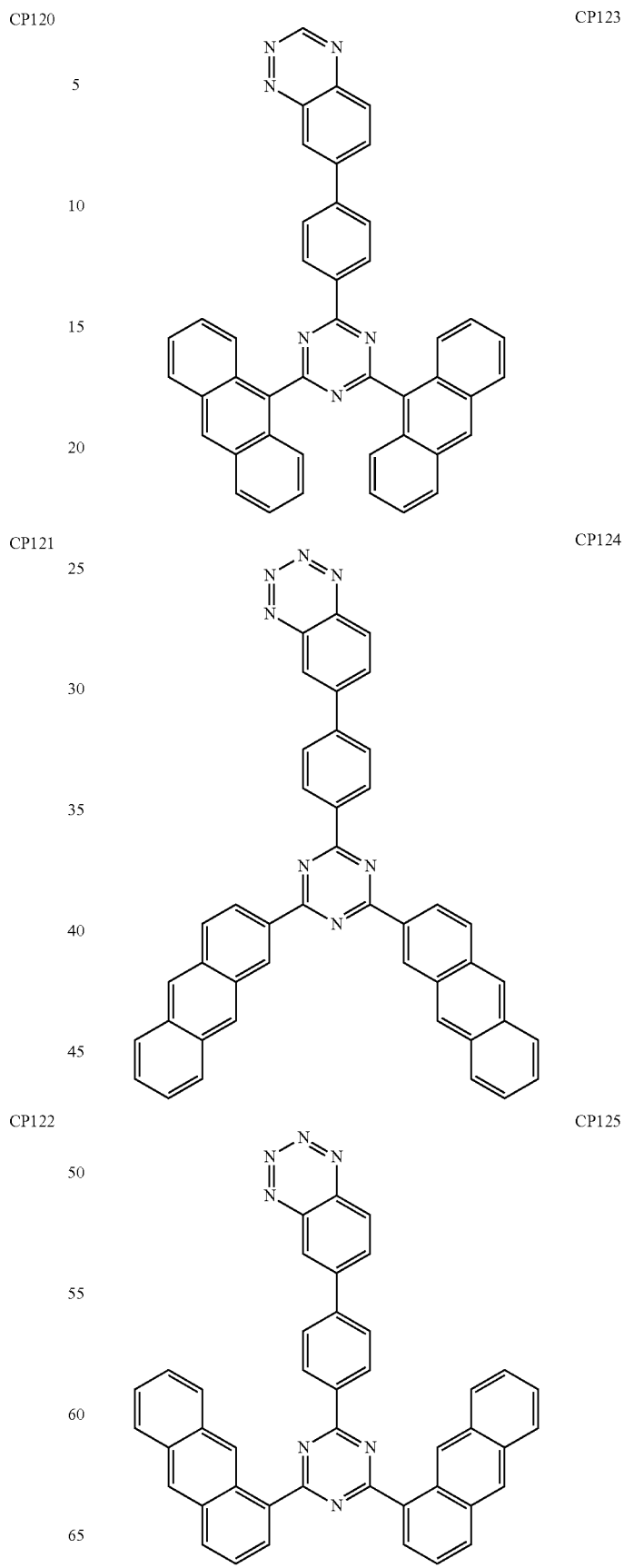

CP126
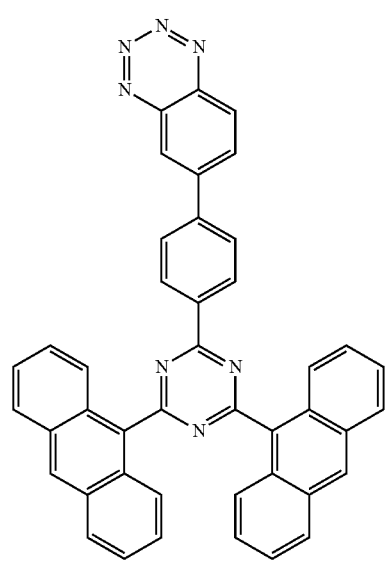
CP128
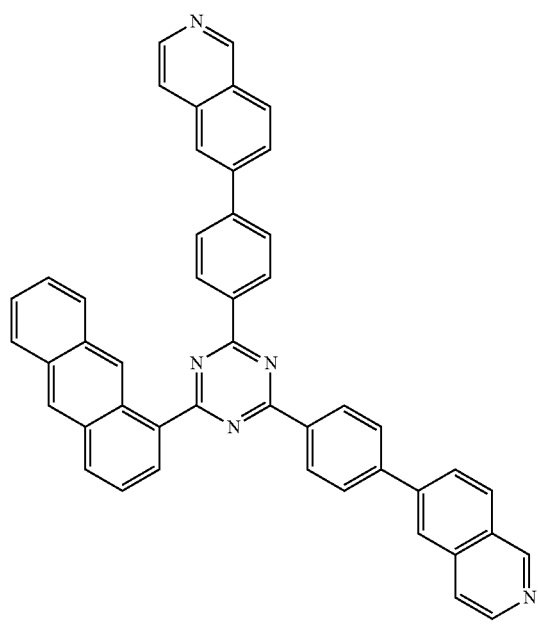
CP127
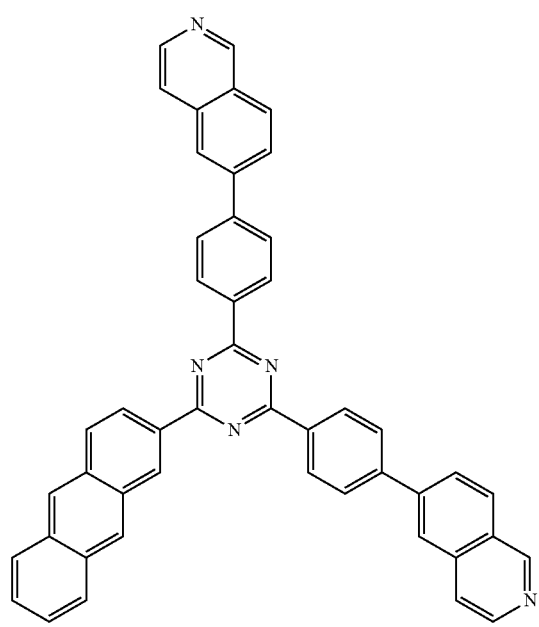
CP129
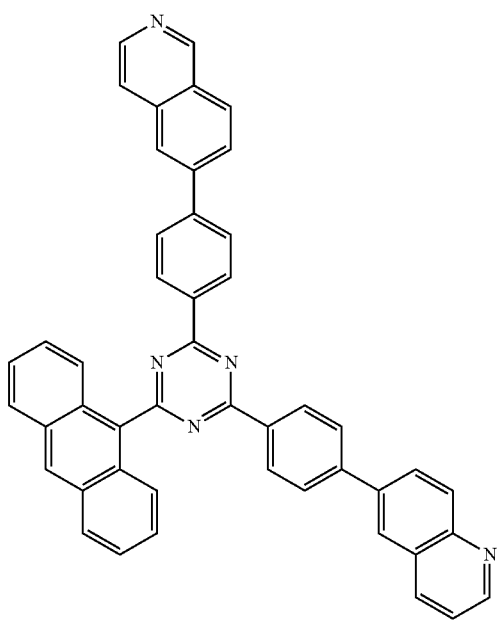

-continued
CP152
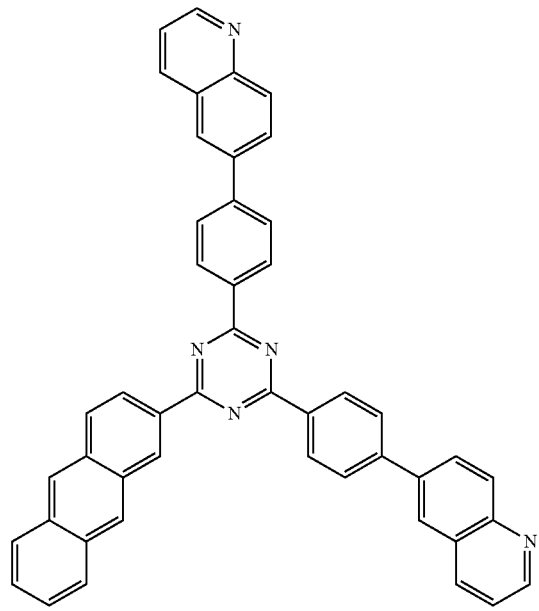
CP130
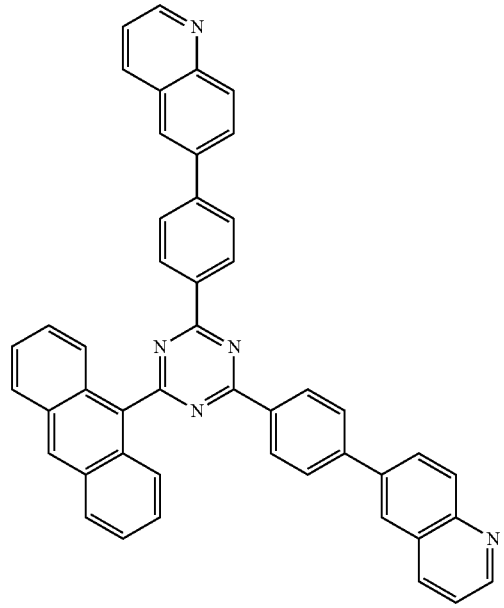
CP153
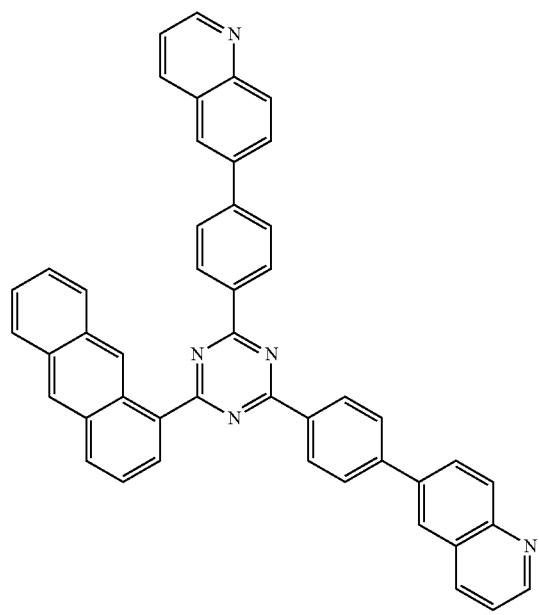
CP131
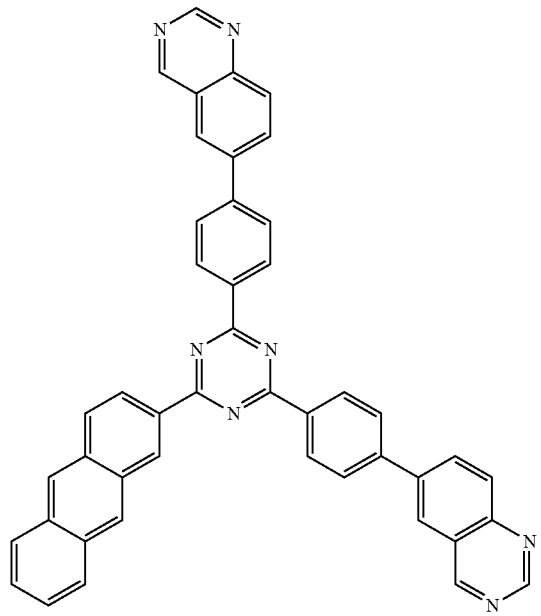

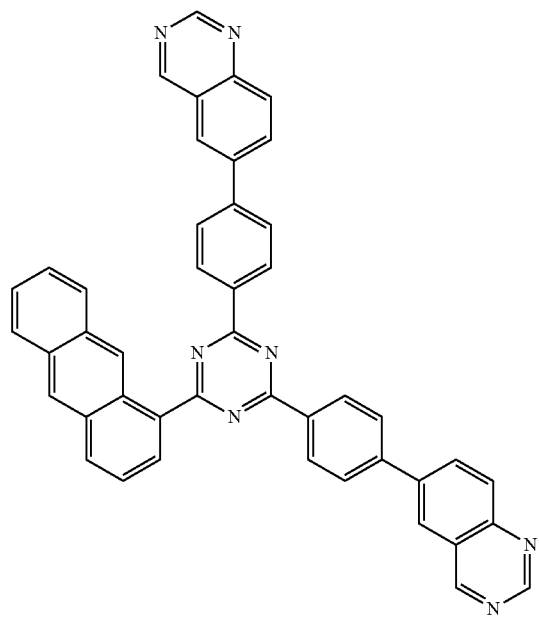
CP132
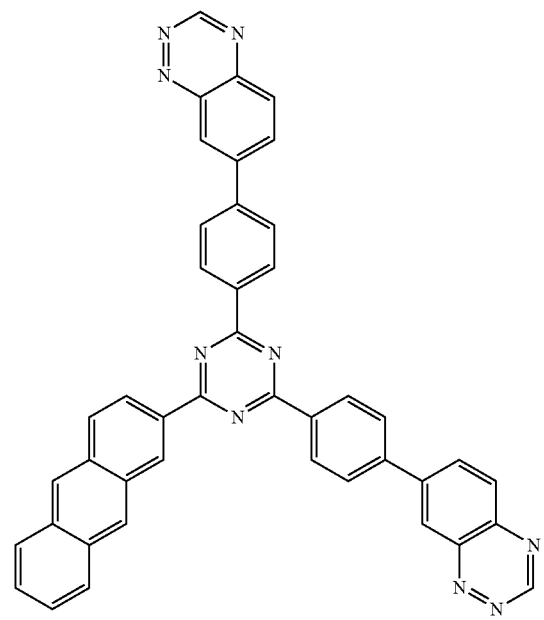
CP134
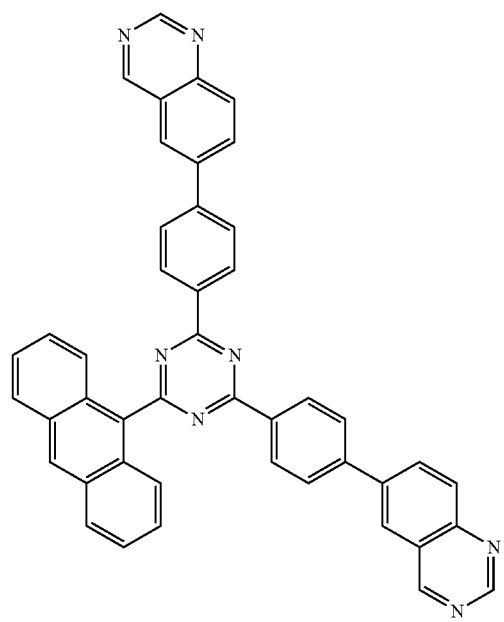
CP133
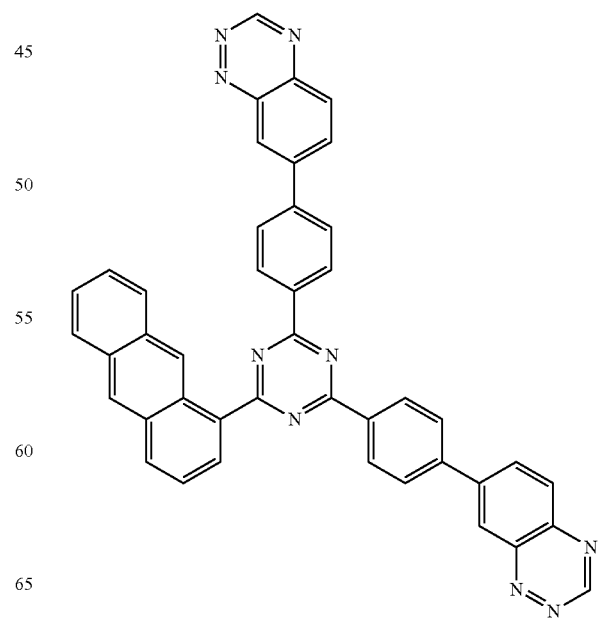
CP135

CP136
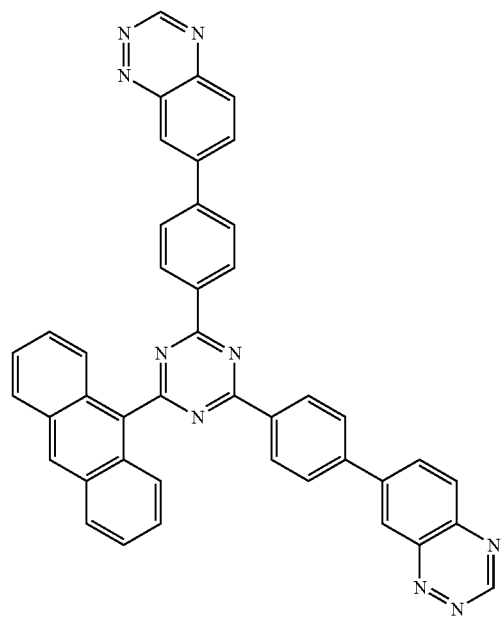
CP137
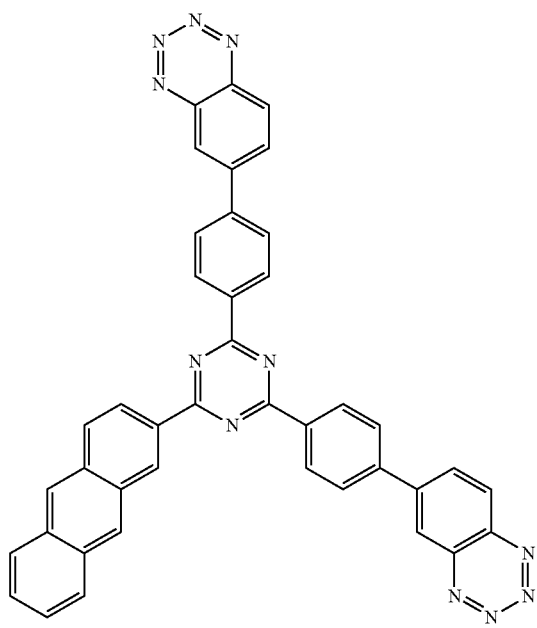
CP138
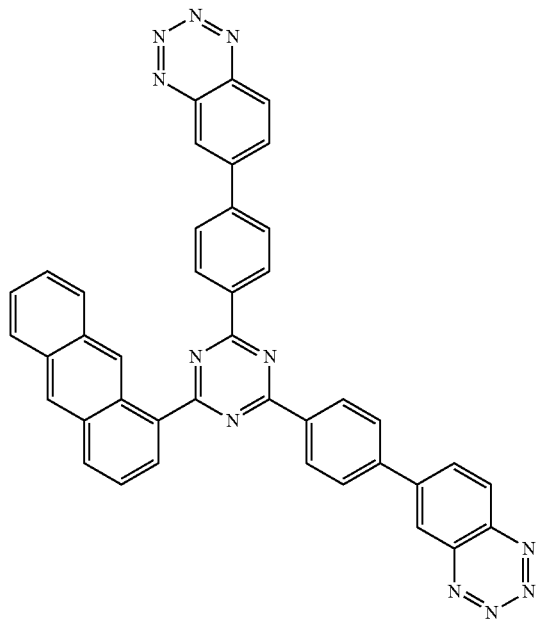
CP139
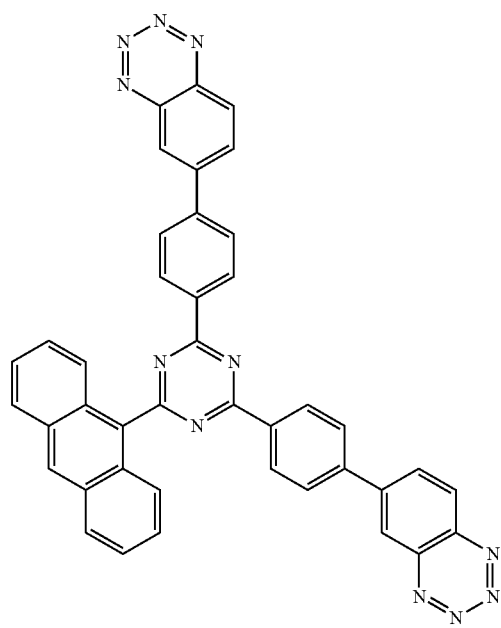

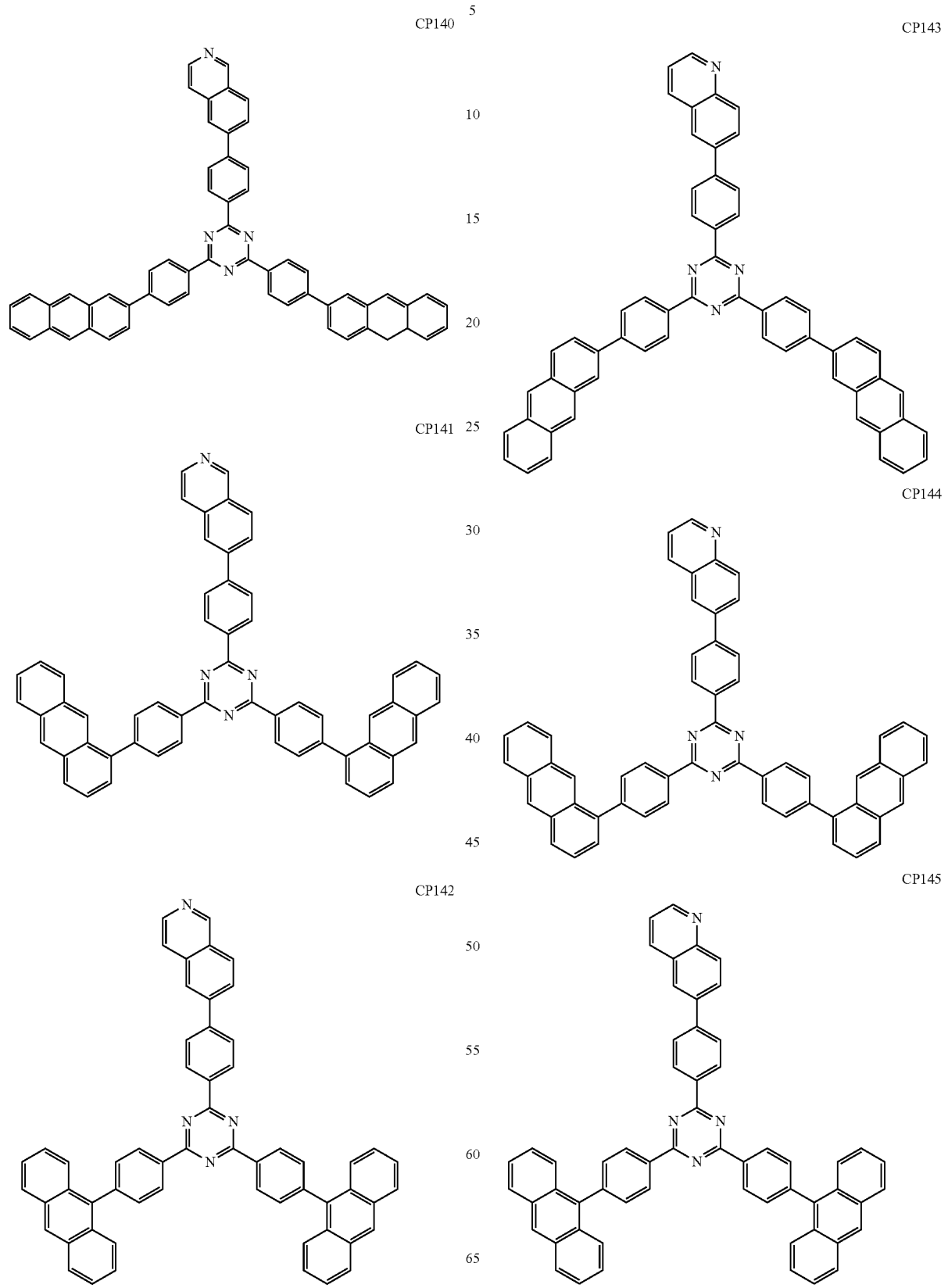

CP146
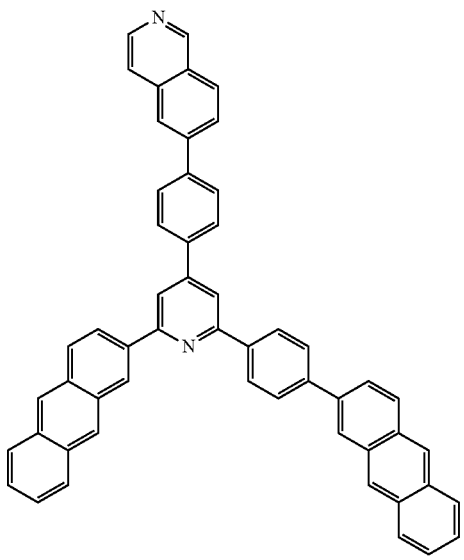
CP149
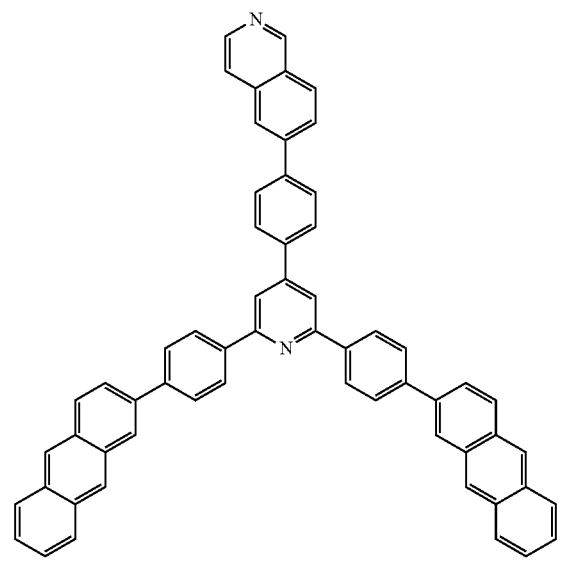
CP147
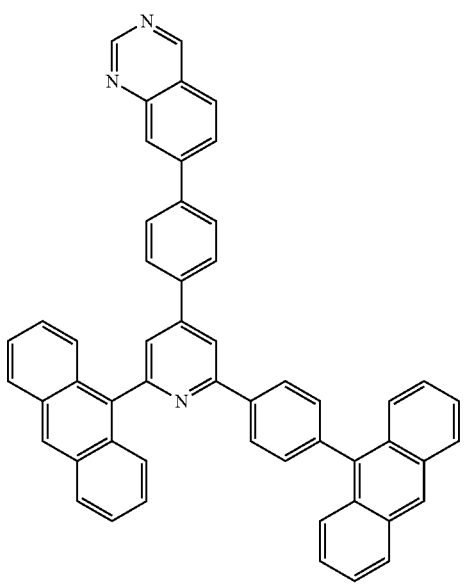
CP148
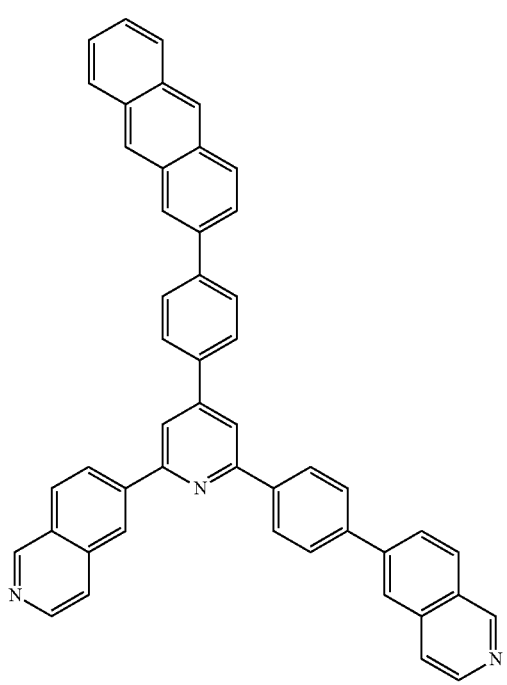

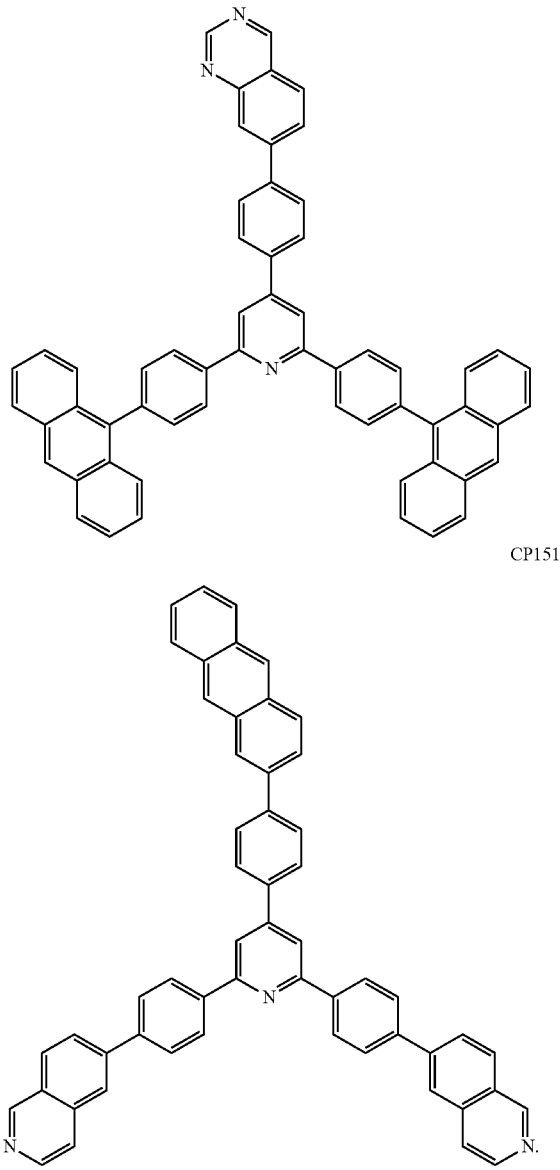

The present disclosure further provides a display panel. The display panel includes an organic light-emitting device. The organic light-emitting device includes an anode, a cathode, and at least one organic layer disposed between the anode and the cathode. A material of the at least one organic layer comprises at least one of the compounds according to the present disclosure.

In the display panel according to the present disclosure, the at least one organic layer includes an electron transport layer and a hole transport layer, and the electron transport layer and/or the hole transport layer comprise at least one of the compounds according to the present disclosure.

In the display panel according to the present disclosure, the organic light-emitting device further includes a capping layer CPL disposed on a side of the cathode facing away from the anode, and a material of the capping layer CPL includes at least one of the compounds according to the present disclosure.

The organic compound of the present disclosure contains fused rings and quinolinazole. In this way, the molecule has higher polarizability and refractive index; moreover, the molecule has a relatively flat configuration structure, which is conducive to a coupling extraction of light when serving as the capping layer.

Because the organic compound of the present disclosure has fused rings and quinolinazole, the molecular structure has a triangular configuration. Such a configuration allows the molecule to have a higher polarizability and refractive index; moreover, the molecule has a relatively flat configuration structure, which is conducive to a coupling extraction of light when serving as the capping layer.

The present disclosure further provides a display apparatus, including the display panel.

In the display panel according to the present disclosure, a material of the anode of the organic light-emitting device can be selected from metals, such as copper, gold, silver, iron, chromium, nickel, manganese, palladium, platinum, and alloys thereof; metal oxides, such as indium oxide, zinc oxide, indium tin oxide (ITO), indium zinc oxide (IZO), and the like; or conductive polymers such as polyaniline, polypyrrole, poly(3-methylthiophene), etc. In addition to the above-mentioned anode materials which are conductive to hole injection and combinations thereof, the anode also can be made of other materials that are known as suitable materials of the anode in the related art.

In the display panel according to the present disclosure, a material of the cathode of the organic light-emitting device can be selected from metals, such as aluminum, magnesium, silver, indium, tin, titanium, and alloys thereof; or multiple-layer metal materials, such as LiF/Al, $LiO_2$/Al, $BaF_2$/Al, etc. In addition to the above-mentioned cathode materials which are conductive to electron injection and combinations thereof, the cathode also can be made of other materials that are known as suitable materials of the cathode in the related art.

In the display panel according to the present disclosure, the at least one organic layer includes at least one light-emitting layer (EML), and may further include other functional layers, including a hole injection layer (HIL), a hole transport layer (HTL), an electron blocking layer (EBL), a hole blocking layer (HBL), an electron transport layer (ETL), and an electron injection layer (EIL).

In an embodiment of the present disclosure, the organic light-emitting device can be manufactured as follows: an anode is formed on a smooth transparent or opaque substrate, a thin organic layer is formed on the anode, and a cathode is formed on the thin organic layer. The thin organic layer can be formed by a known film forming method, for example, vapor deposition, sputtering, spin coating, dipping, ion plating, etc. Finally, an organic optical capping layer (CPL) is formed on the cathode. The optical CPL is made of the compound according to the present disclosure. The optical CPL can be prepared by vapor deposition or a solution method. The solution method includes ink-jet printing, spin coating, blade coating, screen printing, roll-to-roll printing, and the like.

The following examples are provided to illustrate the synthesis of several exemplary organic compounds.

Example 1

Synthetic Scheme of Compound CP001

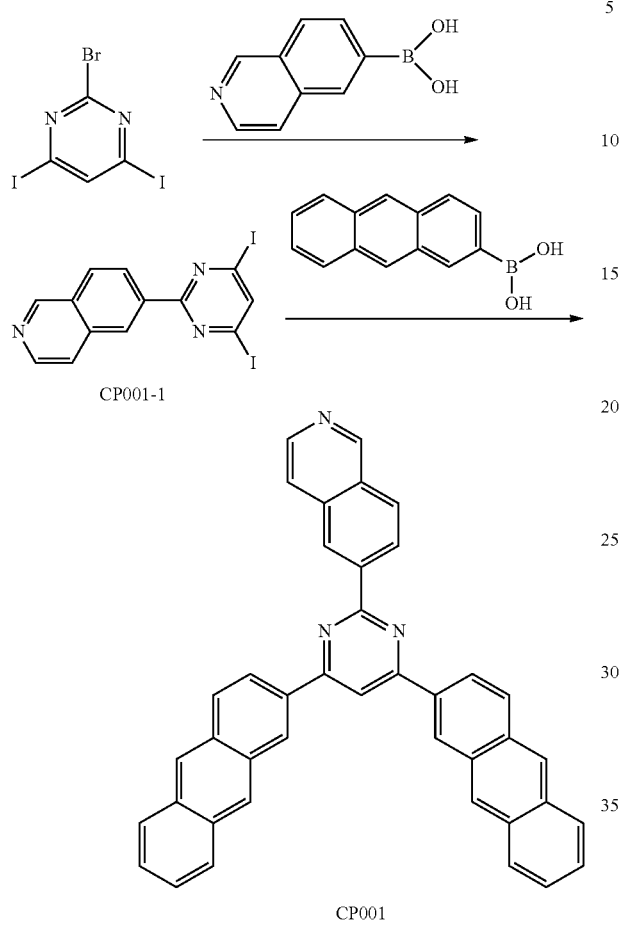

CP001

In a 250 mL round bottom flask, 2-bromo-4,6-diiodo-pyrimidine (10 mmol), 6-boric acid-isoquinoline (12 mmol), and Pd(PPh$_3$)$_4$ (0.3 mmol) were added to a mixture of toluene (30 mL)/ethanol (20 mL) and an aqueous solution (10 mL) of potassium carbonate (12 mmol), and refluxed under nitrogen atmosphere for 12 h. The obtained mixture was cooled to room temperature, added to water, and then filtered through a pad of diatomite. The filtrate was extracted with dichloromethane, then washed with water, and dried over anhydrous magnesium sulfate. After filtration and evaporation, the crude product was purified by silica gel column chromatography to obtain an intermediate product CP001-1.

In a 250 mL round bottom flask, the intermediate product CP001-1 (10 mmol), 2-boronic acid-anthracene (22 mmol), and Pd(PPh$_3$)$_4$ (0.3 mmol) were added to a mixture of toluene (30 mL)/ethanol (20 mL) and an aqueous solution (10 mL) of potassium carbonate (12 mmol), and refluxed under nitrogen atmosphere for 12 h. The obtained mixture was cooled to room temperature, added to water, and then filtered through a pad of diatomite. The filtrate was extracted with dichloromethane, then washed with water, and dried over anhydrous magnesium sulfate. After filtration and evaporation, the crude product was purified by silica gel column chromatography to obtain a final product CP001.

Elemental analysis results of compound CP001 (molecular formula C$_{41}$H$_{25}$N$_3$): theoretical: C, 87.99; H, 4.50; N, 7.51. Measured: C, 87.99; H, 4.50; N, 7.51. ESI-MS (m/z) (M+) analyzed with LC-MS: theoretical: 559.20, measured: 559.66.

Example 2

Synthetic Scheme of Compound CP003:

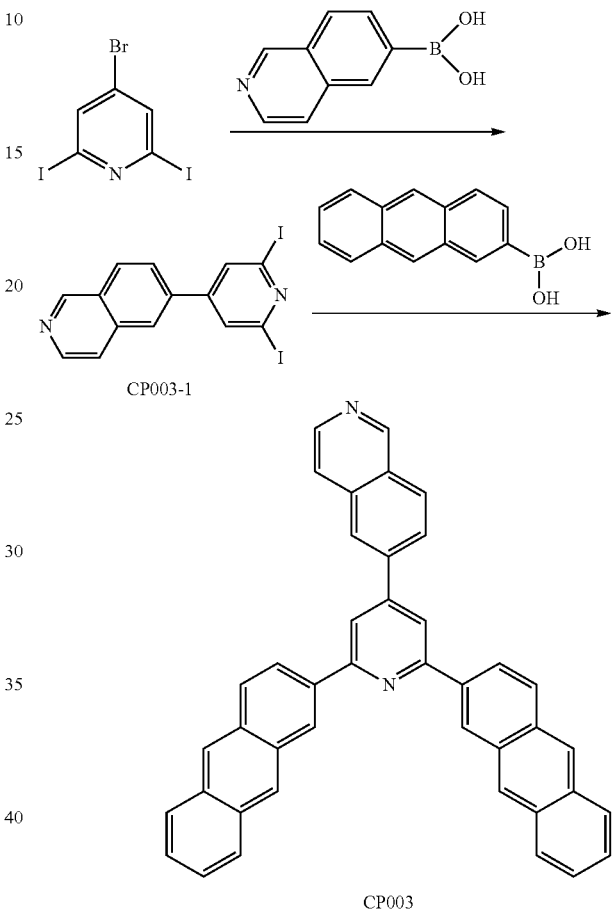

CP003

In a 250 mL round bottom flask, 4-bromo-2,6-diiodo-pyridine (10 mmol), 6-boric acid-isoquinoline (12 mmol), and Pd(PPh$_3$)$_4$ (0.3 mmol) were added to a mixture of toluene (30 mL)/ethanol (20 mL) and an aqueous solution (10 mL) of potassium carbonate (12 mmol), and refluxed under nitrogen atmosphere for 12 h. The obtained mixture was cooled to room temperature, added to water, and then filtered through a pad of diatomite. The filtrate was extracted with dichloromethane, then washed with water, and dried over anhydrous magnesium sulfate. After filtration and evaporation, the crude product was purified by silica gel column chromatography to obtain an intermediate product CP003-1.

In a 250 mL round bottom flask, the intermediate product CP003-1 (10 mmol), 2-boronic acid-anthracene (22 mmol), and Pd(PPh$_3$)$_4$ (0.3 mmol) were added to a mixture of toluene (30 mL)/ethanol (20 mL) and an aqueous solution (10 mL) of potassium carbonate (12 mmol), and refluxed under nitrogen atmosphere for 12 h. The obtained mixture was cooled to room temperature, added to water, and then filtered through a pad of diatomite. The filtrate was extracted with dichloromethane, then washed with water, and dried over anhydrous magnesium sulfate. After filtration and evaporation, the crude product was purified by silica gel column chromatography to obtain a final product CP003.

Elemental analysis results of compound CP003 (molecular formula $C_{42}H_{26}N_2$): theoretical: C, 90.29; H, 4.69; N, 5.01. Measured: C, 90.29; H, 4.69; N, 5.01. ESI-MS(m/z) (M+) analyzed with LC-MS: theoretical: 558.21, measured: 558.67.

Example 3

Synthetic Scheme of Compound CP011:

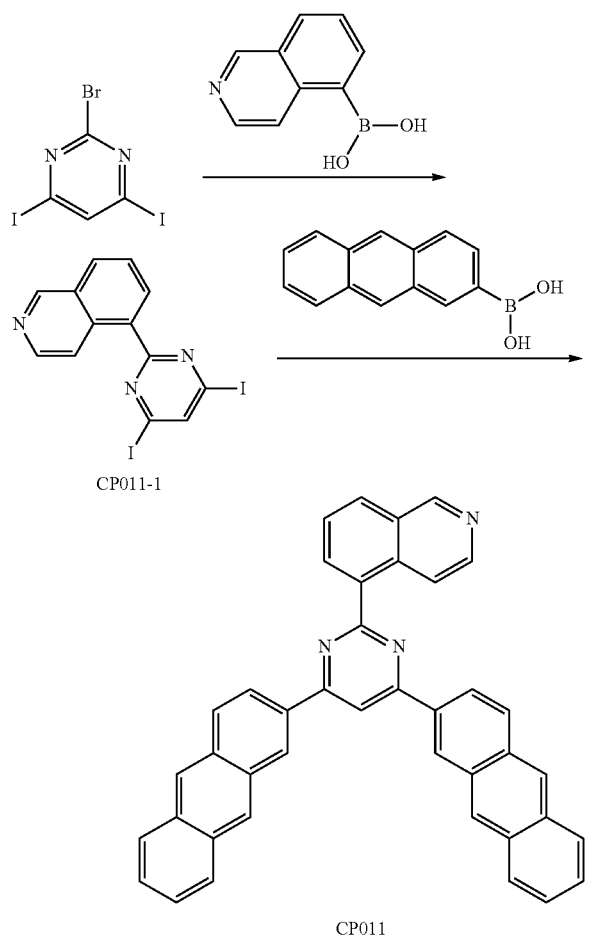

CP011-1

CP011

In a 250 mL round bottom flask, 2-bromo-4,6-diiodo-pyrimidine (10 mmol), 5-boric acid-isoquinoline (12 mmol), and Pd(PPh$_3$)$_4$ (0.3 mmol) were added to a mixture of toluene (30 mL)/ethanol (20 mL) and an aqueous solution (10 mL) of potassium carbonate (12 mmol), and refluxed under nitrogen atmosphere for 12 h. The obtained mixture was cooled to room temperature, added to water, and then filtered through a pad of diatomite. The filtrate was extracted with dichloromethane, then washed with water, and dried over anhydrous magnesium sulfate. After filtration and evaporation, the crude product was purified by silica gel column chromatography to obtain an intermediate product CP011-1.

In a 250 mL round bottom flask, the intermediate product CP011-1 (10 mmol), 2-boronic acid-anthracene (22 mmol), and Pd(PPh$_3$)$_4$ (0.3 mmol) were added to a mixture of toluene (30 mL)/ethanol (20 mL) and an aqueous solution (10 mL) of potassium carbonate (12 mmol), and refluxed under nitrogen atmosphere for 12 h. The obtained mixture was cooled to room temperature, added to water, and then filtered through a pad of diatomite. The filtrate was extracted with dichloromethane, then washed with water, and dried over anhydrous magnesium sulfate. After filtration and evaporation, the crude product was purified by silica gel column chromatography to obtain a final product CP011.

Elemental analysis results of compound CP011 (molecular formula $C_{41}H_{25}N_3$): theoretical: C, 87.99; H, 4.50; N, 7.51. Measured: C, 87.99; H, 4.51; N, 7.50. ESI-MS(m/z) (M+) analyzed with LC-MS: theoretical: 559.20, measured: 559.66.

Example 4

Synthetic Scheme of Compound CP019

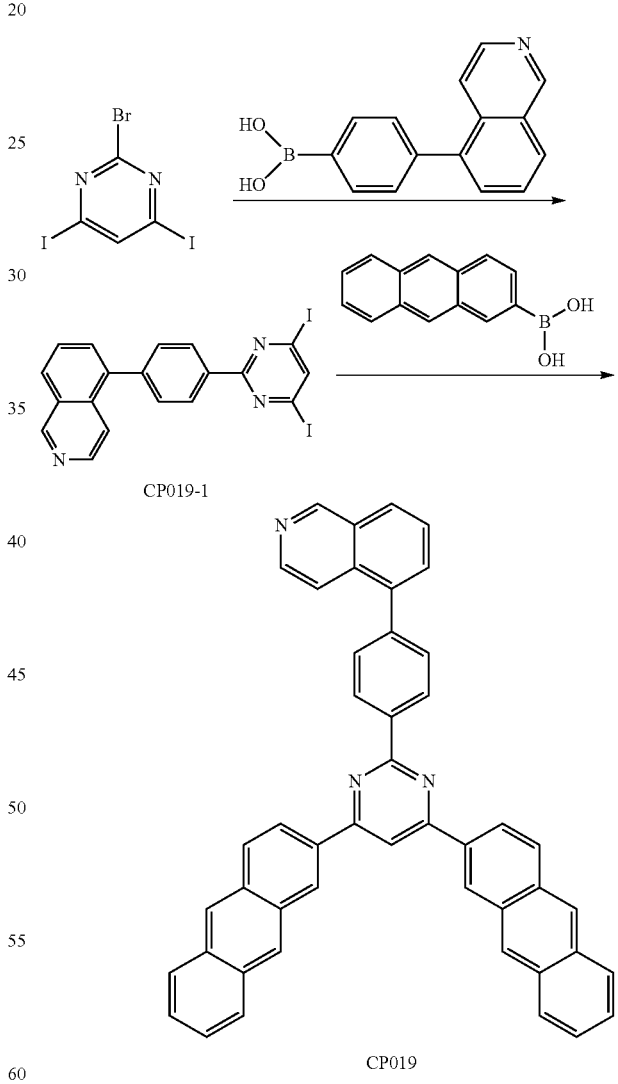

CP019-1

CP019

In a 250 mL round bottom flask, 2-bromo-4,6-diiodo-pyrimidine (10 mmol), (4-isoquinolinyl-5-phenyl)-boric acid (12 mmol), and Pd(PPh$_3$)$_4$ (0.3 mmol) were added to a mixture of toluene (30 mL)/ethanol (20 mL) and an aqueous solution (10 mL) of potassium carbonate (12 mmol), and refluxed under nitrogen atmosphere for 12 h. The obtained mixture was cooled to room temperature, added to water, and then filtered through a pad of diatomite. The filtrate was extracted with dichloromethane, then washed with water, and dried over anhydrous magnesium sulfate. After filtration and evaporation, the crude product was purified by silica gel column chromatography to obtain an intermediate product CP019-1.

In a 250 mL round bottom flask, the intermediate product CP019-1 (10 mmol), 2-boric acid-anthracene (22 mmol), and Pd(PPh$_3$)$_4$ (0.3 mmol) were added to a mixture of toluene (30 mL)/ethanol (20 mL) and an aqueous solution (10 mL) of potassium carbonate (12 mmol), and refluxed under nitrogen atmosphere for 12 h. The obtained mixture was cooled to room temperature, added to water, and then filtered through a pad of diatomite. The filtrate was extracted with dichloromethane, then washed with water, and dried over anhydrous magnesium sulfate. After filtration and evaporation, the crude product was purified by silica gel column chromatography to obtain a final product CP019.

Elemental analysis results of compound CP019 (molecular formula $C_{47}H_{29}N_3$): theoretical: C, 88.79; H, 4.60; N, 6.61. Measured: C, 88.79; H, 4.60; N, 6.61. ESI-MS(m/z) (M+) analyzed with LC-MS: theoretical: 635.24, measured: 635.79.

Example 5

Synthetic Scheme of Compound CP021:

In a 250 mL round bottom flask, 2-bromo-4,6-diiodo-pyrimidine (10 mmol), 6-boric acid-isoquinoline (12 mmol), and Pd(PPh$_3$)$_4$ (0.3 mmol) were added to a mixture of toluene (30 mL)/ethanol (20 mL) and an aqueous solution (10 mL) of potassium carbonate (12 mmol), and refluxed under nitrogen atmosphere for 12 h. The obtained mixture was cooled to room temperature, added to water, and then filtered through a pad of diatomite. The filtrate was extracted with dichloromethane, then washed with water, and dried over anhydrous magnesium sulfate. After filtration and evaporation, the crude product was purified by silica gel column chromatography to obtain an intermediate product CP021-1.

In a 250 mL round bottom flask, the intermediate product CP021-1 (10 mmol), 9-boric acid-anthracene (22 mmol), and Pd(PPh$_3$)$_4$ (0.3 mmol) were added to a mixture of toluene (30 mL)/ethanol (20 mL) and an aqueous solution (10 mL) of potassium carbonate (12 mmol), and refluxed under nitrogen atmosphere for 12 h. The obtained mixture was cooled to room temperature, added to water, and then filtered through a pad of diatomite. The filtrate was extracted with dichloromethane, then washed with water, and dried over anhydrous magnesium sulfate. After filtration and evaporation, the crude product was purified by silica gel column chromatography to obtain a final product CP021.

Elemental analysis results of compound CP021 (molecular formula $C_{41}H_{25}N_3$): theoretical: C, 87.99; H, 4.50; N, 7.51. Measured: C, 87.99; H, 4.50; N, 7.51. ESI-MS(m/z) (M+) analyzed with LC-MS: theoretical: 559.20, measured: 559.66.

Example 6

Synthetic Scheme of Compound CP029:

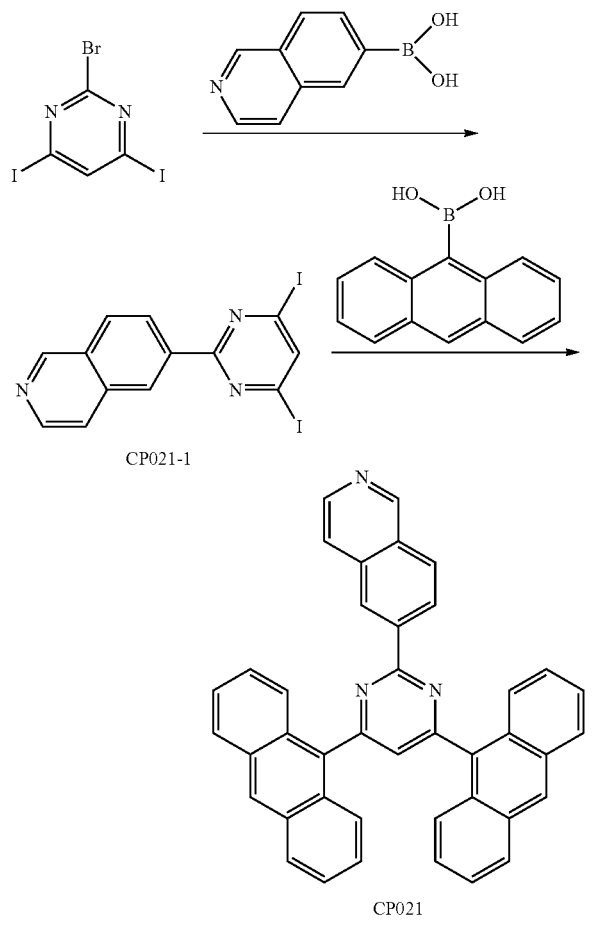

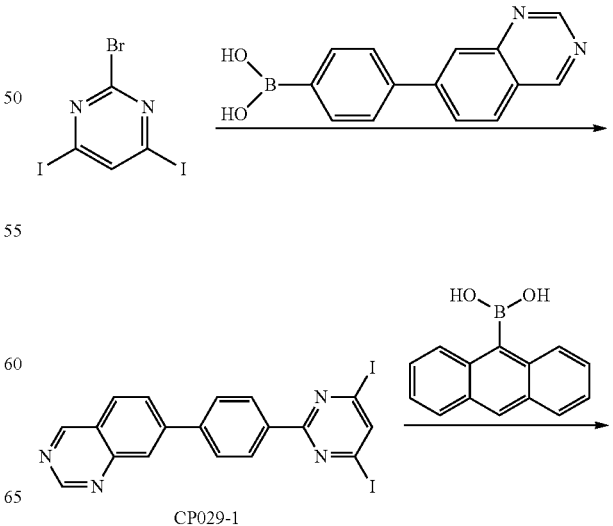

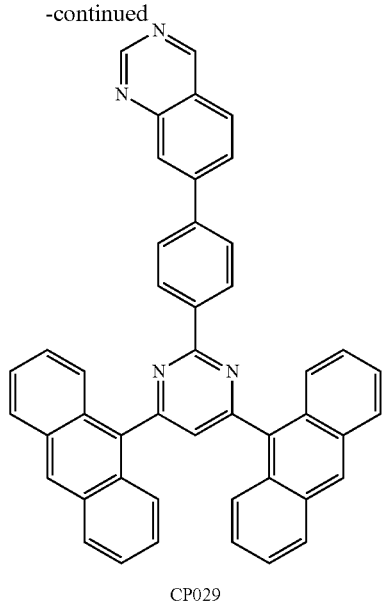

CP029

In a 250 mL round bottom flask, 2-bromo-4,6-diiodopyrimidine (10 mmol), (4-quinazolinyl-7-phenyl)-boric acid (12 mmol), and Pd(PPh$_3$)$_4$ (0.3 mmol) were added to a mixture of toluene (30 mL)/ethanol (20 mL) and an aqueous solution (10 mL) of potassium carbonate (12 mmol), and refluxed under nitrogen atmosphere for 12 h. The obtained mixture was cooled to room temperature, added to water, and then filtered through a pad of diatomite. The filtrate was extracted with dichloromethane, then washed with water, and dried over anhydrous magnesium sulfate. After filtration and evaporation, the crude product was purified by silica gel column chromatography to obtain an intermediate product CP029-1.

In a 250 mL round bottom flask, the intermediate product CP029-1 (10 mmol), 9-boric acid-anthracene (22 mmol), and Pd(PPh$_3$)$_4$ (0.3 mmol) were added to a mixture of toluene (30 mL)/ethanol (20 mL) and an aqueous solution (10 mL) of potassium carbonate (12 mmol), and refluxed under nitrogen atmosphere for 12 h. The obtained mixture was cooled to room temperature, added to water, and then filtered through a pad of diatomite. The filtrate was extracted with dichloromethane, then washed with water, and dried over anhydrous magnesium sulfate. After filtration and evaporation, the crude product was purified by silica gel column chromatography to obtain a final product CP029.

Elemental analysis results of compound CP029 (molecular formula C$_{46}$H$_{28}$N$_4$): theoretical: C, 86.77; H, 4.43; N, 8.80. Measured: C, 86.77; H, 4.43; N, 8.80. ESI-MS(m/z) (M+) analyzed with LC-MS: theoretical: 636.23, measured: 636.74.

Example 7

Synthetic Scheme of Compound CP033:

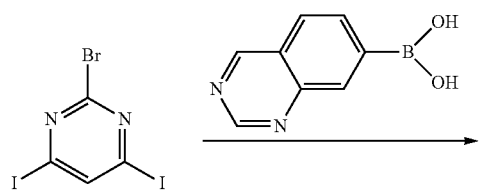

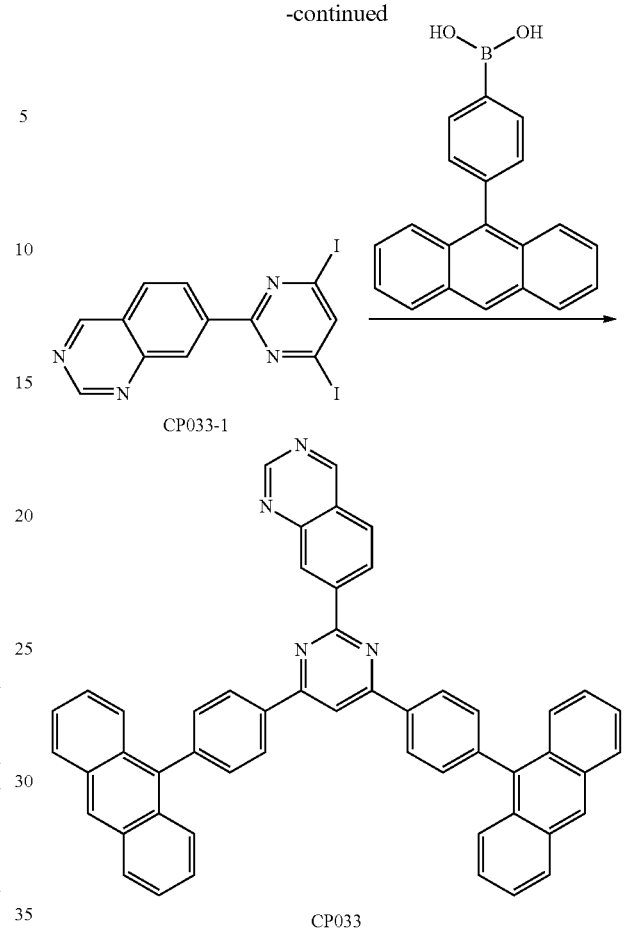

CP033

In a 250 mL round bottom flask, 2-bromo-4,6-diiodopyrimidine (10 mmol), 6-boric acid-quinazoline (12 mmol), and Pd(PPh$_3$)$_4$ (0.3 mmol) were added to a mixture of toluene (30 mL)/ethanol (20 mL) and an aqueous solution (10 mL) of potassium carbonate (12 mmol), and refluxed under nitrogen atmosphere for 12 h. The obtained mixture was cooled to room temperature, added to water, and then filtered through a pad of diatomite. The filtrate was extracted with dichloromethane, then washed with water, and dried over anhydrous magnesium sulfate. After filtration and evaporation, the crude product was purified by silica gel column chromatography to obtain an intermediate product CP033-1.

In a 250 mL round bottom flask, the intermediate product CP033-1 (10 mmol), (4-anthryl-9-phenyl)-boric acid (22 mmol), and Pd(PPh$_3$)$_4$ (0.3 mmol) were added to a mixture of toluene (30 mL)/ethanol (20 mL) and an aqueous solution (10 mL) of potassium carbonate (12 mmol), and refluxed under nitrogen atmosphere for 12 h. The obtained mixture was cooled to room temperature, added to water, and then filtered through a pad of diatomite. The filtrate was extracted with dichloromethane, then washed with water, and dried over anhydrous magnesium sulfate. After filtration and evaporation, the crude product was purified by silica gel column chromatography to obtain a final product CP033.

Elemental analysis results of compound CP033 (molecular formula C$_{52}$H$_{32}$N$_4$): theoretical: C, 87.62; H, 4.52; N, 7.86. Measured: C, 87.62; H, 4.51; N, 7.87. ESI-MS(m/z) (M+) analyzed with LC-MS: theoretical: 712.26, measured: 712.84.

Example 8

Synthetic Scheme of Compound CP038:

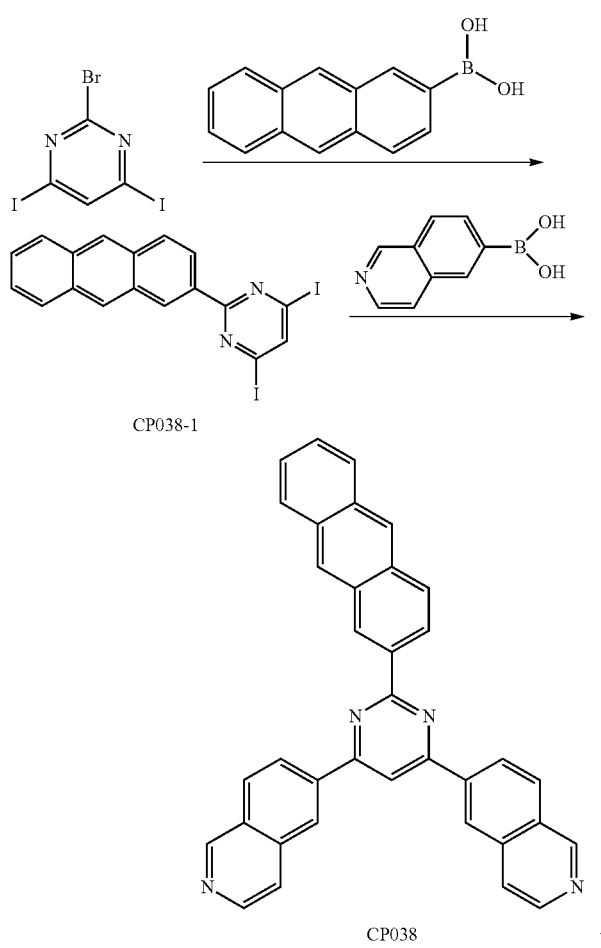

In a 250 mL round bottom flask, 2-bromo-4,6-diiodo-pyrimidine (10 mmol), 9-boric acid-anthracene (12 mmol), and Pd(PPh$_3$)$_4$ (0.3 mmol) were added to a mixture of toluene (30 mL)/ethanol (20 mL) and an aqueous solution (10 mL) of potassium carbonate (12 mmol), and refluxed under nitrogen atmosphere for 12 h. The obtained mixture was cooled to room temperature, added to water, and then filtered through a pad of diatomite. The filtrate was extracted with dichloromethane, then washed with water, and dried over anhydrous magnesium sulfate. After filtration and evaporation, the crude product was purified by silica gel column chromatography to obtain an intermediate product CP038-1.

In a 250 mL round bottom flask, the intermediate product CP038-1 (10 mmol), 6-boric acid-isoquinoline (22 mmol), and Pd(PPh$_3$)$_4$ (0.3 mmol) were added to a mixture of toluene (30 mL)/ethanol (20 mL) and an aqueous solution (10 mL) of potassium carbonate (12 mmol), and refluxed under nitrogen atmosphere for 12 h. The obtained mixture was cooled to room temperature, added to water, and then filtered through a pad of diatomite. The filtrate was extracted with dichloromethane, then washed with water, and dried over anhydrous magnesium sulfate. After filtration and evaporation, the crude product was purified by silica gel column chromatography to obtain a final product CP038.

Elemental analysis results of compound CP038 (molecular formula C$_{36}$H$_{22}$N$_4$): theoretical: C, 84.68; H, 4.34; N, 10.97. Measured: C, 84.68; H, 4.34; N, 10.97. ESI-MS(m/z)(M+) analyzed with LC-MS: theoretical: 510.18, measured: 510.59.

Example 9

Synthetic Scheme of Compound CP044:

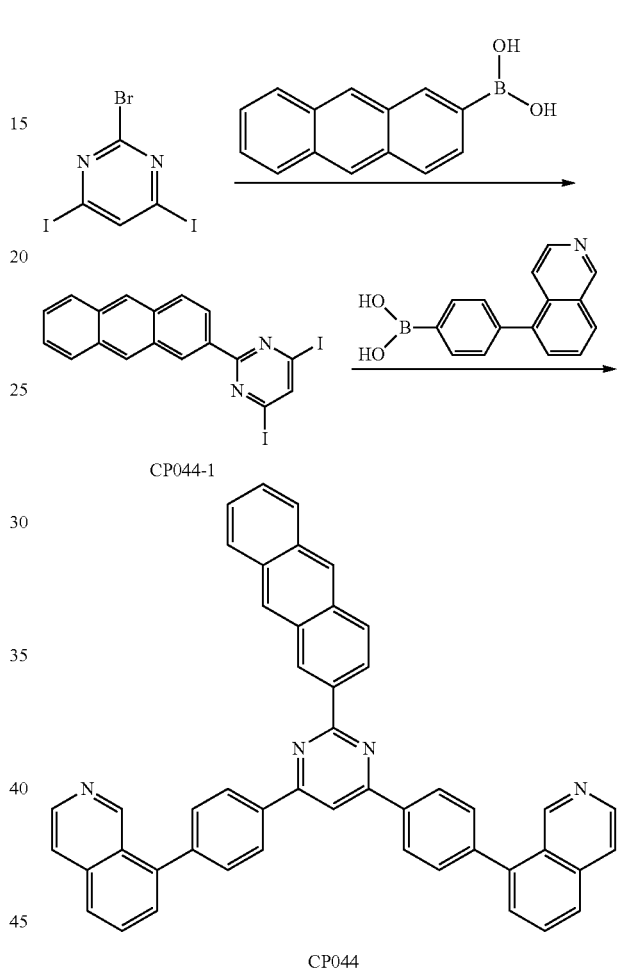

In a 250 mL round bottom flask, 2-bromo-4,6-diiodo-pyrimidine (10 mmol), 9-boric acid-anthracene (12 mmol), and Pd(PPh$_3$)$_4$ (0.3 mmol) were added to a mixture of toluene (30 mL)/ethanol (20 mL) and an aqueous solution (10 mL) of potassium carbonate (12 mmol), and refluxed under nitrogen atmosphere for 12 h. The obtained mixture was cooled to room temperature, added to water, and then filtered through a pad of diatomite. The filtrate was extracted with dichloromethane, then washed with water, and dried over anhydrous magnesium sulfate. After filtration and evaporation, the crude product was purified by silica gel column chromatography to obtain an intermediate product CP044-1.

In a 250 mL round bottom flask, the intermediate product CP044-1 (10 mmol), (4-isoquinolinyl-5-phenyl)boric acid (22 mmol), and Pd(PPh$_3$)$_4$ (0.3 mmol) were added to a mixture of toluene (30 mL)/ethanol (20 mL) and an aqueous solution (10 mL) of potassium carbonate (12 mmol), and refluxed under nitrogen atmosphere for 12 h. The obtained mixture was cooled to room temperature, added to water, and then filtered through a pad of diatomite. The filtrate was extracted with dichloromethane, then washed with water, and dried over anhydrous magnesium sulfate. After filtration and evaporation, the crude product was purified by silica gel column chromatography to obtain a final product CP044.

Elemental analysis results of compound CP044 (molecular formula $C_{48}H_{30}N_4$): theoretical: C, 86.98; H, 4.56; N, 8.45. Measured: C, 86.98; H, 4.57; N, 8.44. ESI-MS(m/z) (M+) analyzed with LC-MS: theoretical: 662.25, measured: 662.78.

In Table 1 are listed thermal performance and refractive index test results of the organic compounds prepared in Examples 1 to 9 of the present disclosure. In Table 1, comparative example adopts compound 8, which has a structure represented by the following formula:

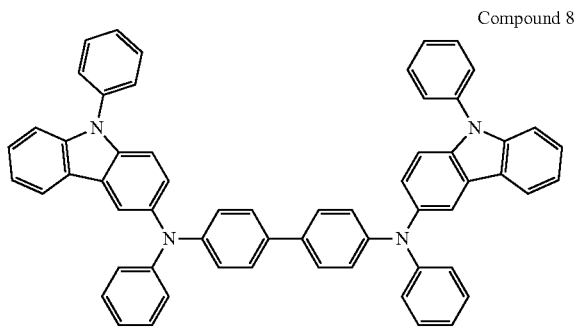 [SMILES: c1ccc(N(c2ccc(-c3ccc(N(c4ccccc4)c4ccc5c(c4)c4ccccc4n5-c4ccccc4)cc3)cc2)c2ccc3c(c2)c2ccccc2n3-c2ccccc2)cc1]

Compound 8

TABLE 1 test results of thermal performance and refractive index

| Compound | Tg (° C.) | Refractive index | | |
|---|---|---|---|---|
| | | n@450 | n@530 | n@620 |
| CP001 | 135 | 2.25 | 2.13 | 2.06 |
| CP003 | 138 | 2.23 | 2.11 | 2.04 |
| CP011 | 137 | 2.24 | 2.12 | 2.05 |
| CP019 | 132 | 2.26 | 2.14 | 2.07 |
| CP021 | 136 | 2.07 | 1.97 | 1.93 |
| CP029 | 138 | 2.10 | 2.00 | 1.95 |
| CP033 | 137 | 2.12 | 2.02 | 1.96 |
| CP038 | 132 | 2.20 | 2.08 | 2.02 |
| CP044 | 136 | 2.21 | 2.09 | 2.03 |
| Compound 8 | 150 | 2.02 | 1.93 | 1.89 |

It can be seen from the data in Table 1 that the compounds CP001, CP003, CP011, CP019, CP021, CP029, CP033, CP038, and CP043 of the examples of the present disclosure have higher refractive indexes than the comparative compound 8 for the corresponding R/G/B light wavelength, and the refractive index is increased by about 3%-11%, which is conducive to the coupling extraction of light. Although Tg is slightly reduced, the operation and service life of the devices are not affected by the temperature of 130° C.

The organic compounds are employed in the organic light-emitting devices:

The embodiments of the present disclosure provide an organic light-emitting device having a structure as shown in FIGURE. The organic light-emitting device includes: a substrate 1, an anode 2 (ITO), a hole injection layer 3, a first hole transport layer 4, a second hole transport layer 5, a light-emitting layer 6, a first electron transport layer 7, a second electron transport layer 8, an electron injection layer 9, a cathode 10 (aluminum electrode), and a capping layer 11. An upward-pointing arrow in FIGURE indicates a light exiting direction. The ITO anode 2 has a thickness of 10 nm, the hole injection layer 3 has a thickness of 10 nm, the first hole transport layer 4 has a thickness of 95 nm, the second hole transport layer 5 has a thickness of 20 nm, the light-emitting layer 6 has a thickness of 30 nm, the first electron transport layer 7 has a thickness of 5 nm, the second electron transport layer 8 has a thickness of 35 nm, the electron injection layer 9 has a thickness of 1 nm, the aluminum electrode 10 has a thickness of 12 nm, and the capping layer 11 has a thickness of 70 nm.

Application Example 1

An organic light-emitting device 01 is manufactured by the following steps:

1) a glass substrate 1 was cut into a size of 50 mm×50 mm×0.7 mm, ultrasonically cleaned respectively in isopropyl alcohol and deionized water for 30 minutes, and then exposed in ozone for 10 minutes; the obtained glass substrate with an ITO anode 2 was mounted on a vacuum deposition apparatus;

2) under a vacuum degree of $2\times10^{-6}$ Pa, the compound 1 was deposited on the ITO anode layer 2 by vacuum evaporation to form the hole injection layer 3, which has a thickness of 10 nm;

3) N,N'-diphenyl-N,N'-(1-naphthyl)-1,1'-biphenyl-4,4'-diamine (compound 2) was deposited on the hole injection layer 3 by vacuum evaporation to form the first hole transport layer 4, which has a thickness of 95 nm;

4) the compound 3 was vacuum evaporated onto the first hole transport layer 4 to form the second hole transport layer 5, which has a thickness of 20 nm;

5) the compound 4 used as a host material and the compound 5 used as a dopant in a doping ratio of 5% (mass ratio) were co-deposited on the second hole transport layer 5 to form a light-emitting layer 6 having a thickness of 30 nm;

6) compound 6 was vacuum evaporated onto the light-emitting layer 6 to form the first electron transport layer 7 having a thickness of 5 nm;

7) compound 7 was vacuum evaporated onto the first electron transport layer 7 to form the second electron transport layer 8 having a thickness of 35 nm; and 8) LiF was vacuum evaporated onto the second electron transport layer 8 to form an electron injection layer 9, which has a thickness of 1 nm;

9) an aluminum electrode was vacuum evaporated onto the electron injection layer 9 to form a cathode 10, which has a thickness of 12 nm; and 10) CP001 according to the present disclosure was vacuum evaporated onto the cathode 10 to form a capping layer 11, having a thickness of 70 nm.

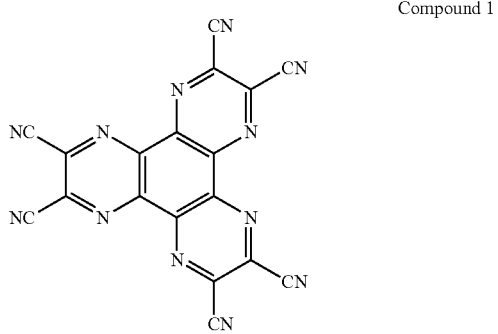

Compound 1

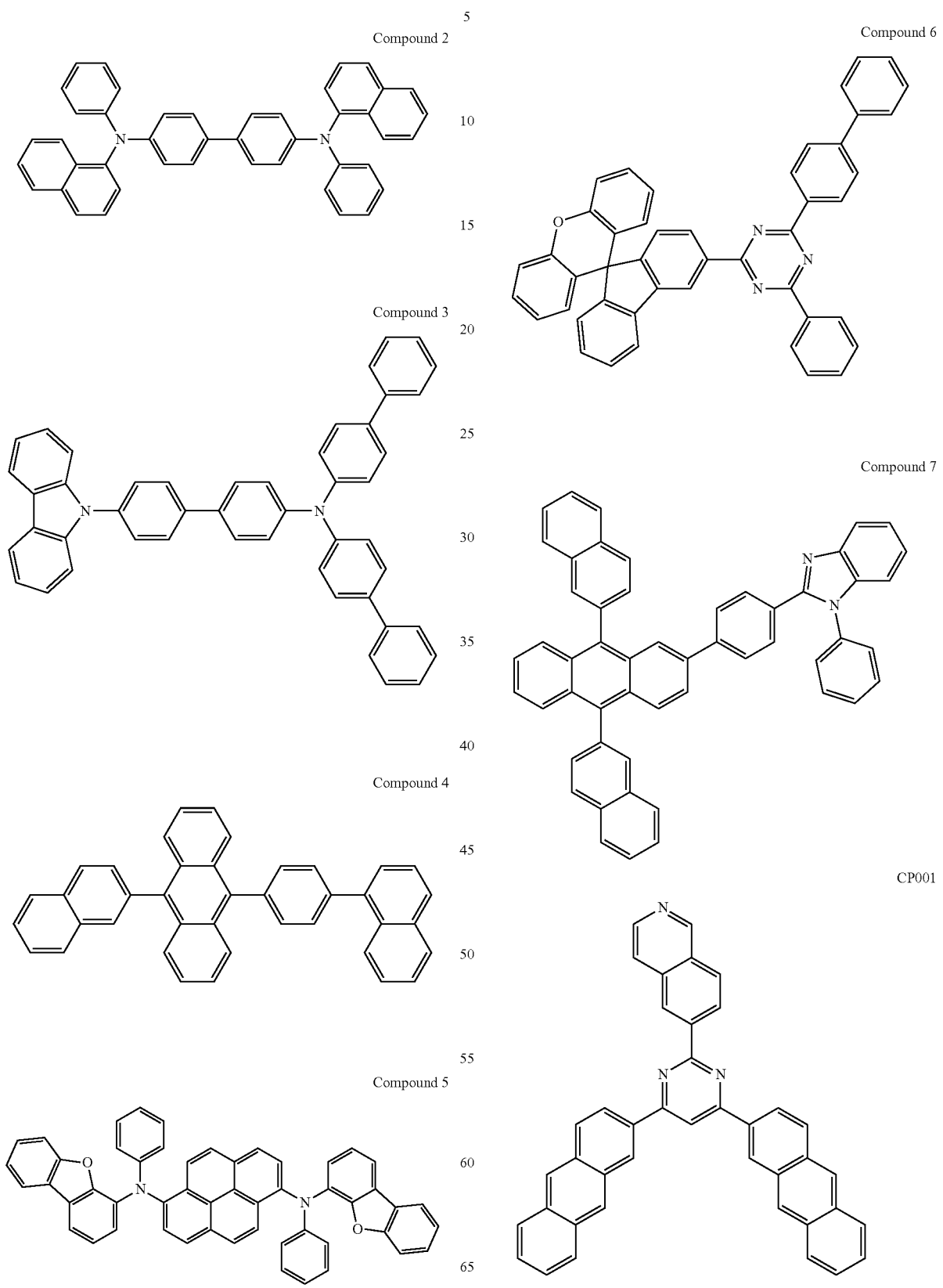

Application Example 2

An organic light-emitting device 02 was prepared by the same steps as in Application Example 1, except that compound CP001 was replaced with compound CP003.

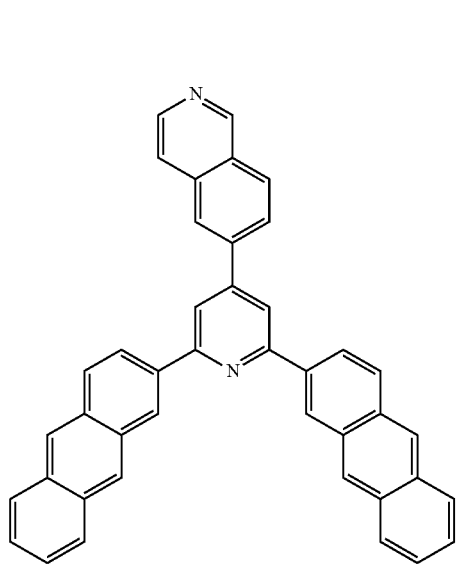
CP003

Application Example 3

An organic light-emitting device 03 was prepared by the same steps as in Application Example 1, except that compound CP001 was replaced with compound CP011.

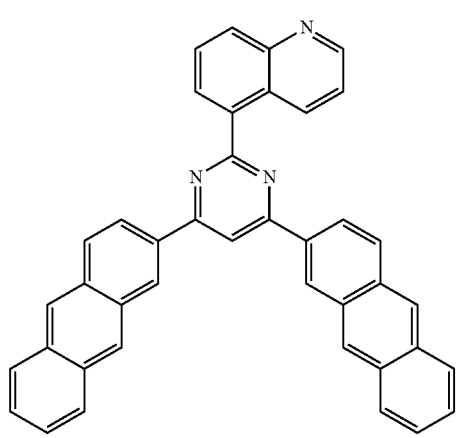
CP011

Application Example 4

An organic light-emitting device 04 was prepared by the same steps as in Application Example 1, except that compound CP001 was replaced with compound CP019.

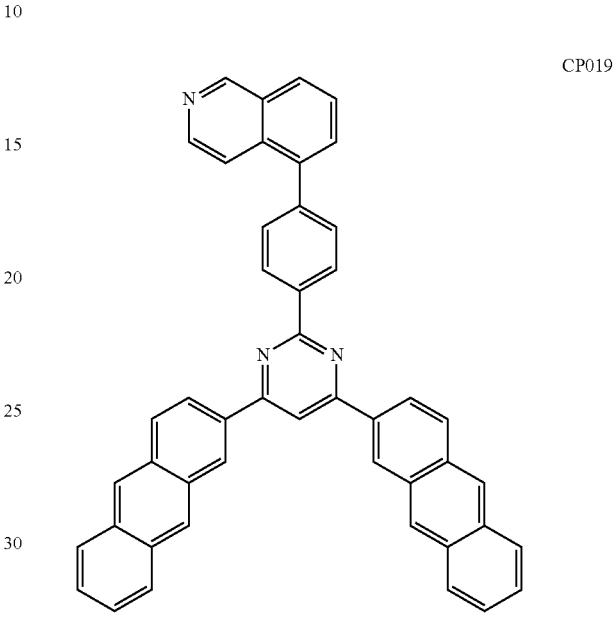
CP019

Application Example 5

An organic light-emitting device 05 was prepared by the same steps as in Application Example 1, except that compound CP001 was replaced with compound CP021.

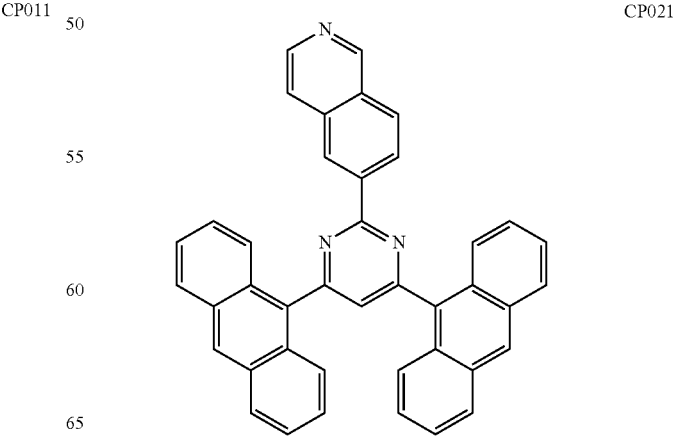
CP021

Application Example 6

An organic light-emitting device 06 was prepared by the same steps as in Application Example 1, except that compound CP001 was replaced with compound CP029.

Application Example 8

An organic light-emitting device 08 was prepared by the same steps as in Application Example 1, except that compound CP001 was replaced with compound CP038.

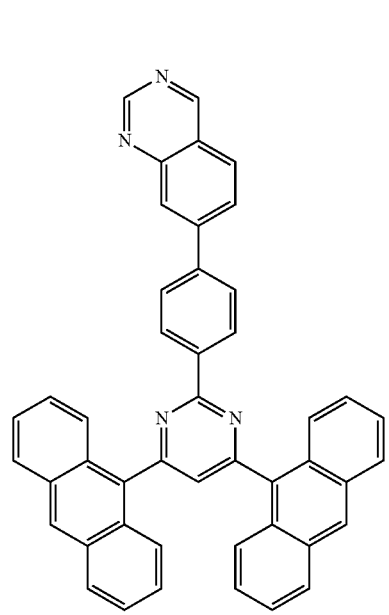

CP029

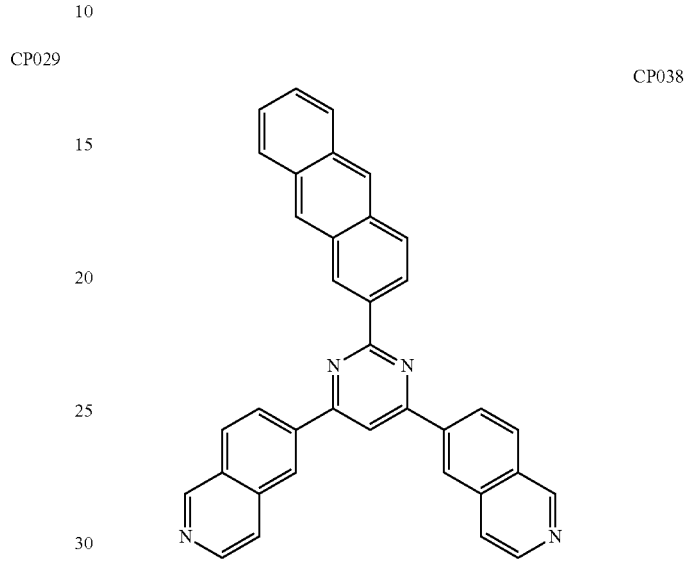

CP038

Application Example 9

An organic light-emitting device 09 was prepared by the same steps as in Application Example 1, except that compound CP001 was replaced with compound CP044.

Application Example 7

An organic light-emitting device 07 was prepared by the same steps as in Application Example 1, except that compound CP001 was replaced with compound CP033.

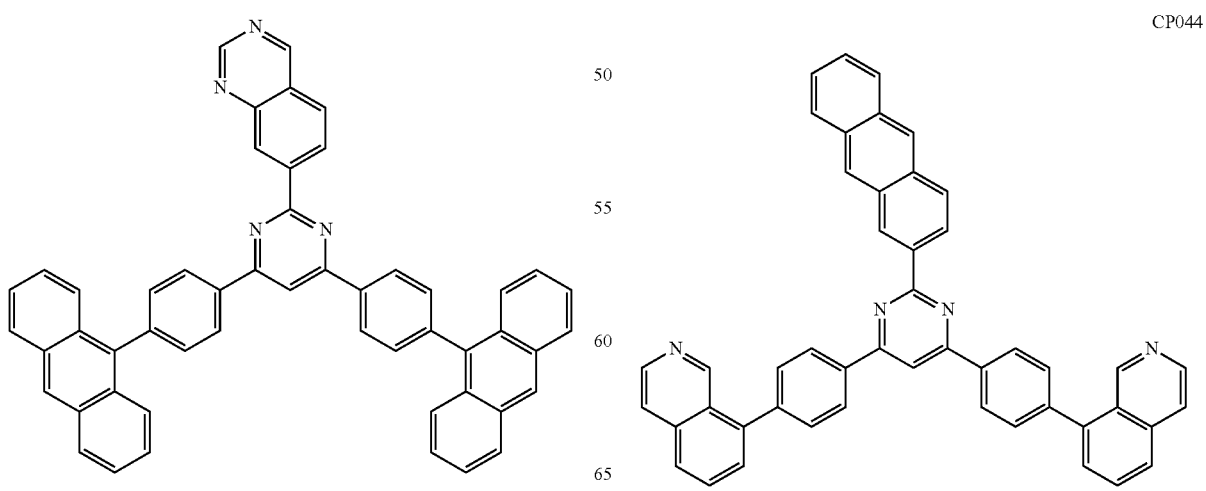

CP033

CP044

Comparative Example 1

An organic light-emitting device 10 was prepared by the same steps as in Application Example 1, except that compound CP001 was replaced with compound 8.

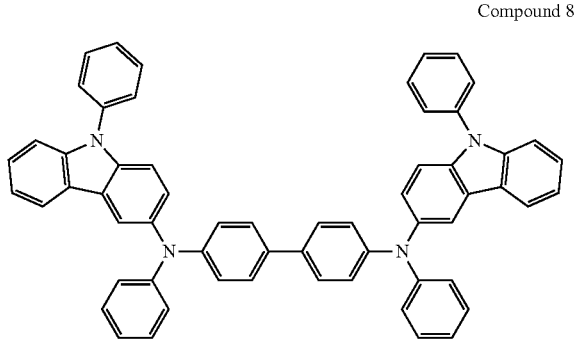

Compound 8

TABLE 2

Test results of luminous performances of the devices

| No. | Material of CPL | Driving voltage (V) | CE (cd/A) | Life time LT95 |
|---|---|---|---|---|
| Organic light-emitting device 01 | CP001 | 3.86 | 6.5 | 51 |
| Organic light-emitting device 02 | CP003 | 3.93 | 6.9 | 53 |
| Organic light-emitting device 03 | CP011 | 3.90 | 7.4 | 49 |
| Organic light-emitting device 04 | CP019 | 3.87 | 6.8 | 48 |
| Organic light-emitting device 05 | CP021 | 3.95 | 7.2 | 52 |
| Organic light-emitting device 06 | CP0029 | 3.87 | 7.6 | 47 |
| Organic light-emitting device 07 | CP033 | 3.98 | 6.6 | 54 |
| Organic light-emitting device 08 | CP038 | 3.82 | 7.5 | 50 |
| Organic light-emitting device 09 | CP044 | 3.91 | 7.8 | 53 |
| Organic light-emitting device 10 | compound 8 | 4.12 | 5.9 | 42 |

As can be seen from the data in Table 2, Application Example 1 to Application Example 9 all have lower driving voltage, better luminous efficiency, and longer life time LT95 than Comparative Example 1, which is mainly attributed to the higher refractive index of the compounds according to the present disclosure. In accordance with the law of refraction, with an increase in the refractive index, a direction of coupling extraction of light tends to be perpendicular to the substrate, which is favorable for the extraction of light.

In another aspect, the embodiments of the present disclosure further provide a display apparatus, which includes the organic light-emitting display panel as described above.

In the present disclosure, the organic light-emitting device can be an OLED, which may be used in the organic light-emitting display apparatus. The organic light-emitting display apparatus may be display screens of mobile phone, computer, liquid crystal television, smart watch, smart car, VR or AR helmet, or other smart devices.

What is claimed is:

1. An organic compound being one of the following compounds:

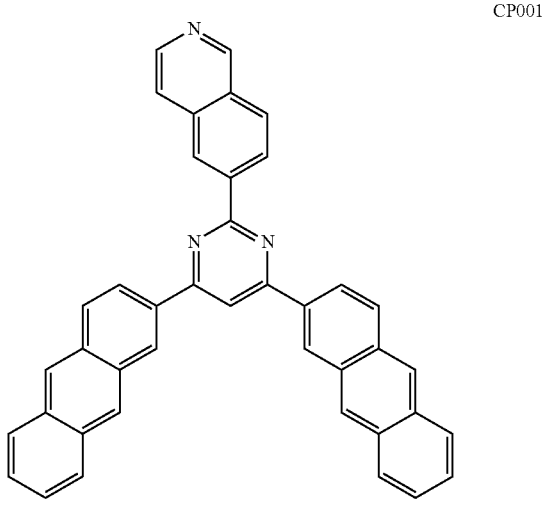 [SMILES: c1ccc2cc3cc(-c4cc(-c5ccc6cnccc6c5)cc(-c5ccc6cc7ccccc7cc6c5)n4)ccc3cc2c1]

CP001

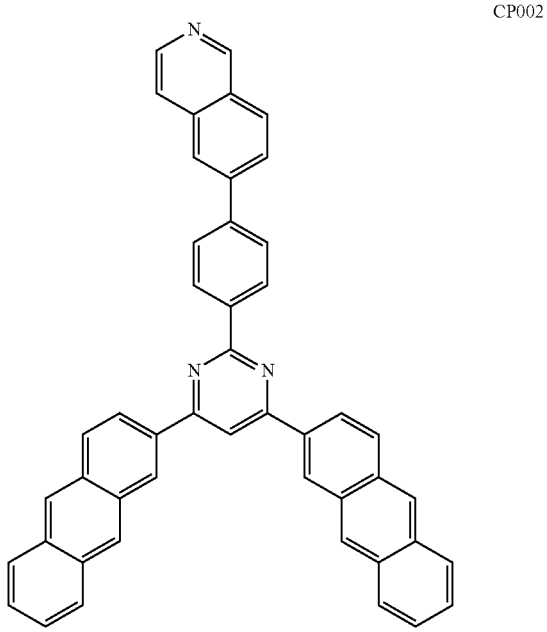

CP002

-continued
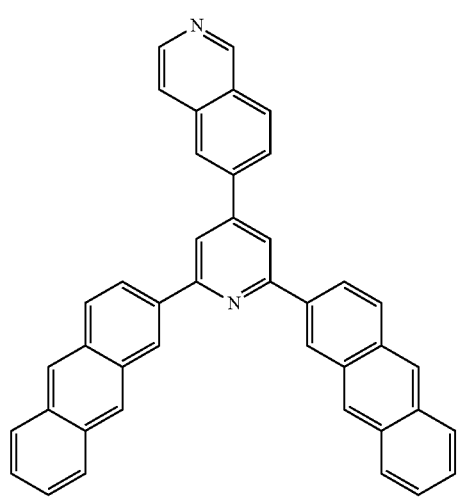
CP003
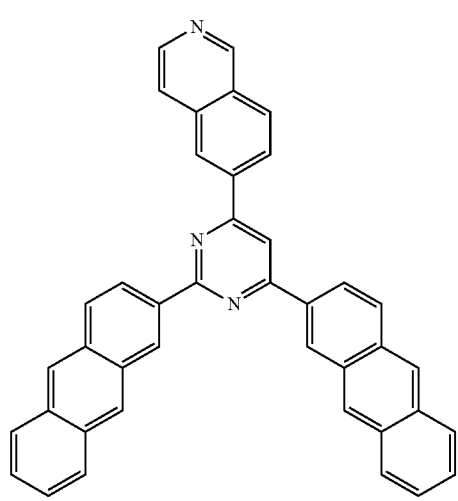
CP004
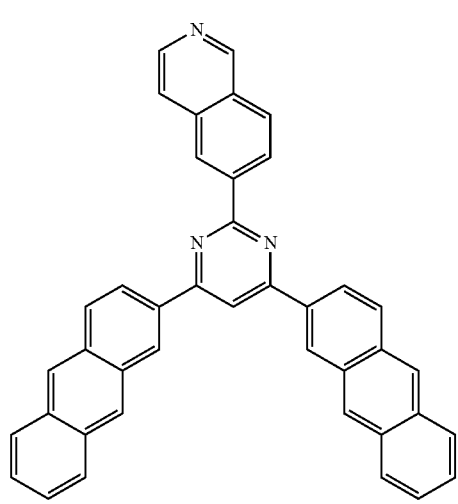
CP005
-continued
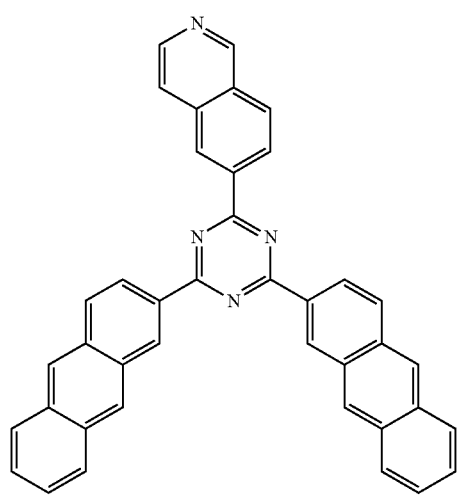
CP006
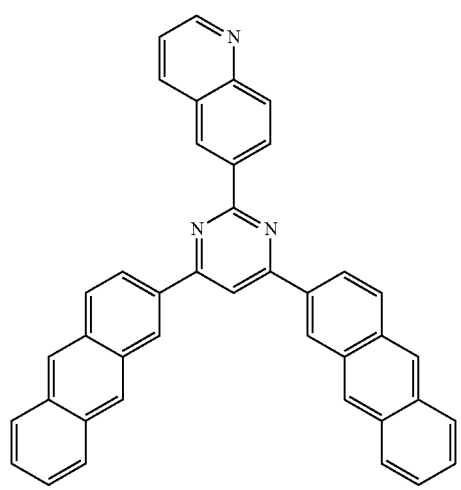
CP007
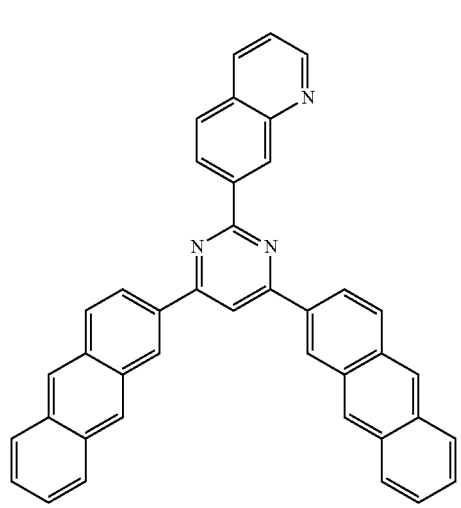
CP008

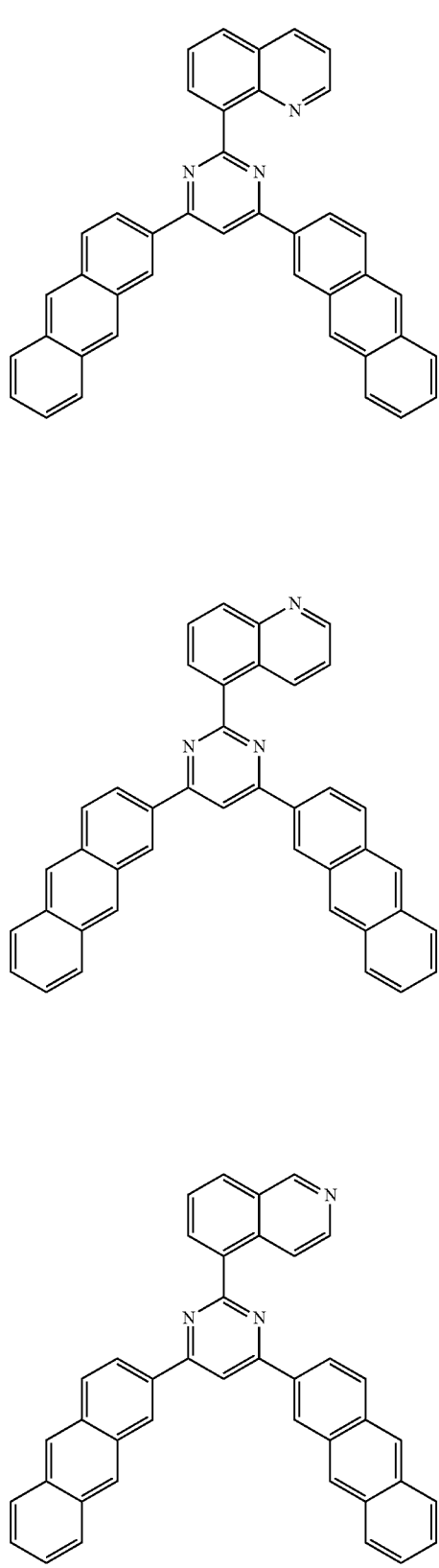
CP009
CP010
CP011
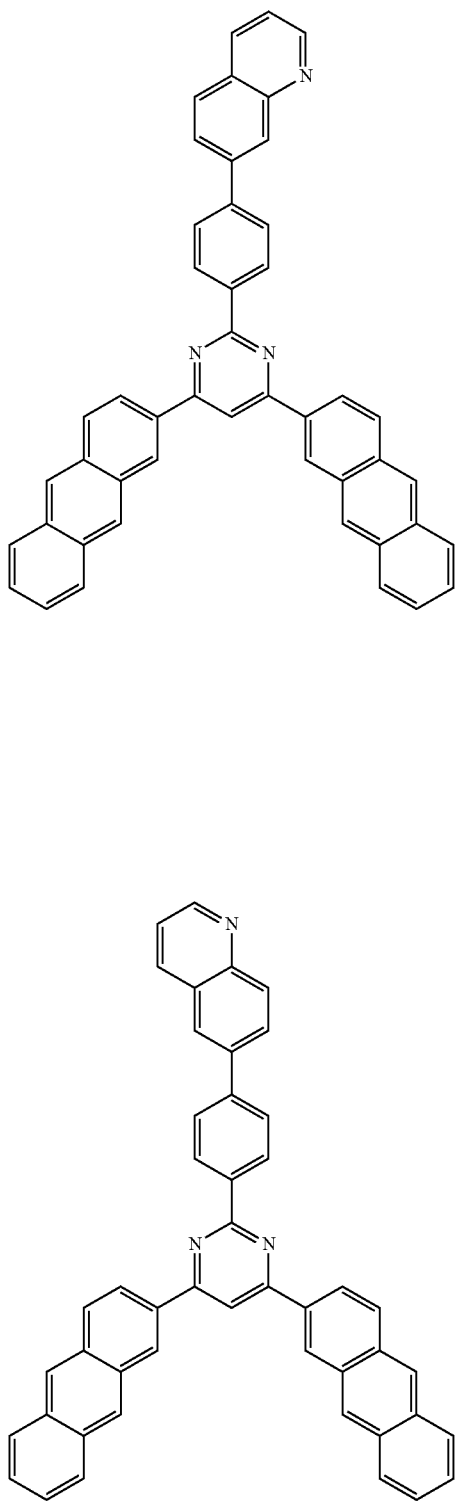
CP012
CP013

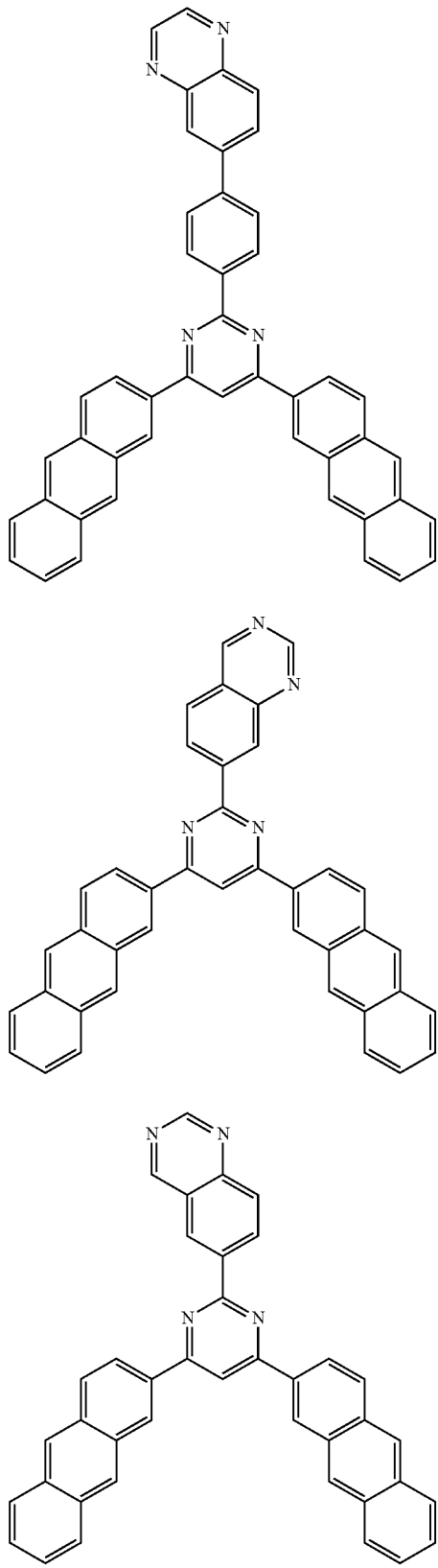
CP014
CP015
CP016
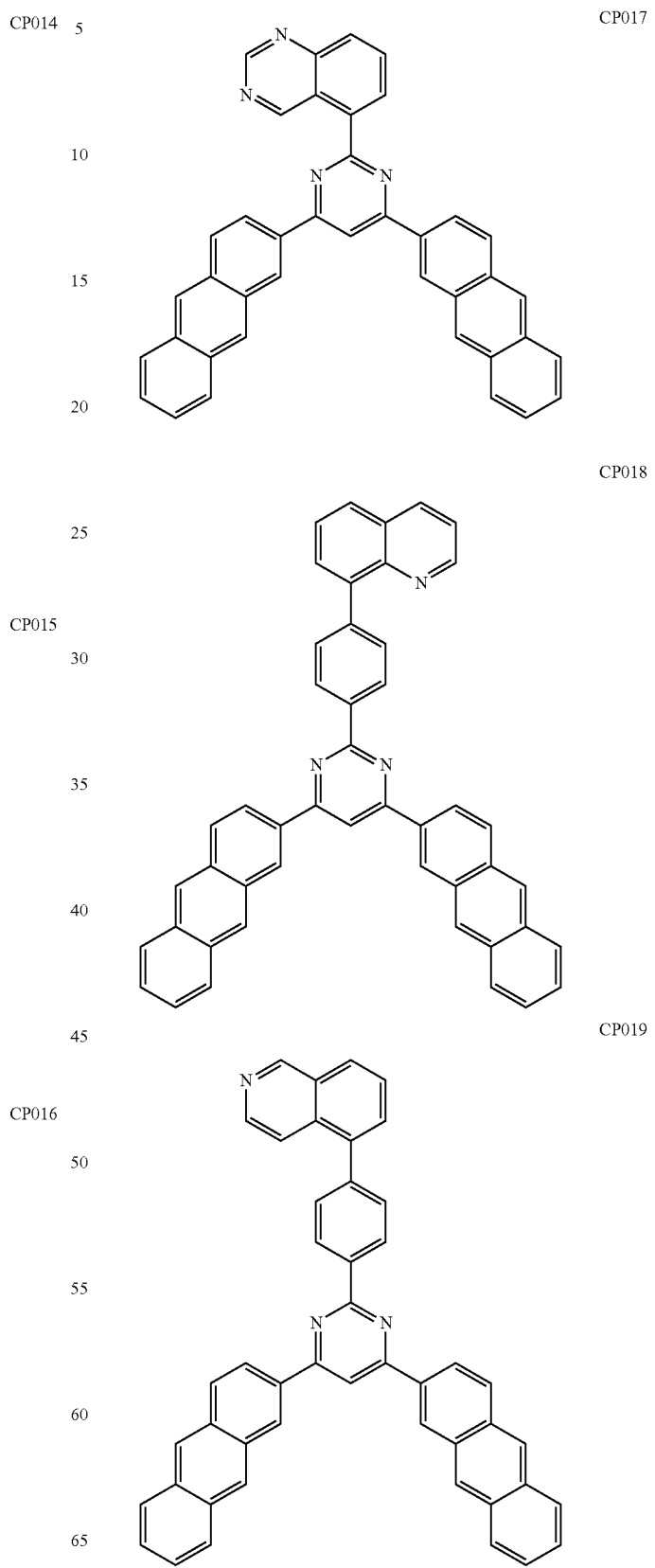
CP017
CP018
CP019

-continued
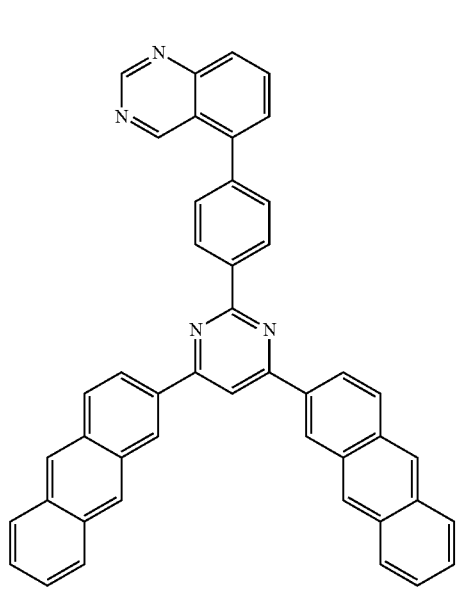 CP020
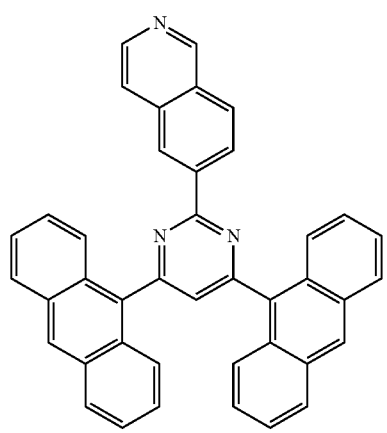 CP021
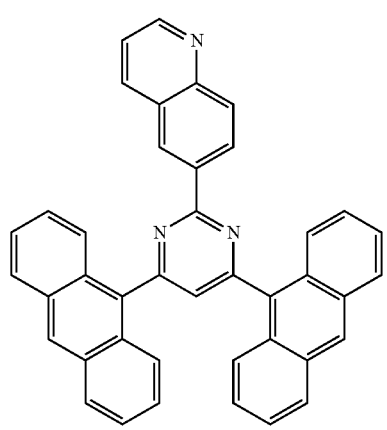 CP022
-continued
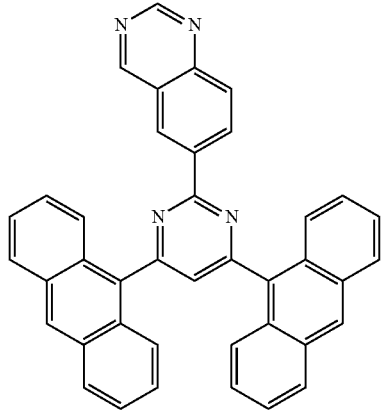 CP023
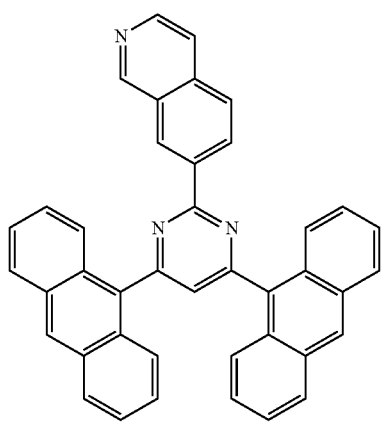 CP024
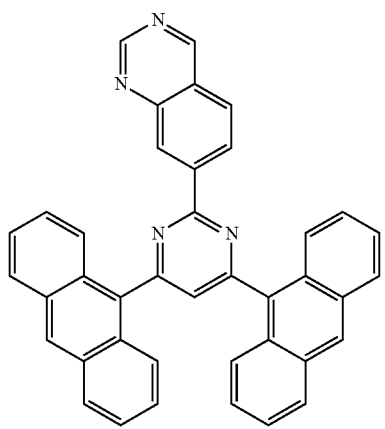 CP025

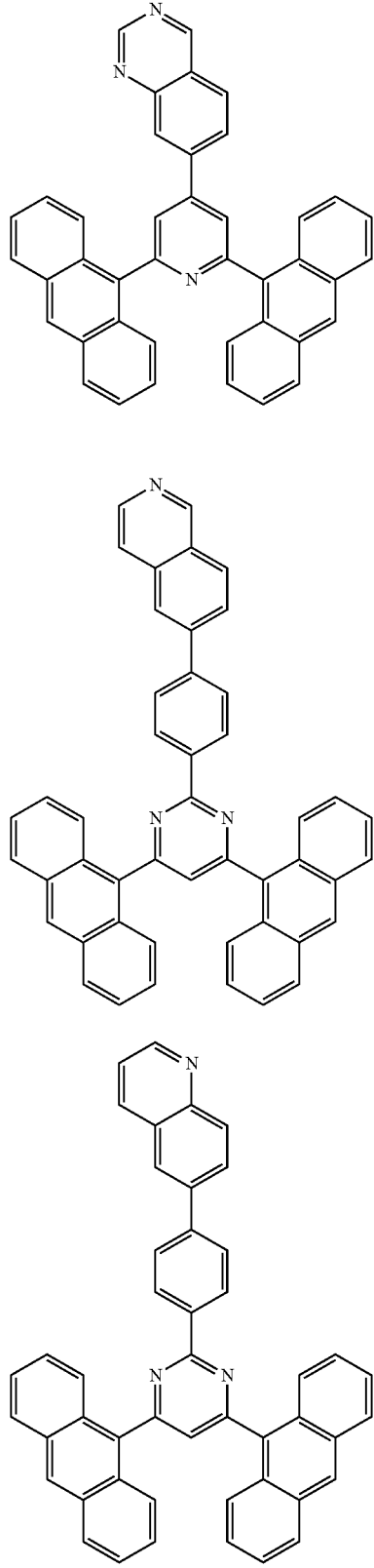
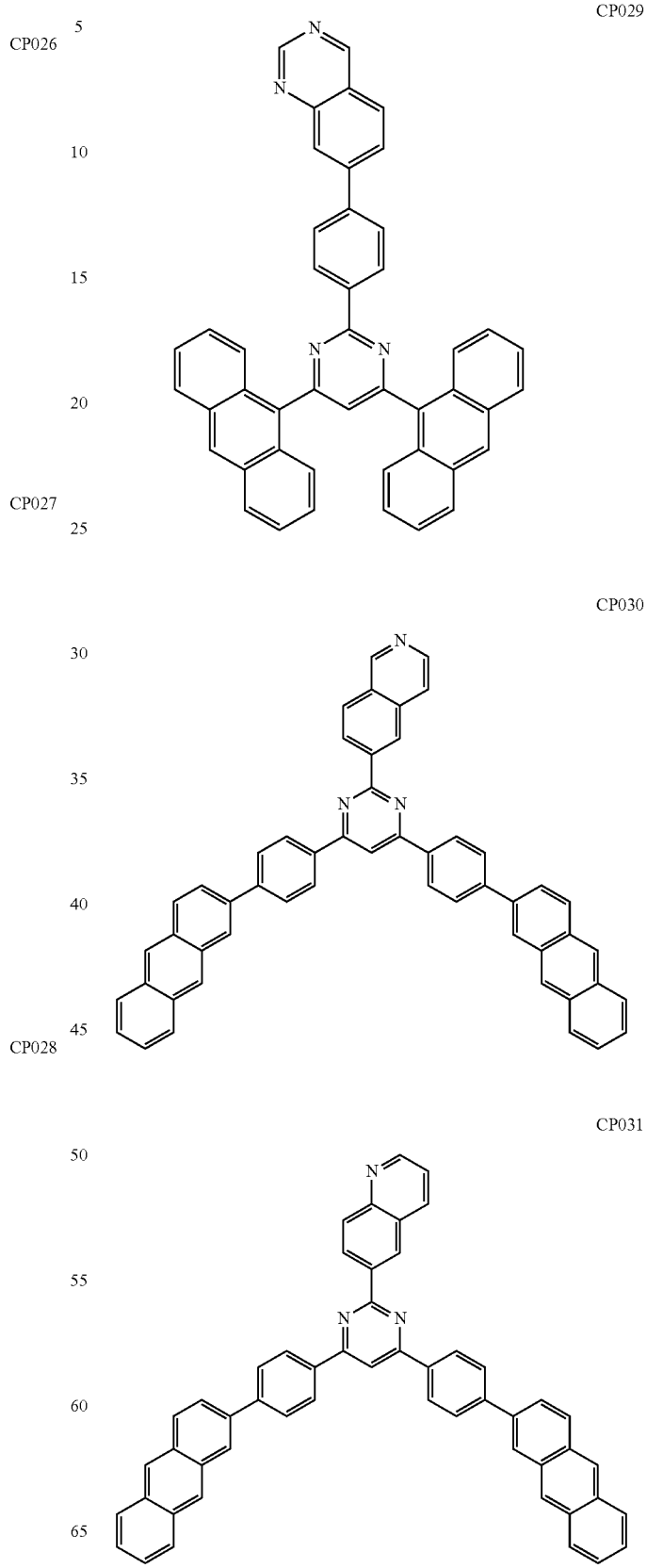

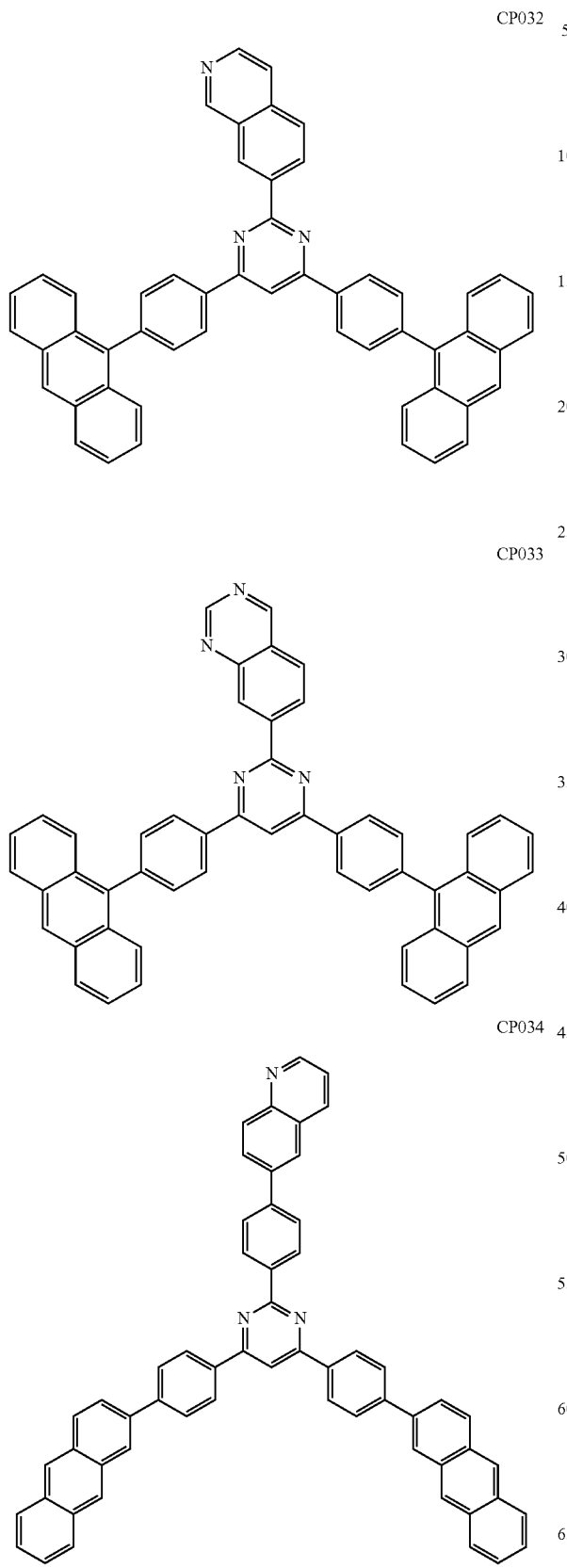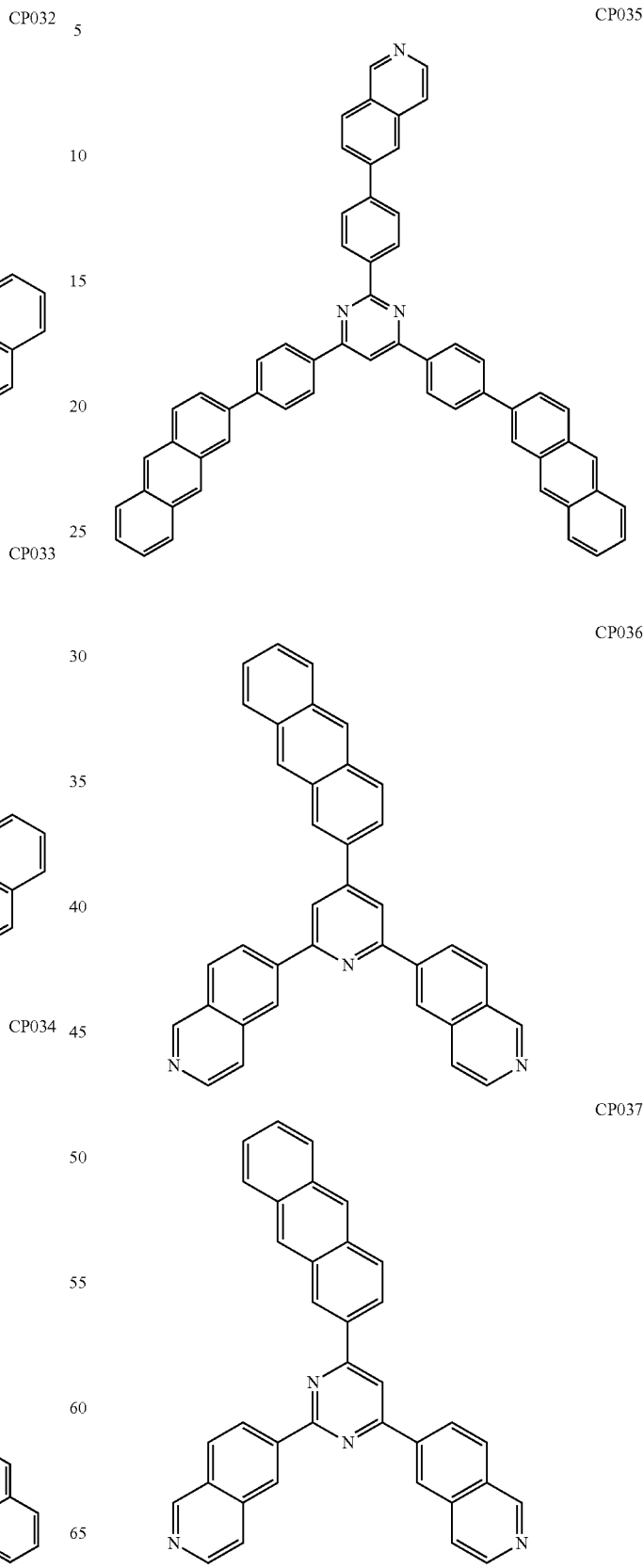

CP038
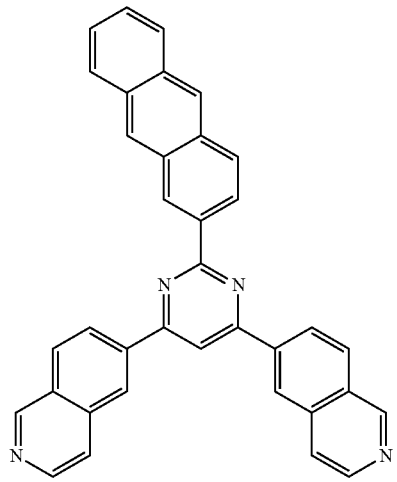
CP039
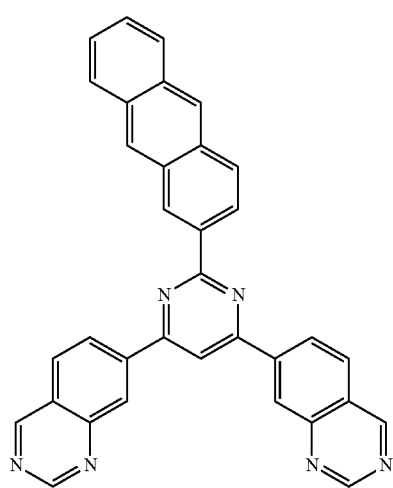
CP041
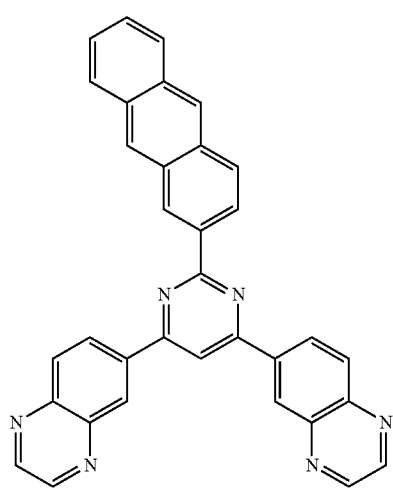
CP042
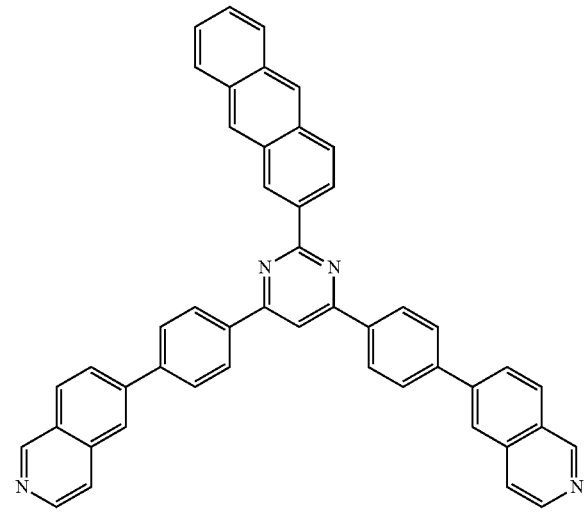
CP043
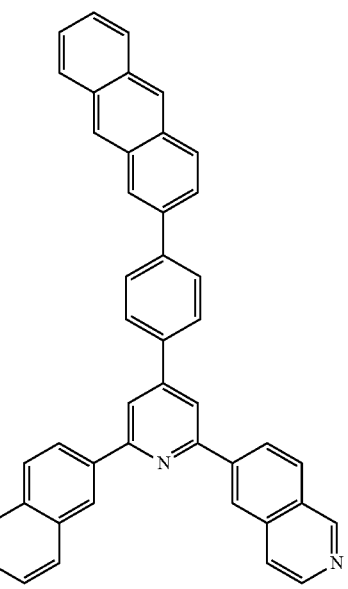
CP044
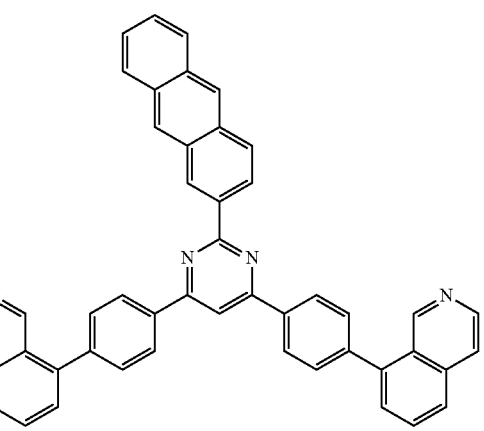

CP045
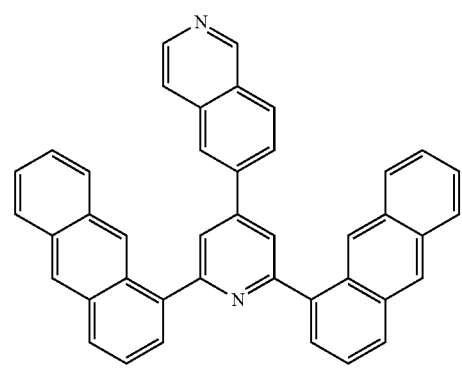
CP046
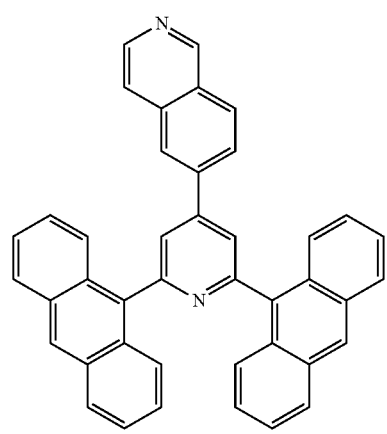
CP047
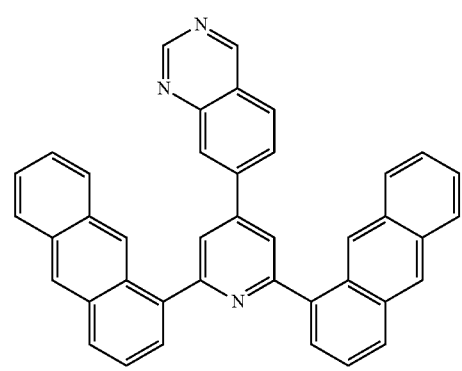
CP048
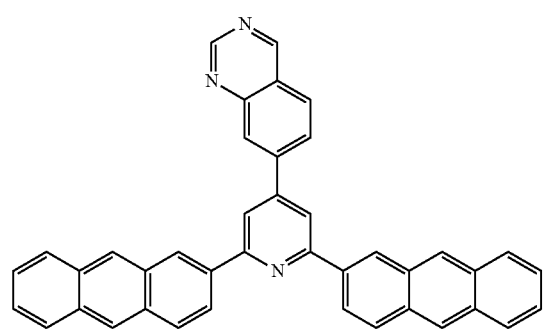
-continued
CP049
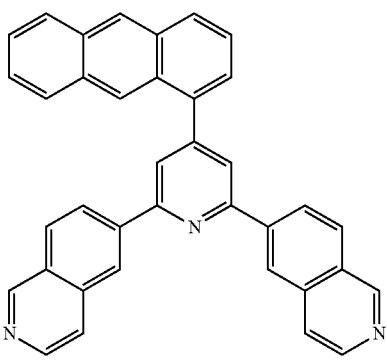
CP050
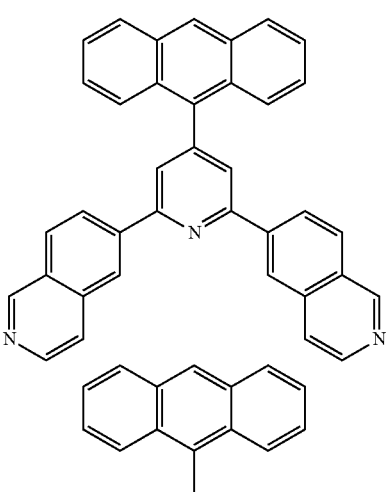
CP051
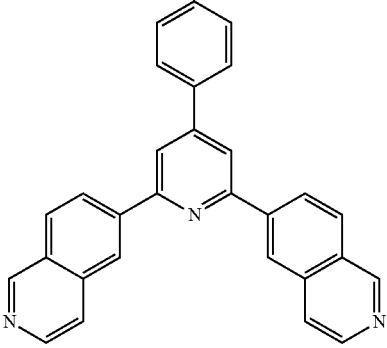
CP052
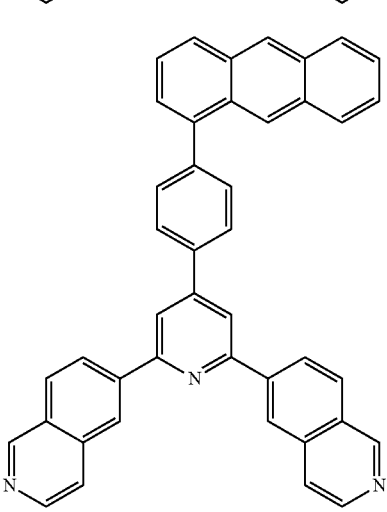

-continued
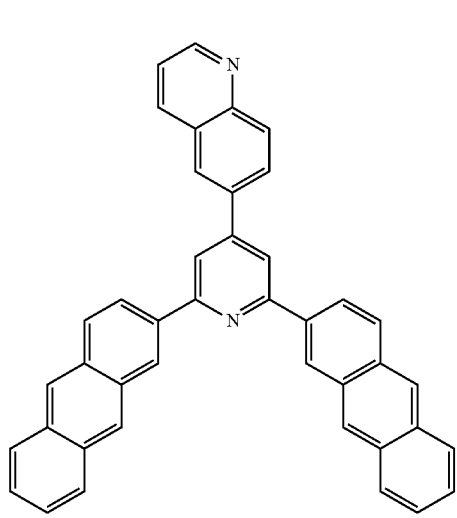
CP053
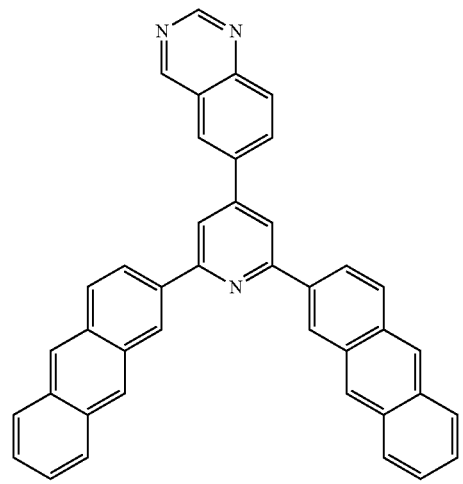
CP056
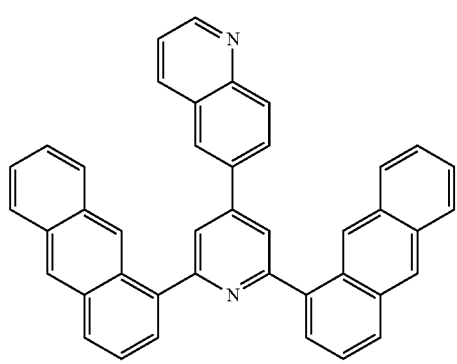
CP054
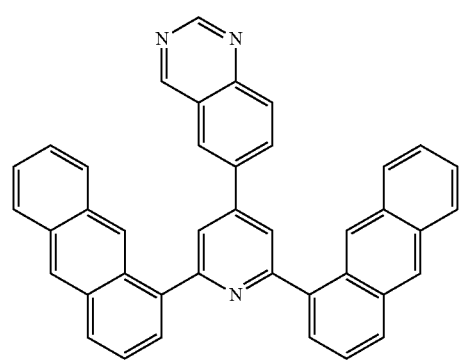
CP057
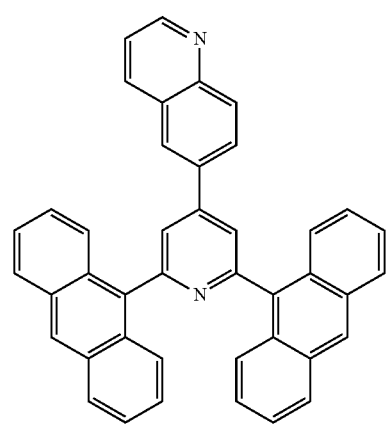
CP055
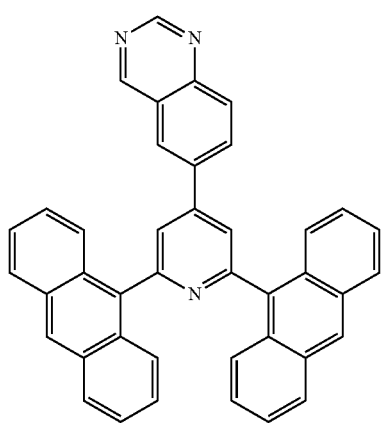
CP058

-continued
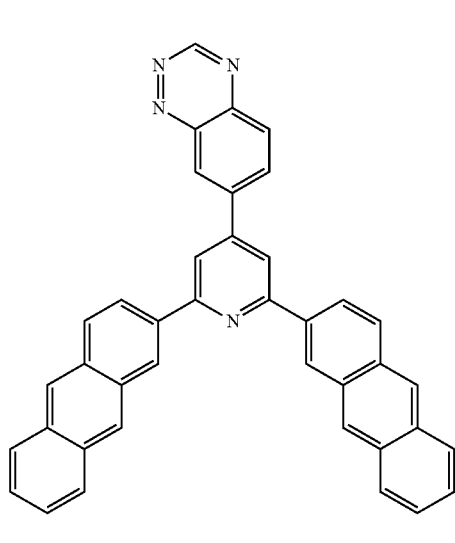 CP059
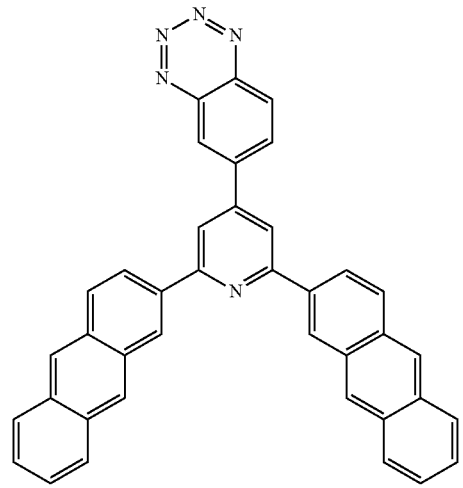 CP062
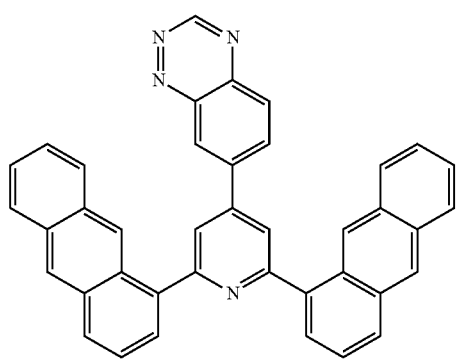 CP060
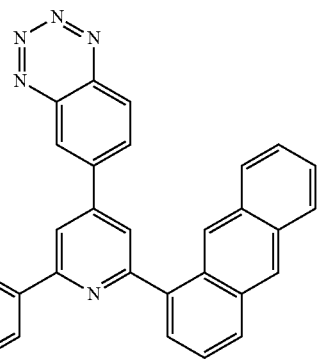 CP063
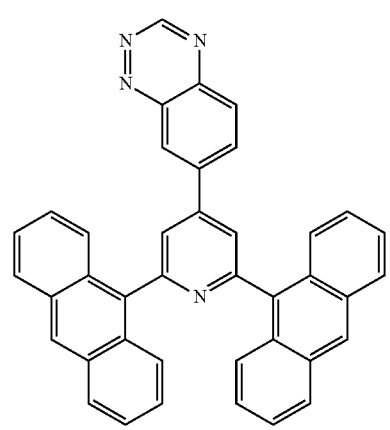 CP061
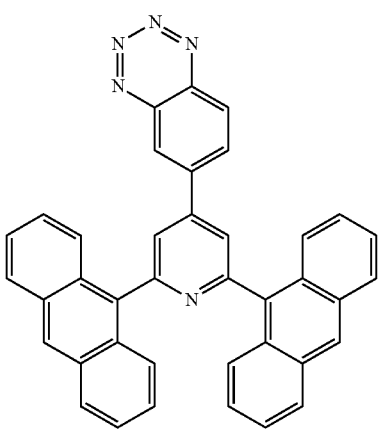 CP064

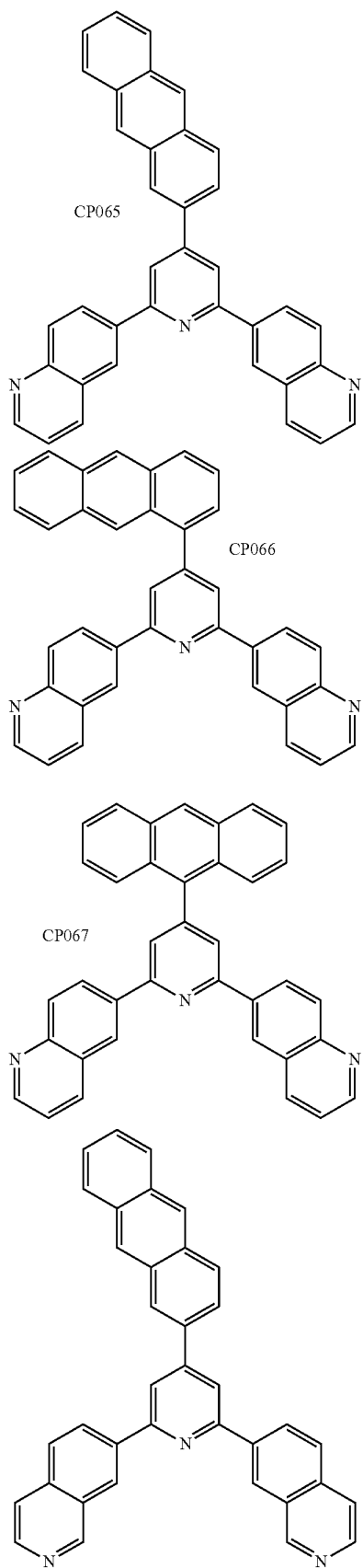
CP065
CP066
CP067
CP068
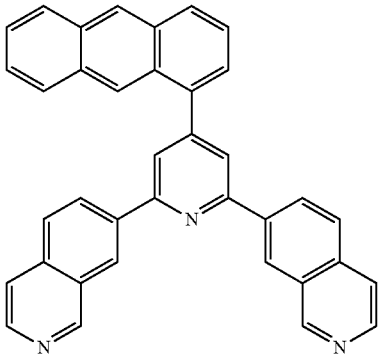
CP069
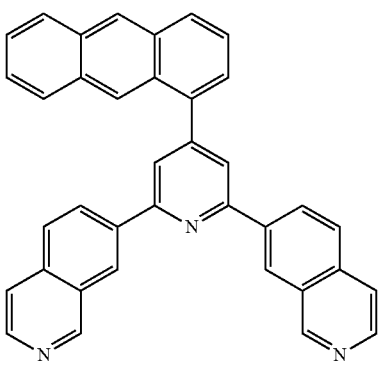
CP070
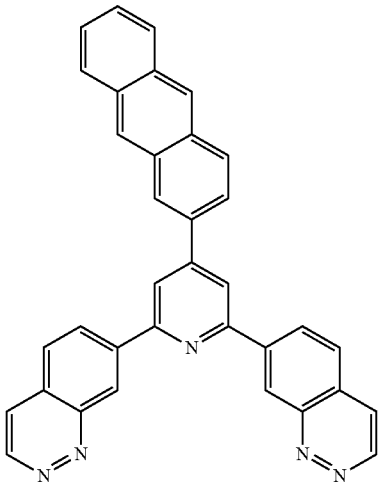
CP071
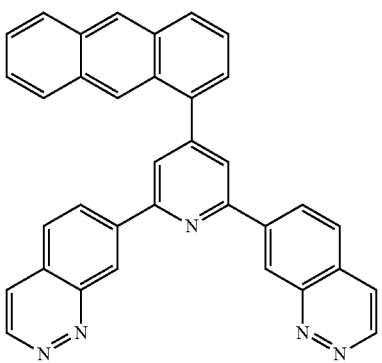
CP072

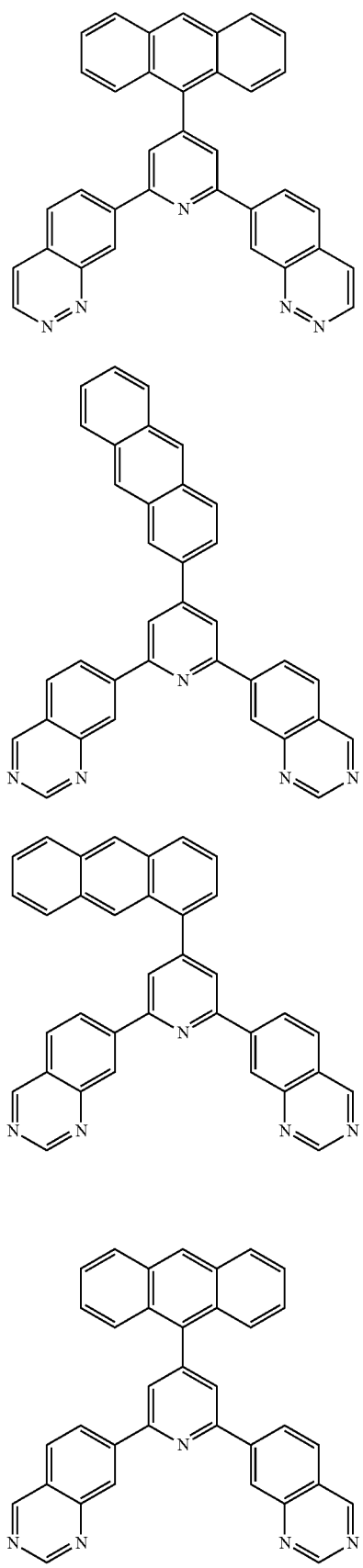
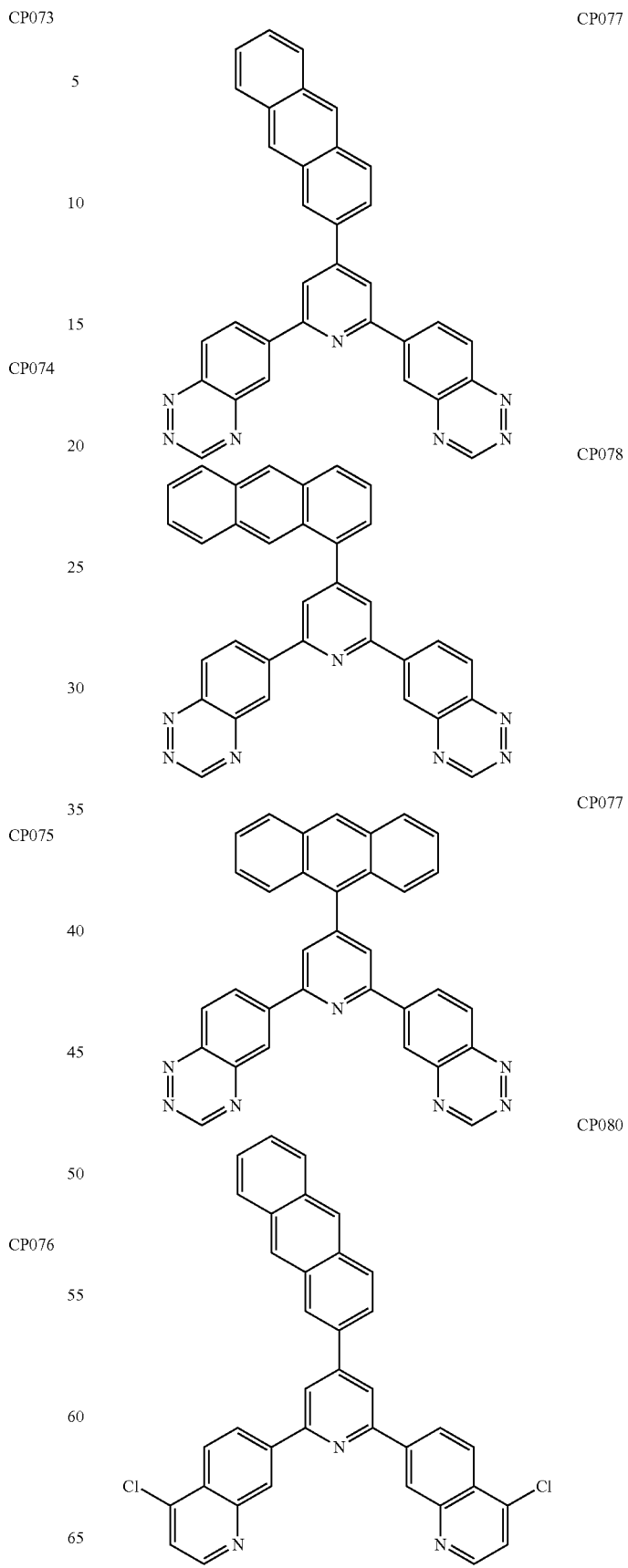

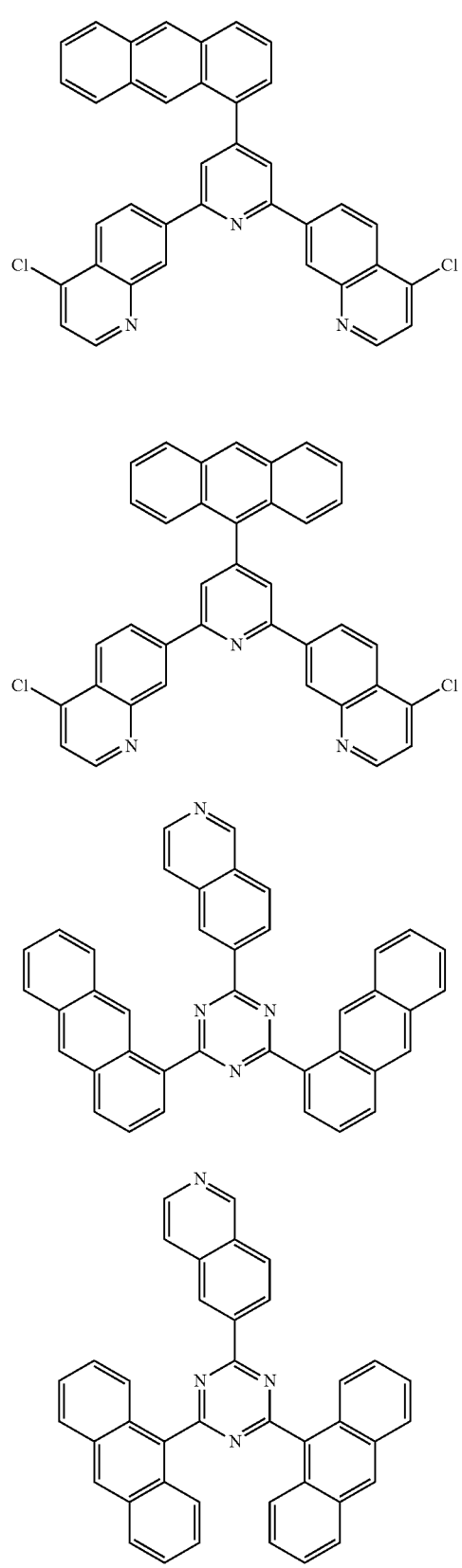
CP081
CP082
CP083
CP084
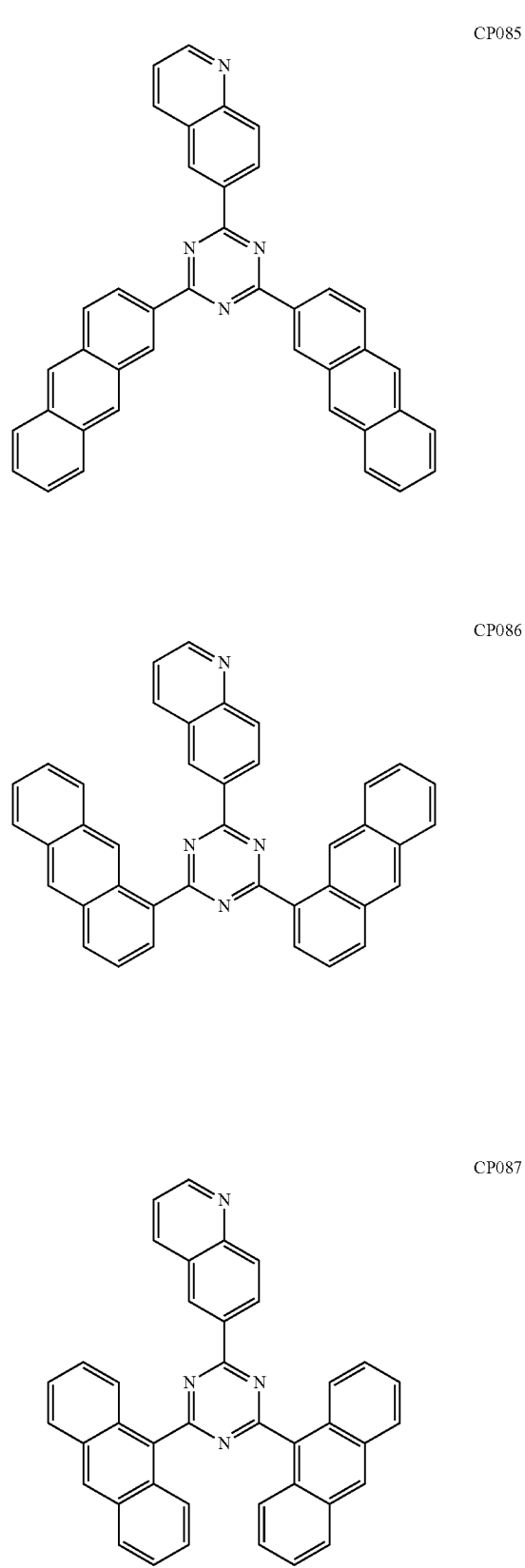
CP085
CP086
CP087

-continued
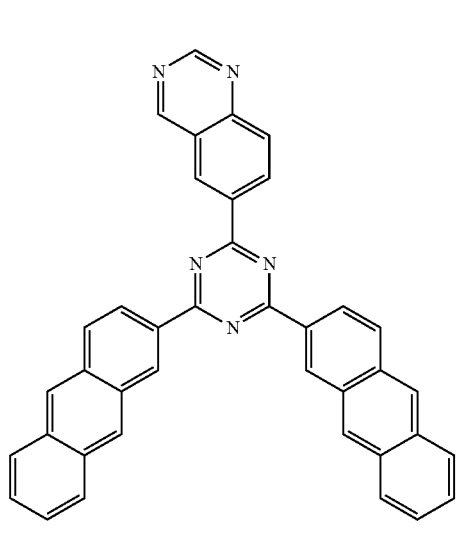
CP088
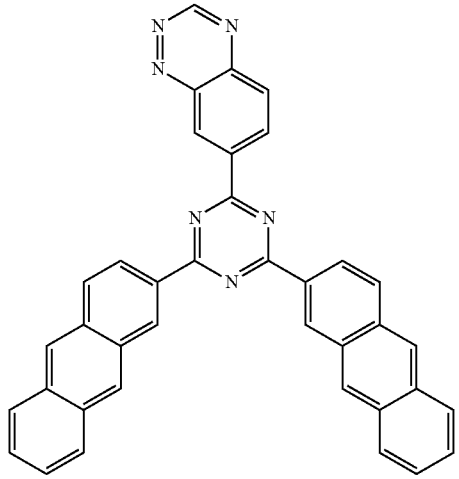
CP091
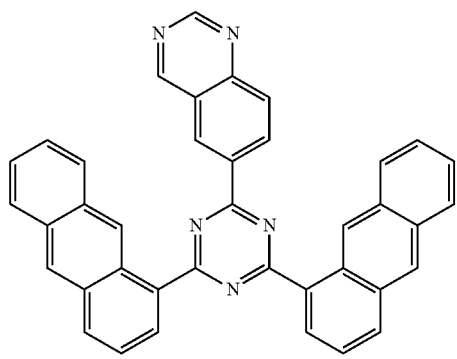
CP089
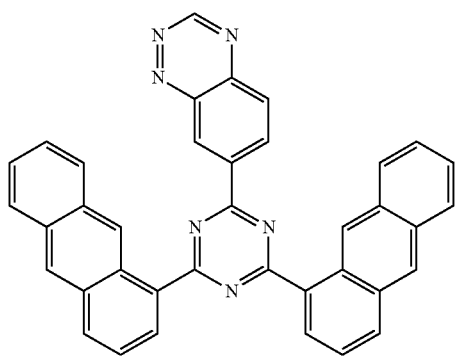
CP092
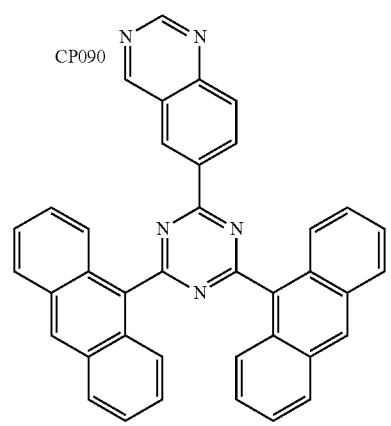
CP090
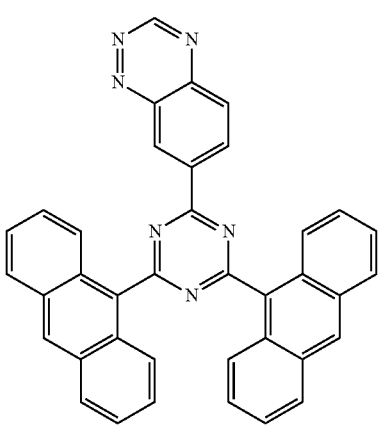
CP093

CP094
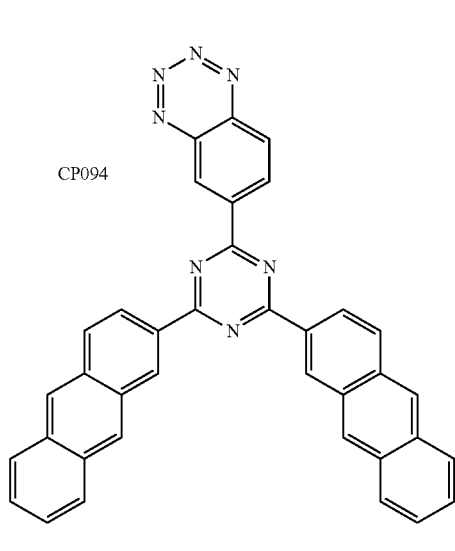
CP095
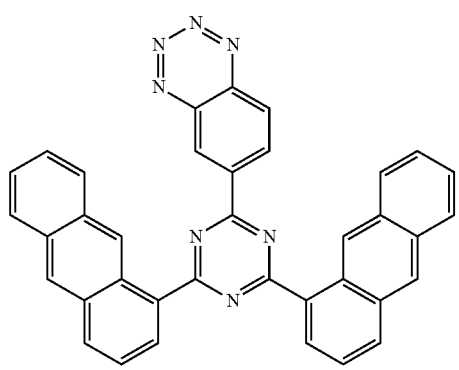
CP096
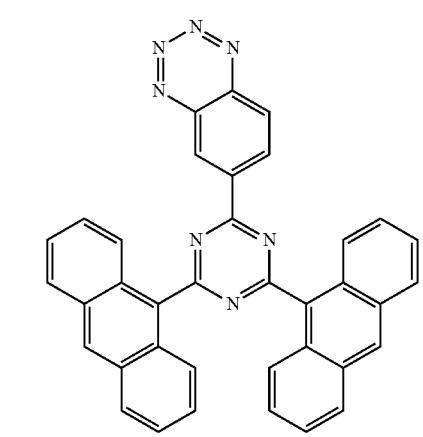
CP097
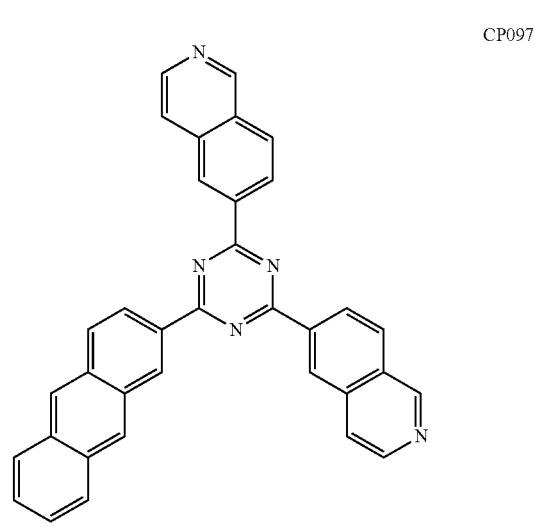
CP098
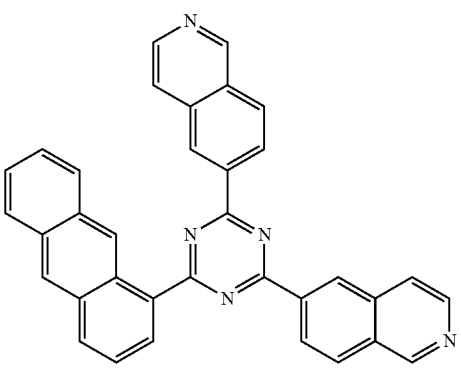
CP099
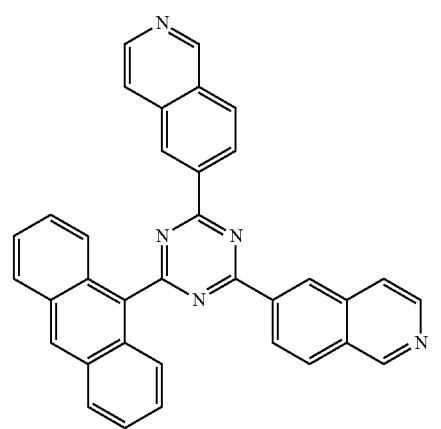

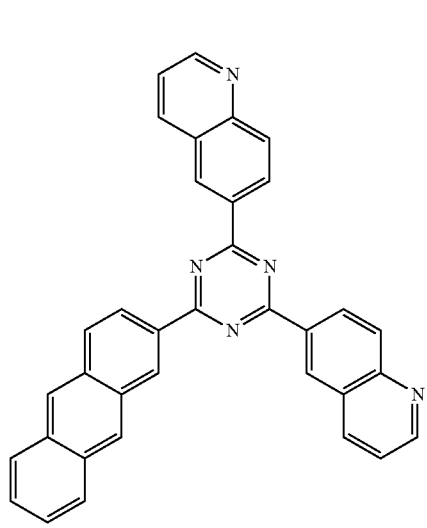
CP100
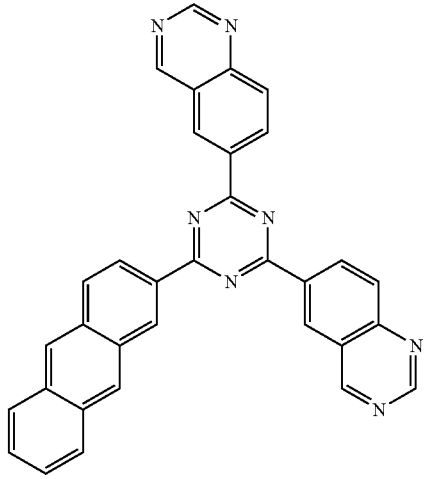
CP103
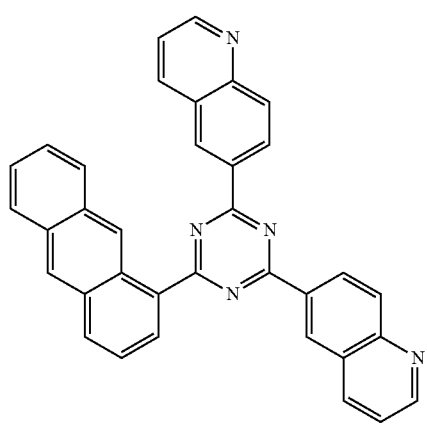
CP101
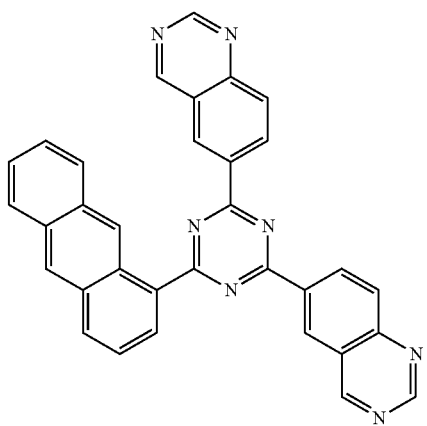
CP104
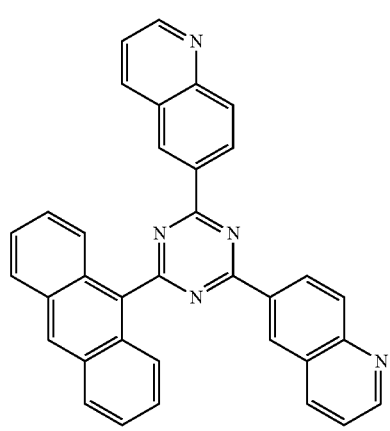
CP102
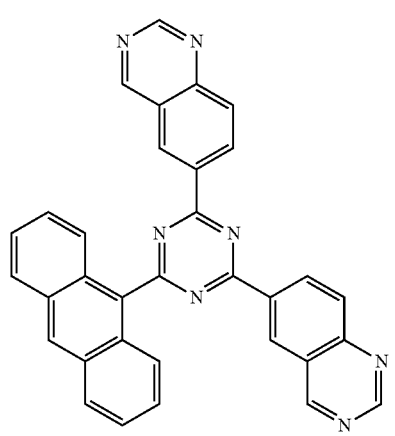
CP105

-continued
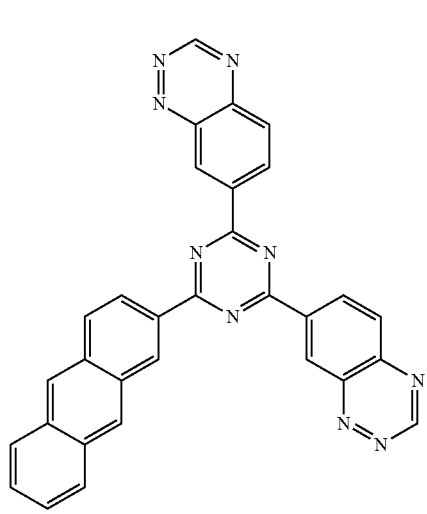
CP106
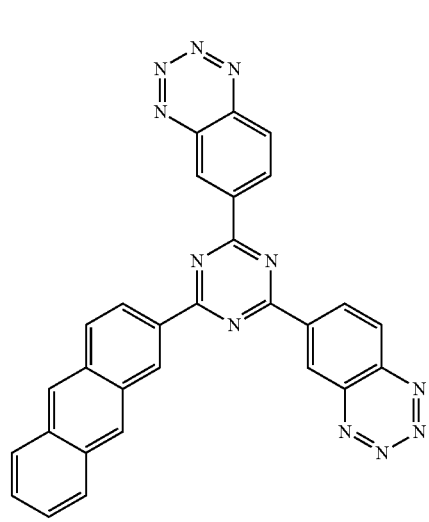
CP109
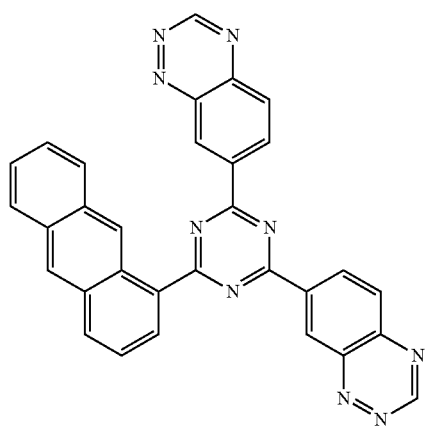
CP107
CP110
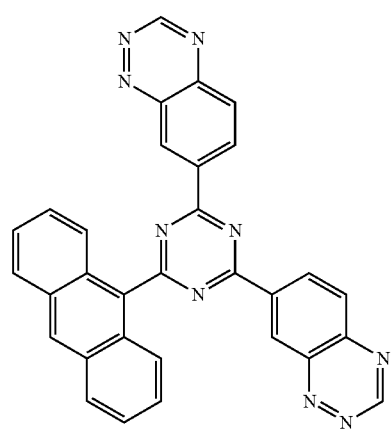
CP108
CP111

CP112
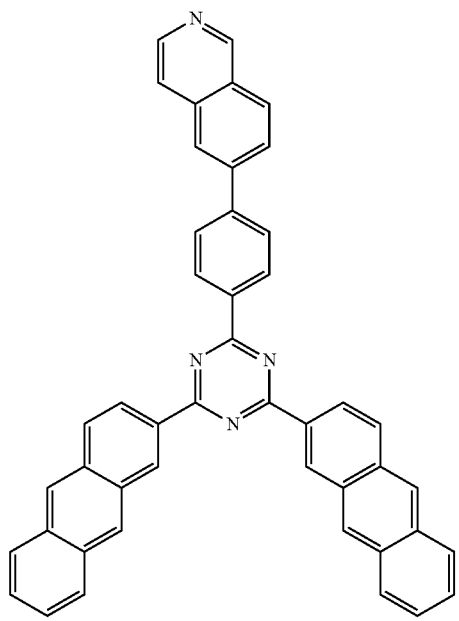
CP113
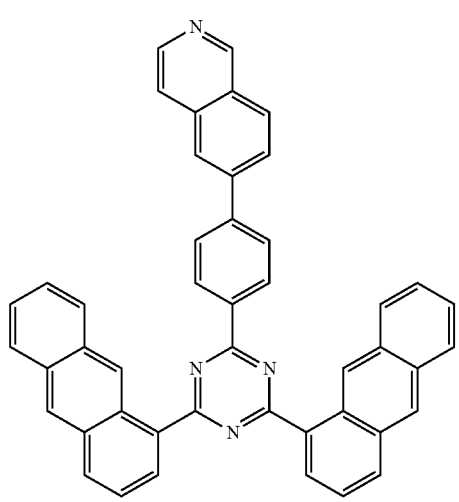
CP114
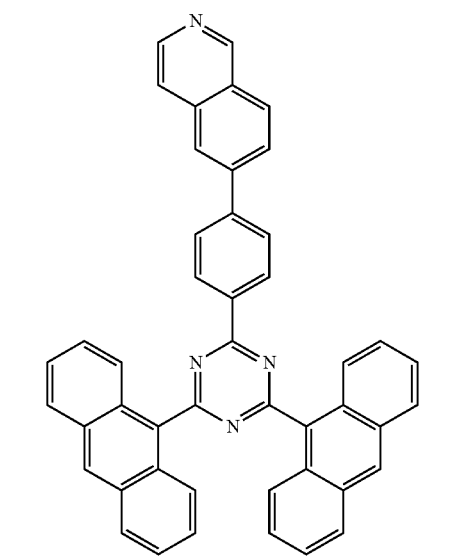
CP115
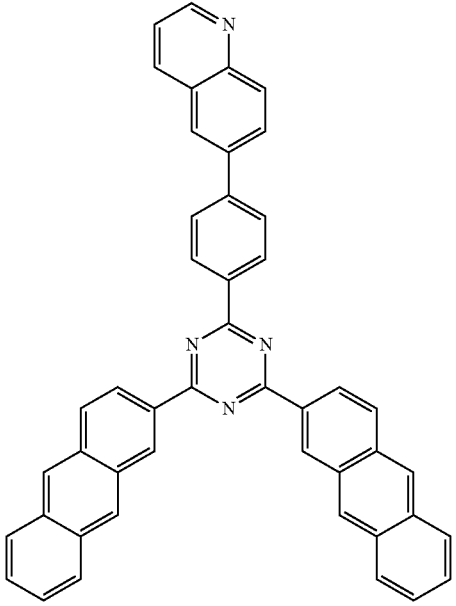
CP116
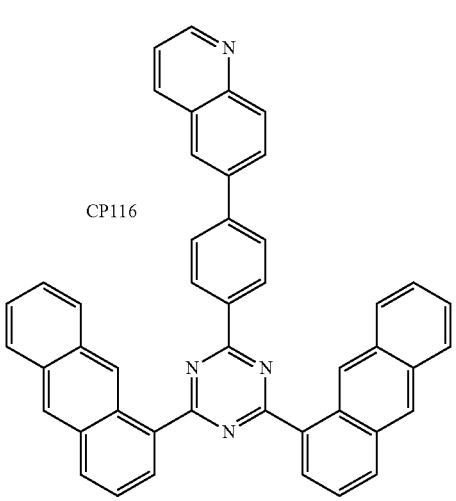
CP117
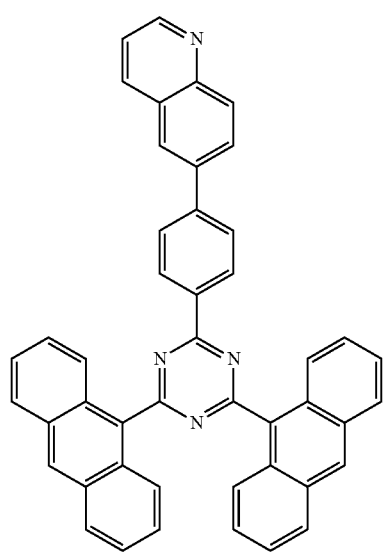

CP118
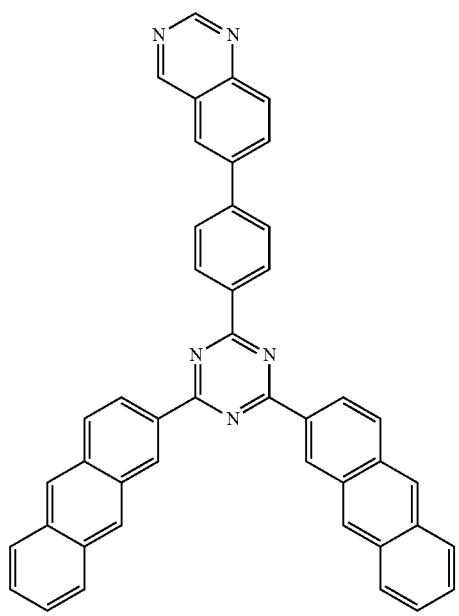
CP119
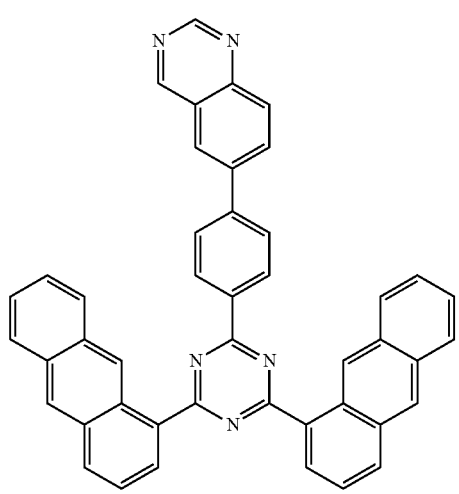
CP120
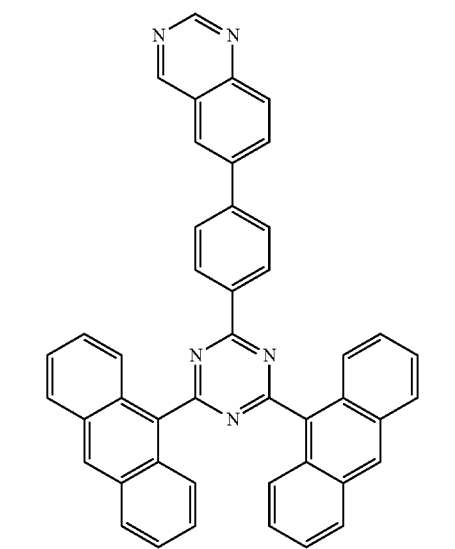
CP121
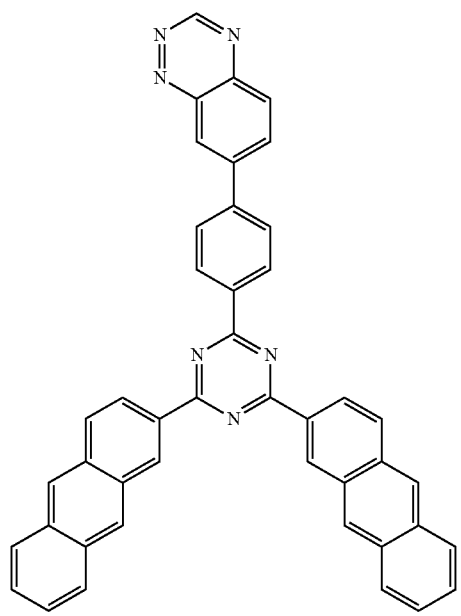
CP122
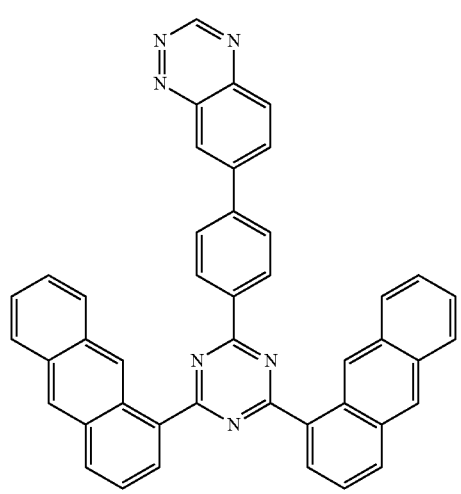
CP123
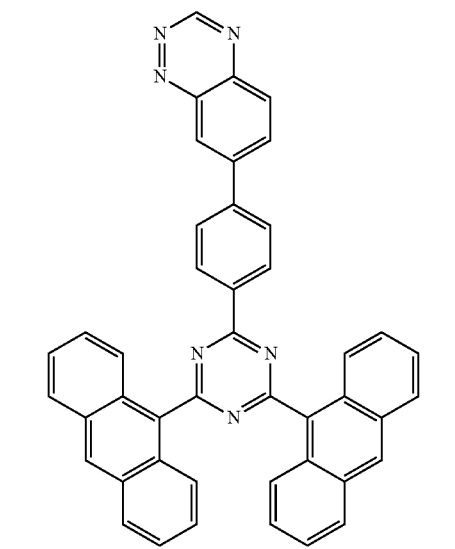

-continued
CP124
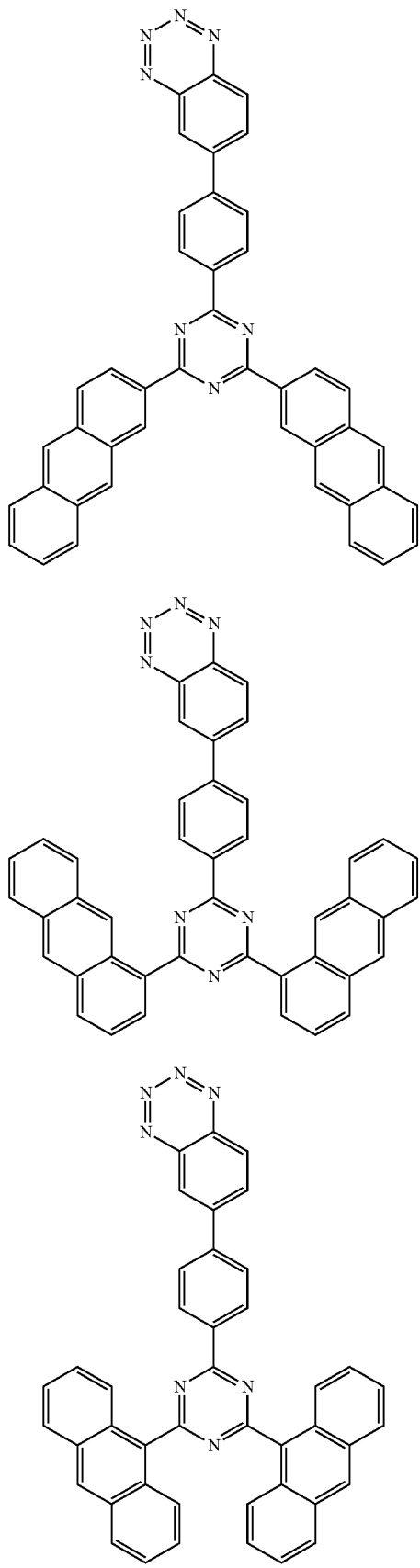
CP125
CP126
-continued
CP127
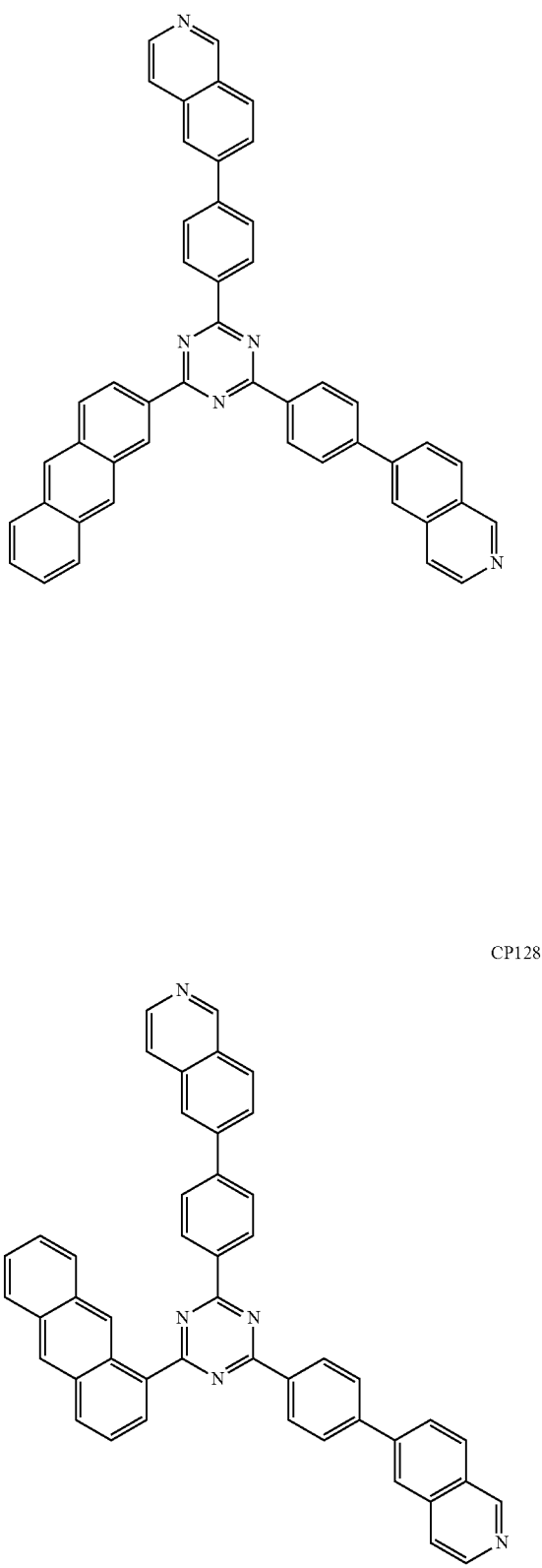
CP128

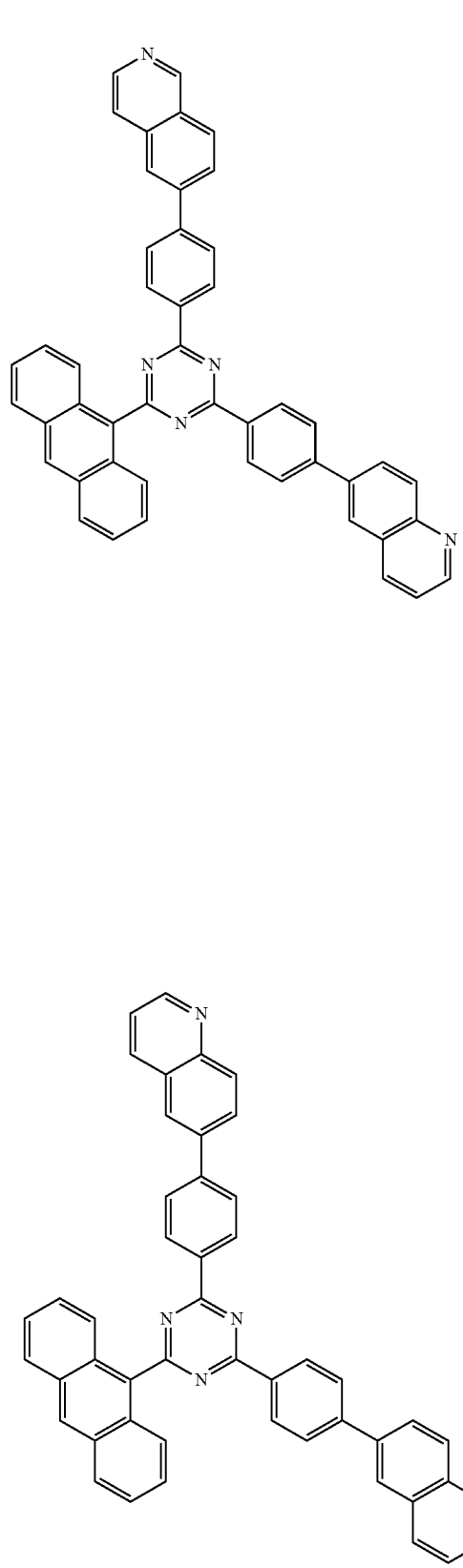
CP129
CP130
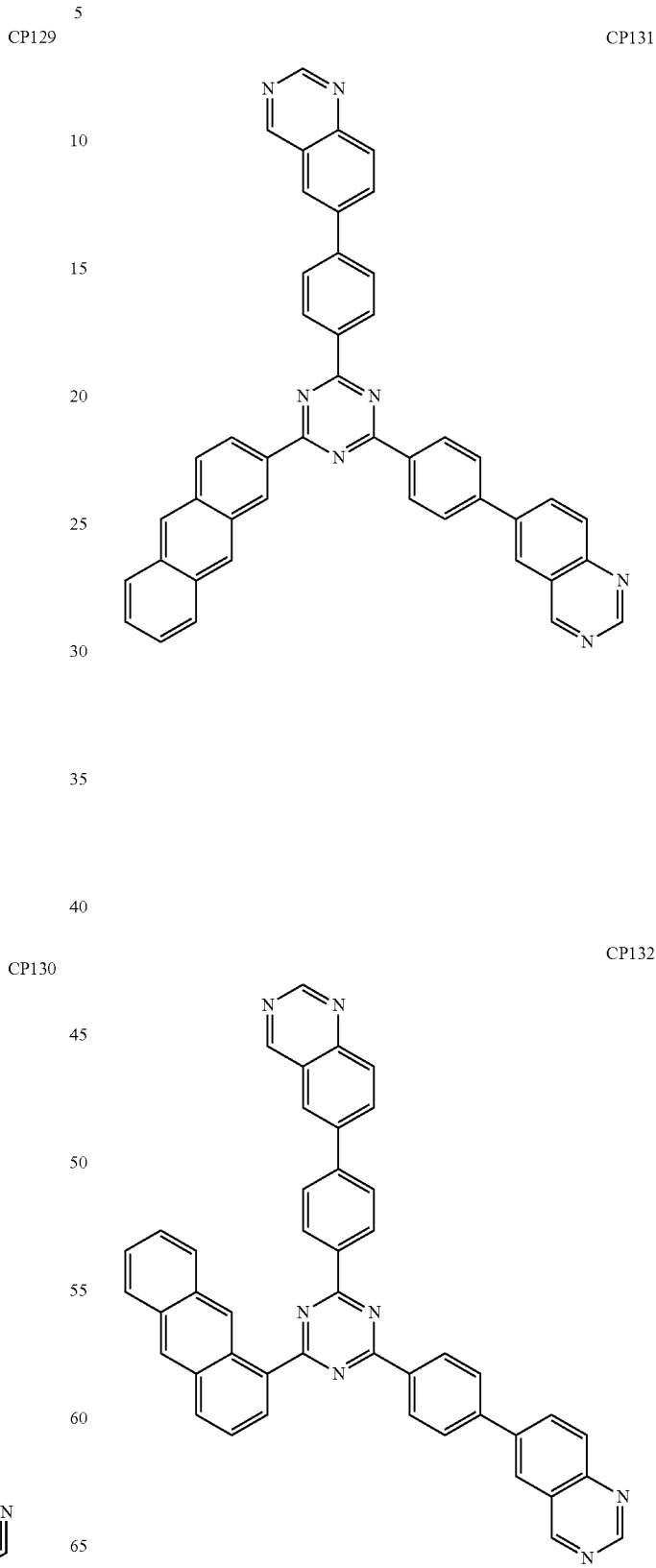
CP131
CP132

CP133
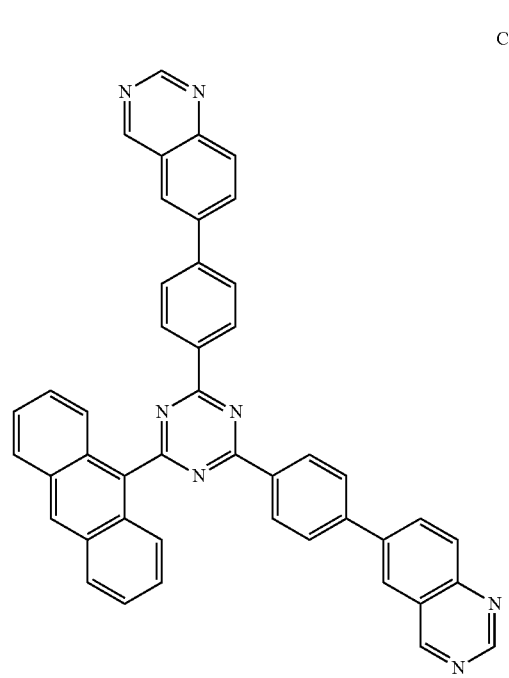
CP135
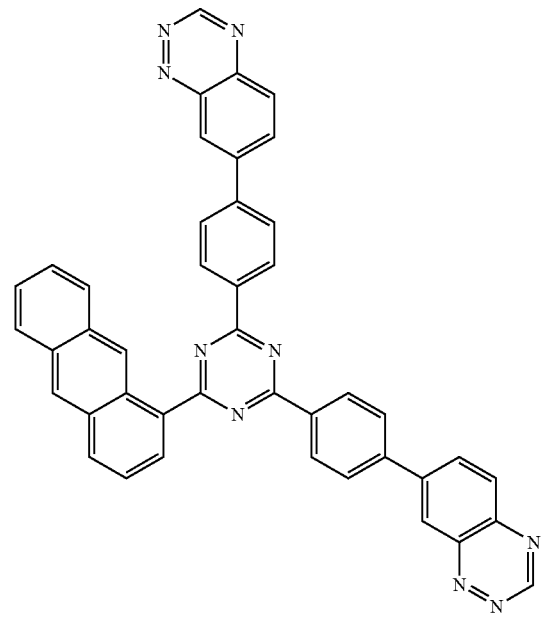
CP134
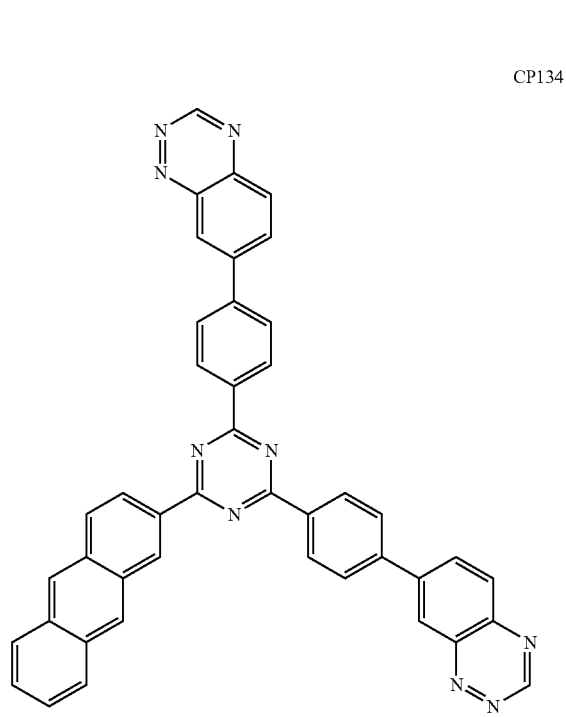
CP136
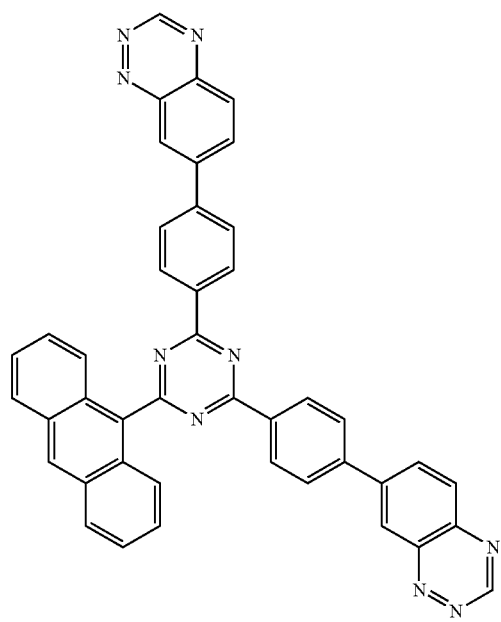

-continued
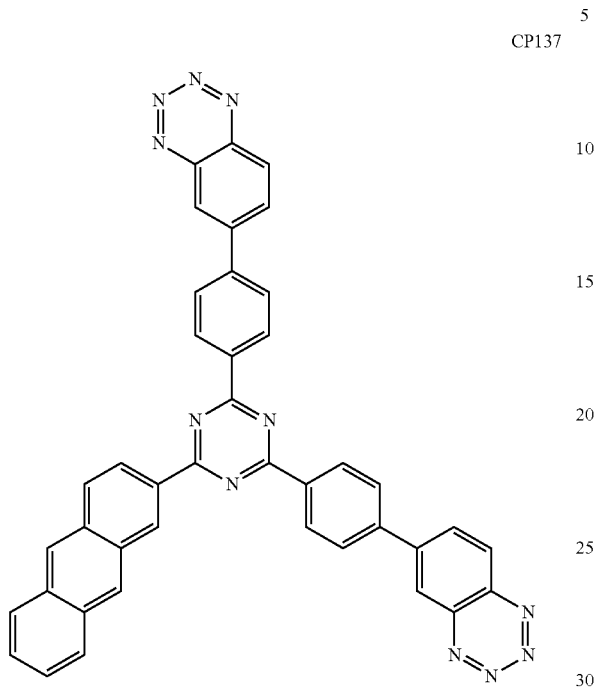
CP137
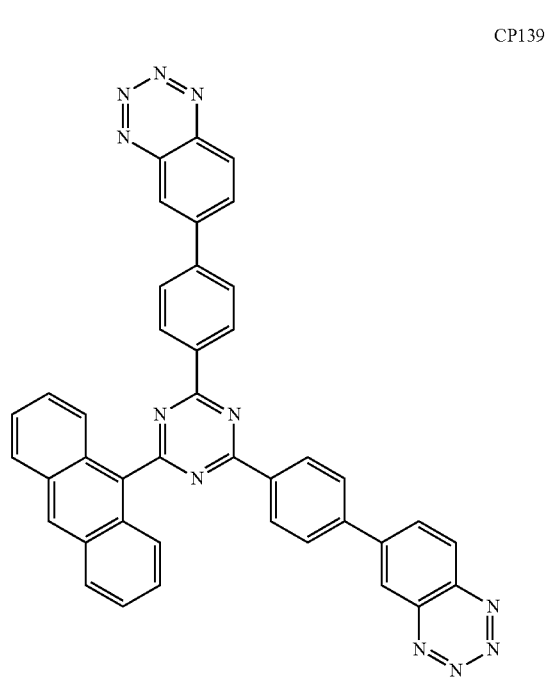
CP139
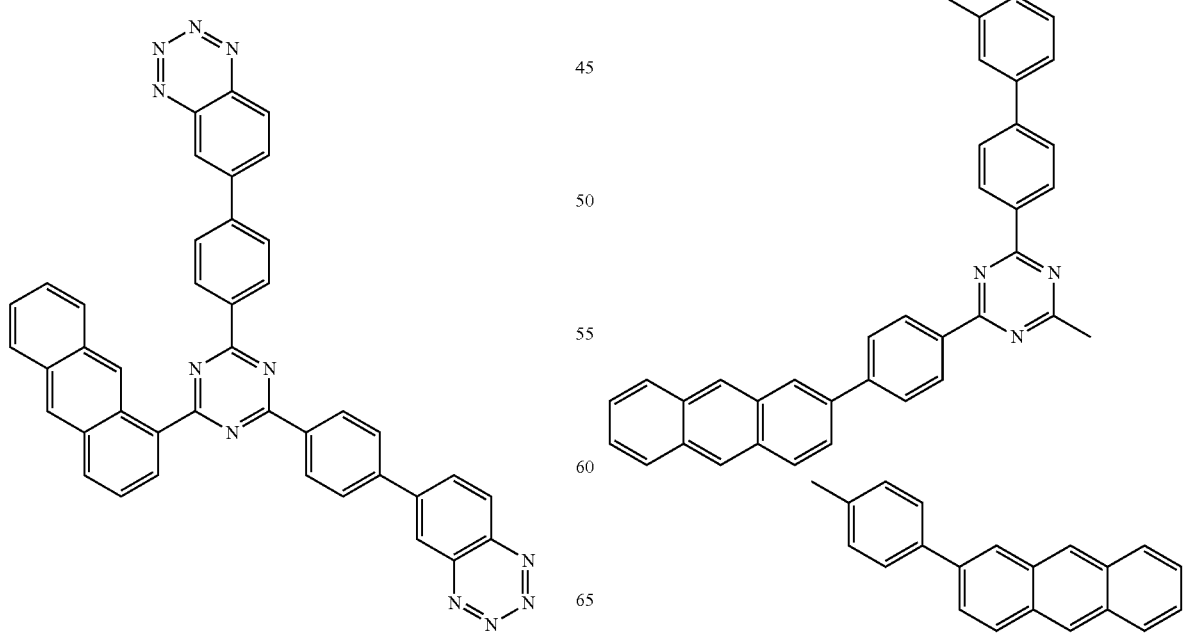
CP138
CP140

-continued
CP141
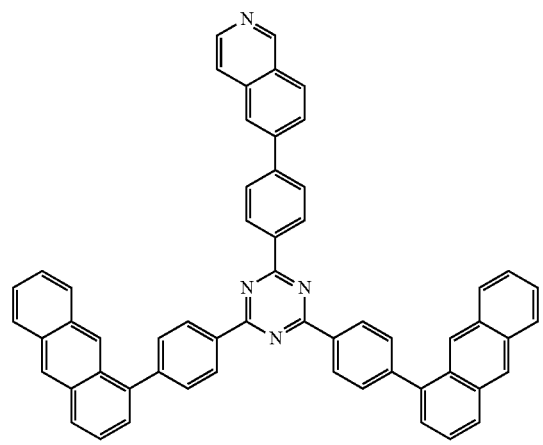
CP142
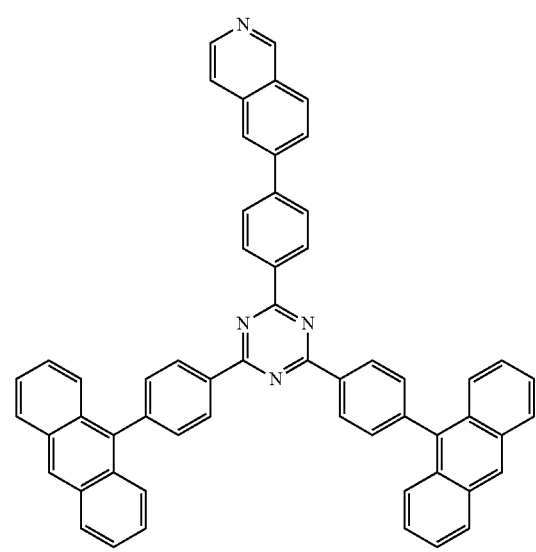
CP143
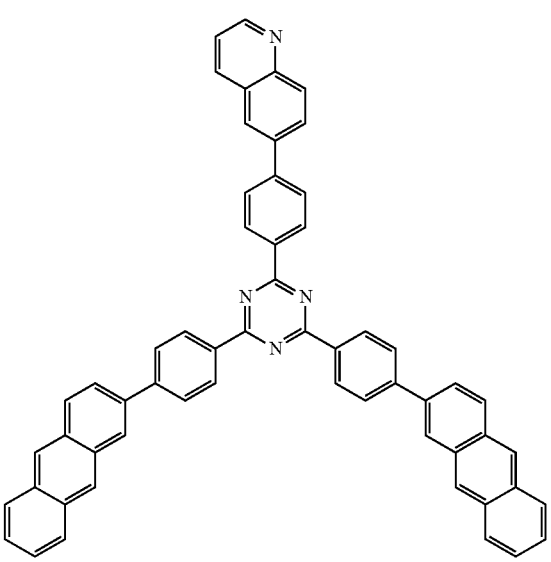
-continued
CP144
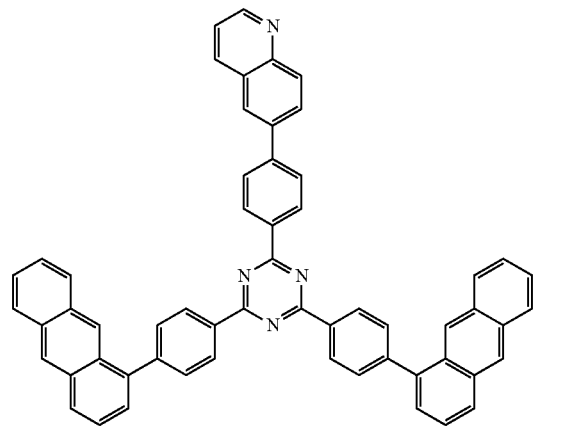
CP145
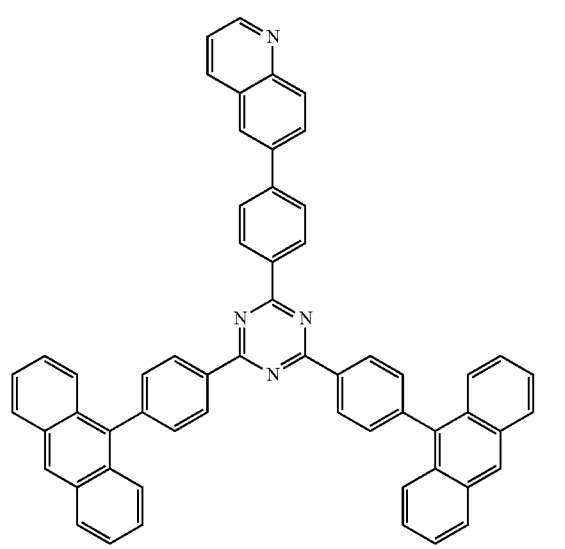
CP146
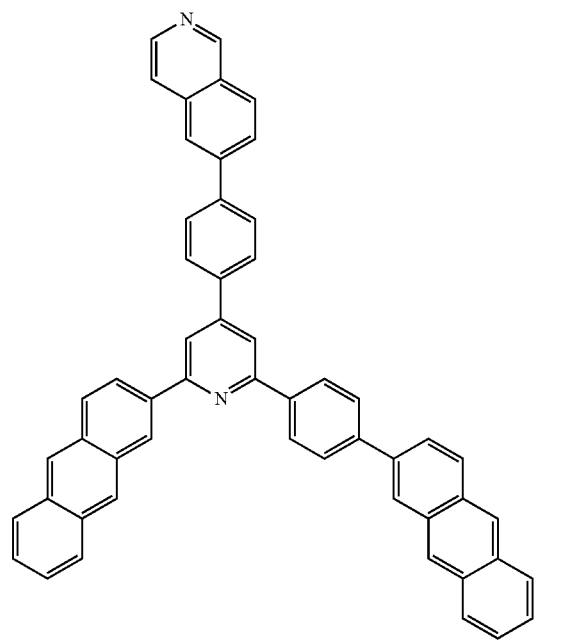

CP147
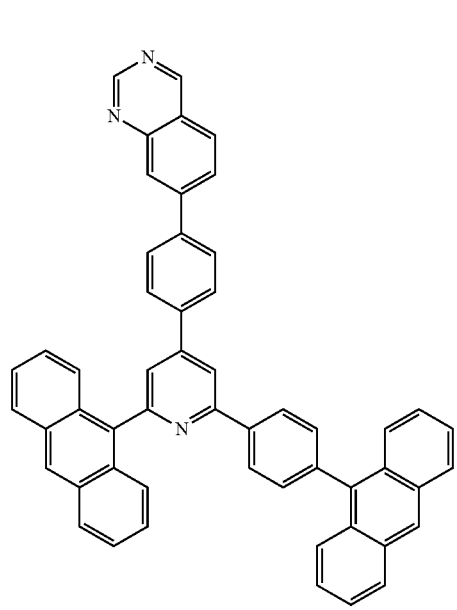
CP148
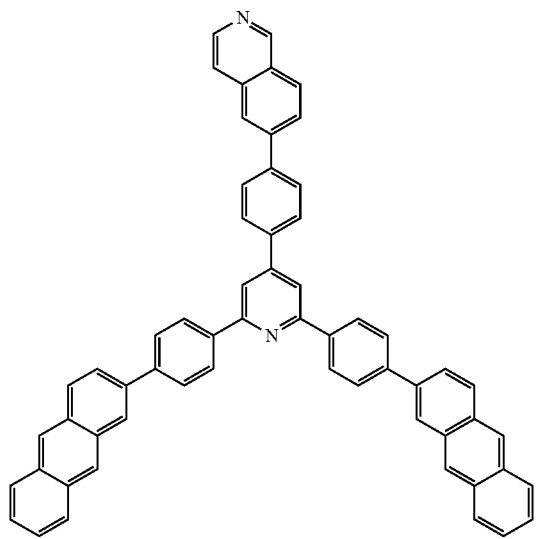
CP149
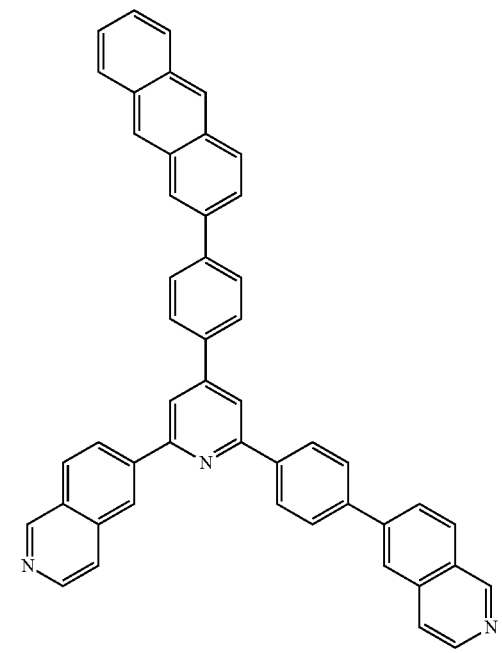
CP150
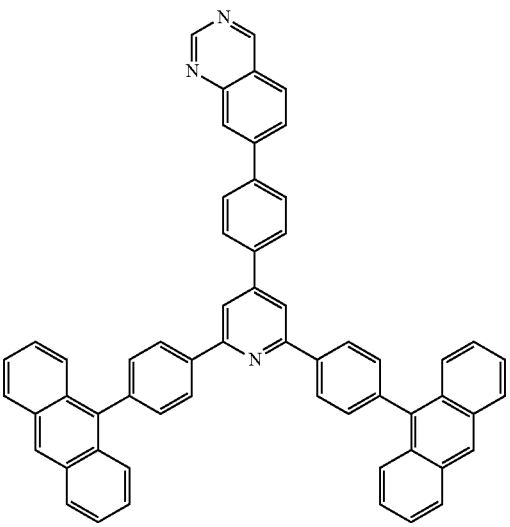

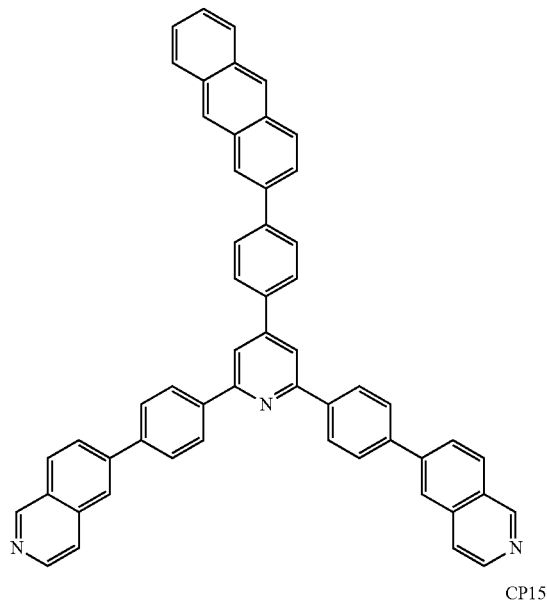

CP151

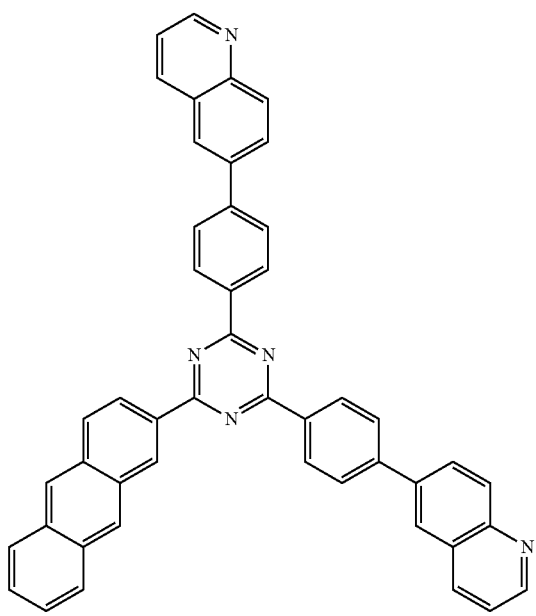

CP152

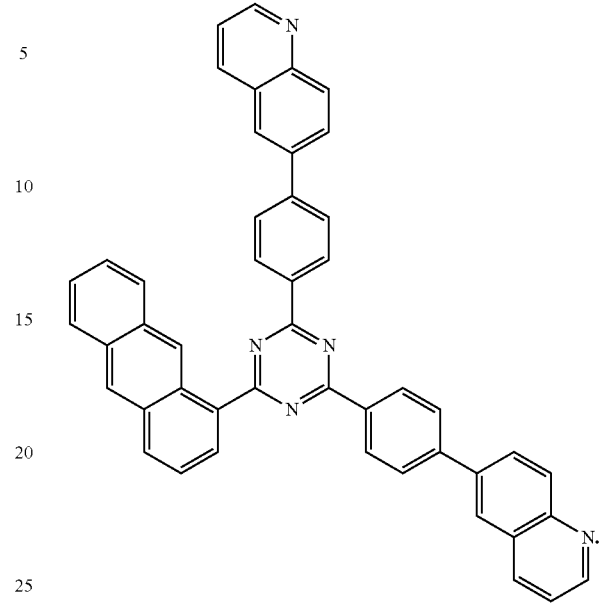

CP153

2. A display panel, comprising an organic light-emitting device,
wherein the organic light-emitting device comprises an anode, a cathode, and at least one organic layer disposed between the anode and the cathode, and
wherein a material of the at least one organic layer comprises at least one of compounds according to claim 1.

3. The display panel according to claim 2, wherein the at least one organic layer comprises an electron transport layer and a hole transport layer, and a material of the electron transport layer transport layer comprises at least one of compounds according to claim 1, and/or a material of the hole transport layer comprises at least one of compounds according to claim 1.

4. The display panel according to claim 3, wherein the organic light-emitting device further comprises a capping layer disposed on a side of the cathode facing away from the anode, and a material of the capping layer comprises at least one of compounds according to claim 1.

5. A display apparatus, comprising the display panel according to claim 2.

* * * * *